(12) United States Patent
Hurst et al.

(10) Patent No.: US 12,344,633 B2
(45) Date of Patent: Jul. 1, 2025

(54) SEPARATION AND ISOLATION OF NUCLEIC ACIDS USING AFFINITY LIGANDS BOUND TO A SOLID SURFACE

(71) Applicant: emp Biotech GmbH, Berlin (DE)

(72) Inventors: Alistair J. Hurst, Bunkeflostrand (SE); Derek W. K. Levison, Berlin (DE); Uwe Moeller, Berlin (DE)

(73) Assignee: EMP BIOTECH GMBH, Berlin (DE)

(*) Notice: Subject to any disclaimer, the term of this patent is extended or adjusted under 35 U.S.C. 154(b) by 981 days.

(21) Appl. No.: 17/103,323

(22) Filed: Nov. 24, 2020

(65) Prior Publication Data

US 2021/0155657 A1 May 27, 2021

Related U.S. Application Data

(60) Provisional application No. 62/939,934, filed on Nov. 25, 2019.

(51) Int. Cl.
*C07K 1/22* (2006.01)
*C07K 1/00* (2006.01)
*C07K 1/16* (2006.01)
*C07K 14/00* (2006.01)
*C07K 14/005* (2006.01)

(52) U.S. Cl.
CPC .............. *C07K 1/22* (2013.01); *C07K 1/00* (2013.01); *C07K 1/16* (2013.01); *C07K 14/003* (2013.01); *C07K 14/005* (2013.01)

(58) Field of Classification Search
CPC ... C07K 1/22; C07K 1/00; C07K 1/16; C07K 14/003; C07K 14/005; C07H 21/02; C07H 21/04; C07H 1/06; C07H 21/00; G01N 33/5308; C12Q 1/6806; C12Q 2565/50; C12Q 2563/173
See application file for complete search history.

(56) References Cited

U.S. PATENT DOCUMENTS

| | | |
|---|---|---|
| 4,627,918 A | 12/1986 | Saxena |
| 4,676,898 A | 6/1987 | Saxena |
| 5,658,751 A | 8/1997 | Yue et al. |
| 8,980,855 B2 | 3/2015 | Khvorova et al. |
| 2010/0233710 A1 | 9/2010 | McDougall et al. |

FOREIGN PATENT DOCUMENTS

| | | | | |
|---|---|---|---|---|
| CN | 101273995 A | 10/2008 | | |
| CN | 101273996 A | 10/2008 | | |
| WO | WO-2009020609 A2 * | 2/2009 | ......... | C12N 15/1006 |
| WO | 2014/051521 A1 | 4/2014 | | |
| WO | WO-2019098943 A1 * | 5/2019 | ............. | C12N 15/10 |

OTHER PUBLICATIONS

Bostock-Smith, C. E., et al. Chem. Commun., 1997, 121-122. (Year: 1997).*

Velagapudi, S. P., et al. J. Am. Chem. Soc. 2011, 133, 10111-10118. (Year: 2011).*
Thermo Scientific GlycoLink(TM) Immobilization Kit. Thermo Scientific. Instructions. 2024 (Year: 2024).*
Hoechst 34580 tetrahydrochloride. MedChem Express. 2024. Web. (Year: 2024).*
Bhaduri, S. et al., "An overview of recent advances in duplex DNA recognition by small molecules," Beilstein J. Org. Chem., 2018, 14, 1051-1086.
Chandrika, N.T. et al., "Synthesis and investigation of novel benzimidazole derivatives as antifungal agents," Bioorg. Med. Chem., Aug. 15, 2016, 24(16), 3680-3686.
Eckel, R. et al., "Identification of Binding Mechanisms in Single Molecule-DNA Complexes," Biophysical Journal, Sep. 2003, 85(3), 1968-1973.
Fei, X. et al., "Thiazole Orange Derivatives: Synthesis, fluorescence properties, and labeling cancer cells," Bioorganic & Medicinal Chemistry, 2009, 17(2), 585-591.
Fei, X. et al., "Solid-Phase Synthesis and Modification of Thiazole Orange and Its Derivatives and their Spectral Properties," J. Comb. Chem., 2007, 9(06), 943-950.
Frau, S. et al., "Synthesis and characterization of a cationic "manganese porphyrin-bisbenzimidazole dye (Hoechst 33258)" conjugate as a potential sequence-selective DNA cleaver," New J. Chem., 1995, 19, 873-876.
Gromov, S.P. et al., "Synthesis, Structure, and Properties of Supramolecular Photoswitches Based on Ammonioalkyl Derivatives of Crown Ether Styryl Dyes," J. Org. Chem., 2014, 79, 11416-11430.
Liu, Y. et al., "A "Double-Locked" and enzyme-activated molecular probe for accurate bioimaging and hepatopathy differentiation," Chem. Sci., 2019, 10, 10931-10936.
Nimesh, H. et al., "Synthesis and Biological Evaluation of Novel Bisbenzimidazoles as *Escherichia coli* Topoisomerase IA Inhibitors and Potential Antibacterial Agents," J. Med. Chem., 2014, 57, 5238-5257.
Pham, H. et al., "Bichromophoric Dyes for Wavelength Shifting of Dye-Protein Fluoromodules," Organic & Biomolecular Chemistry, 2015, 13, 3699-3710.
Ranjan, N. et al., "Selective Inhibition of *Escherichia coli* RNA and DNA Topoisomerase I by Hoechst 33258 Derived Mono- and Bisbenzimidazoles," J. Med. Chem., 2017, 60, 4904-4922.
Reddy, B.S. et al., "Synthetic DNA minor groove-binding drugs," Pharmacology & Therapeutics, 1999, 84, 1-111.
Reddy, B.S. et al., "Recent developments in sequence selective minor groove DNA effectors," Curr. Med. Chem., 2001, 8(5), 475-508 (Abstract only).

(Continued)

*Primary Examiner* — Eric Olson
*Assistant Examiner* — Samuel L Galster
(74) *Attorney, Agent, or Firm* — Hoffmann & Baron LLP

(57) ABSTRACT

A method of isolating and separating a target macromolecule, such DNA (double stranded or single stranded), RNA (double stranded or single stranded), messenger RNA, or other oligonucleotide or oligonucleoside, from a sample by binding the target macromolecule to an affinity ligand that is bound to a surface is disclosed. The method may be employed in chromatography or any other of the separation sciences.

17 Claims, 12 Drawing Sheets

(56) References Cited

OTHER PUBLICATIONS

Thermofisher Scientific, Molecular probes Handbook, A Guide to Fluorescent Probes and Labeling Technologies, Chapter 8, Nucleic Acid Detection and Analysis, 11th Ed (2010), 303-360.
Thompson, Martin, "Synthesis, Photophysical Effects, and DNA Targeting Properties of Oxazole Yellow-Peptide Bioconjugates," Bioconjugate Chem., 2006, 17(2), 507-513.
Wiederholt, K. et al., "DNA-Tethered Hoechst Groove-Binding Agents: Duplex Stabilization and Fluorescence Characteristics," J. Am. Chem. Soc., 1996, 118, 7055-7062.
Zhang, J. et al., "Recent Developments in C—H Activation for Materials Science in the Center for Selective C-H Activation," Molecules, 2018, 23(922), 2011-2024.
Invitation to Pay Additional Fees, and, Where Applicable, Protest Fee with Annex to Form PCT/ISA/206 and Provisional Opinion issued in International Application No. PCT/IB2020/061105 mailed Feb. 23, 2021 (11 pages).

\* cited by examiner

US 12,344,633 B2

SEPARATION AND ISOLATION OF NUCLEIC ACIDS USING AFFINITY LIGANDS BOUND TO A SOLID SURFACE

CROSS-REFERENCE TO RELATED APPLICATION

This application claims the benefit of priority of U.S. Provisional Patent Application No. 62/939,934, filed on Nov. 25, 2019. The entire contents of the foregoing application are incorporated by reference herein in its entirety.

FIELD OF THE INVENTION

This disclosure relates to a method of separating, isolating and removing target macromolecules, such as DNA and RNA, from a feed stream, or generically, a sample, using specifically selected affinity ligands bound to a surface.

BACKGROUND OF THE INVENTION

Chromatography, as it is generally used, is a technique for the separation of various components of a sample mixture. In a liquid chromatography system, a sample followed by an elution fluid is injected into a chromatographic separation column. The separation column contains a packing or matrix medium or material which interacts with the various components of the sample to be separated. The composition of the separating medium depends on the fluid being directed therethrough to effect the desired separation. As the sample and elution fluids pass through the separating medium, the various components of the sample travel at different rates through the separating medium as a result of differential interactions. These components emerge separated in the outlet or effluent from the separation medium.

Various types of the vertical and horizontal flow separation columns are known in the art. With the need for high performance chromatography, horizontal flow type chromatographic columns were developed. Such horizontal or radial flow columns are described in, e.g., U.S. Pat. Nos. 4,627,918 and 4,676,898. In the horizontal or radial flow type columns, the sample and elution fluids are introduced via a distributor to the outer periphery or circumferential wall or surface of the separating medium or matrix, and the fluids pass horizontally or radially inwardly through the separation medium to a central or collection port and then elute from the column at different times and at different rates.

Later, chromatographic columns and methods were developed for direct processing of crude feeds for isolation of biologically active materials, including cell/fermentation harvest, tissue extracts, and plasma/blood. The large bead chromatography media are packed into a standard, low pressure chromatography column in which end-plate screens are replaced with large pore screens (60-180 μm pores). The large pores prevent column blockage. Because particle sizes are large, the cellular material flows between the beads in the interparticle lumen, while the soluble product is captured by functional groups on the beads.

Traditionally, downstream processing of biologics from cell culture/fermentation harvests has required two major operations: recovery and purification. Recovery involves the removal of cellular and other particulate materials by centrifugation and/or microfiltration, as well as an initial volume reduction step, typically ultrafiltration. Since conventional chromatography media are rapidly fouled by cell debris, particle-free feed must be prepared for the purification operation.

In certain purification processes of (therapeutic) biological preparations (such as monoclonal antibodies), the sample/product is produced via a living cell system (mammalian, bacterial, moss, algae, plant, etc.) and the product is either secreted into the feed stream by the cells or the cells are broken up to release the product into the surrounding liquid. However, in all of these production systems, the product is not available as a single component pure product, but is a very complex mix of the desired product and "contaminants," which includes host cell protein (HCP) and genomic DNA and RNA.

During purification, HCP and DNA/RNA must be removed from the purified product to levels that are below limits set by regulatory authorities (such as the FDA). This purification is usually achieved by anion ion exchange methods. During filtration and purification of samples containing proteins, it may be difficult to separate the proteins from other cell components and host proteins without degenerating the protein of interest, and also to isolate the target proteins. A common method is through precipitation; however, this may lead to denaturation or degeneration of the protein which may result in a loss of protein function. Refolding of the protein often leads to a loss in activity. Fast Protein Liquid Chromatography (FPLC) is a common method employed in protein purification. Without having to denature the protein, using high pressure or aggressive pH-buffers, proteins may be purified using solely specific interactions between the buffer and the protein of interest for isolation.

There remains a need for a system for removal and isolation of DNA and RNA, both double and single stranded, from a feed stream.

SUMMARY OF THE INVENTION

A method of separating a target macromolecule from a sample is disclosed, comprising the steps of: selecting an affinity ligand that will bind to the target macromolecule; binding the affinity ligand to a surface to create a coupled surface-affinity ligand; placing the coupled surface-affinity ligand into a container; introducing the sample containing the target macromolecule to the coupled surface-affinity ligand and causing the coupled surface-affinity ligand to incubate with the sample for a residence time, wherein the target macromolecule binds to the affinity ligand; and separating the coupled surface-affinity ligand bound to the target macromolecule from the sample that has the target macromolecule removed therefrom. Optionally, the method includes collecting an eluent that is substantially free of the target macromolecule, and/or eluting and recovering the target macromolecule from the coupled surface-affinity ligand.

The target macromolecule may be double stranded DNA, single stranded DNA, double stranded RNA, single stranded RNA, double stranded messenger RNA, single stranded messenger RNA, locked nucleic acid (LNA), peptide nucleic acid (PNA), virus, protein containing an oligonucleotide or oligonucleoside, lipid containing an oligonucleotide or oligonucleoside, other oligonucleotide or oligonucleoside, any fragment thereof, or any combination thereof. In certain embodiments, the affinity ligand does not bind to proteins in the sample, and/or is methylene blue, a Hoechst dye, a cyanine of a benzothiazole-quinoline, or a cyanine of a benzoxazole-quinoline. The surface may be a solid surface, such as a bead, membrane, particle, mesh, polymer, glass, metal, ceramic, silica, polysaccharide, monolith, or any other material used as a resin in chromatography, that includes a functionalized group. The container may be a chromatography column, bowl, cylinder, conical-shaped vessel, or vat.

Also disclosed is a method for isolating and removing DNA from a sample containing DNA and other nucleic acids and a method for isolating and removing RNA from a sample containing RNA and other nucleic acids. These methods include the steps of: selecting an affinity ligand that will bind the target DNA or RNA; binding the affinity ligand to a surface to create a coupled surface-affinity ligand; placing the coupled surface-affinity ligand into a container; introducing the sample to the coupled surface-affinity ligand and causing the coupled surface-affinity ligand to incubate with the sample for a residence time, wherein the target DNA or RNA binds to the affinity ligand; and separating the coupled surface-affinity ligand bound to the target DNA or RNA from the sample that has the target DNA or RNA removed therefrom.

DESCRIPTION OF THE FIGURES

FIG. 1A shows % DNA bound to gel of total DNA added, and FIG. 1B shows capacity (in µg DNA/mL gel) of gel to bind DNA. Black=MCMB-agarose; Grey=control (no MCMB present on gel).

FIG. 2A=% DNA bound to gel of total DNA added, FIG. 2B=Capacity (in µg DNA/mL gel) of gel to bind DNA. White=native agarose bead w/o amino groups; Black=amino functionalized agarose beads; Grey=DNA, either at a concentration of <50 bp or <2000 bp.

FIG. 3A=3.3 mg/mL, FIG. 3B=1.5 mg/mL, FIG. 3C=0.33 mg/mL, FIG. 3D=0.15 mg/mL.

DETAILED DESCRIPTION

Figure 1A:
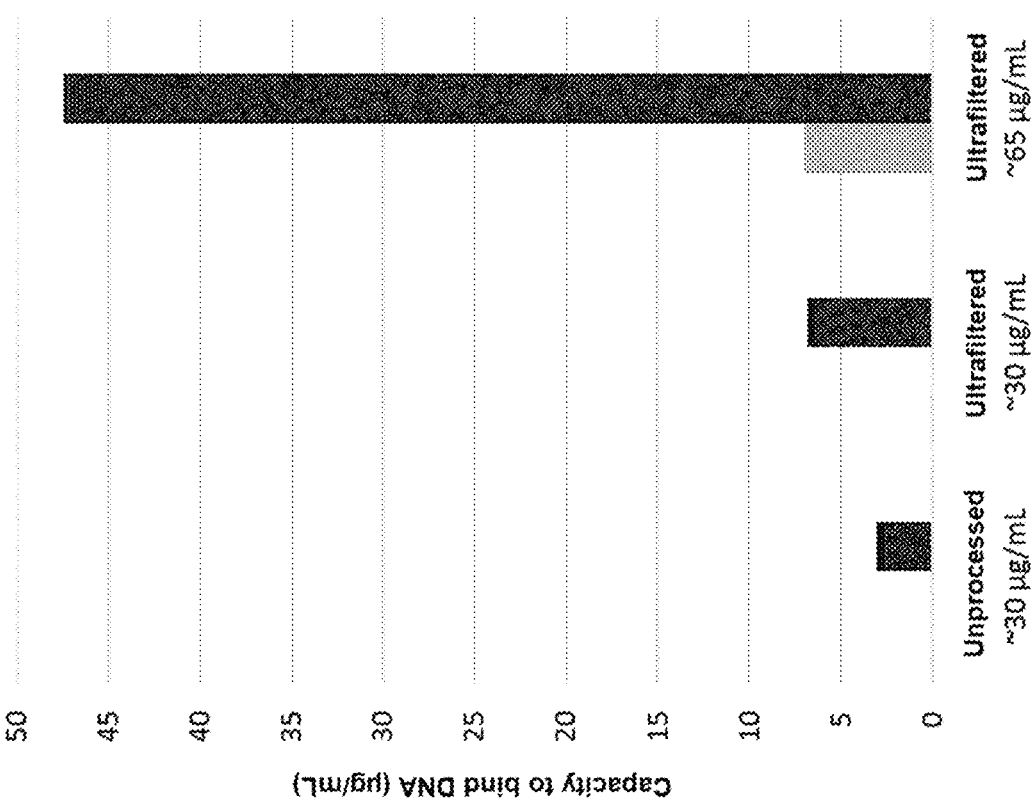
FIGS. 1A and 1B are bar graphs showing a comparison of DNA (size <50 bp) unprocessed and "ultrafiltered" in two concentrations of MCMB-beaded agarose gel (30 µg MCMB per mL gel and 65 µg MCMB per mL gel, MCMB=monocarboxymethylene blue). percentage of DNA bound in two concentrations of MCMB-beaded agarose gel.

Methods of capturing and removing target macromolecules from a biological feed stream, e.g., unclarified (i.e., un-filtered) cell culture, are disclosed herein. In an embodiment, special capture ligands, which may be major groove binders, minor groove binders, or intercalating ligands (together referred to as "affinity ligands") may be bound, e.g., covalently, to a solid surface and are used to irreversibly or reversibly capture target macromolecule(s), such as DNA, RNA, and lipids and proteins containing oligonucleotides, from complex mixtures such as cell culture feed streams. This method is used in the separation sciences, including but not limited to, chromatography, filtration, distillation and evaporation. Chromatography includes any known method of chromatography, including but not limited to, radial flow chromatography, axial chromatography, batch chromatography, adsorption chromatography, expanded bed chromatography, simulated moving bed chromatography, counter current chromatography, high pressure and high performance liquid chromatography. Filtration includes any known method of filtration in the art, including but not limited to, membrane filtration, hollow fiber filtration, and tangential flow/cross flow filtration, Disclosed herein is a method of filtration, separation, isolation, removal and/or purification of a nucleic acid using an affinity ligand (a molecule that exhibits a defined interaction with the target molecule). The method comprises the steps of: (a) selecting an affinity ligand that will bind to the target macromolecule; (b) binding the affinity ligand to a surface to create a coupled surface-affinity ligand; (c) placing the coupled surface-affinity ligand into a container; (d) introducing a sample containing the target macromolecule to the coupled surface-affinity ligand and causing the coupled surface-affinity ligand to incubate with the sample for a residence time, wherein the target macromolecule binds to the affinity ligand in the container; and (e) separating the coupled surface-affinity ligand bound to the target macromolecule from the sample that has the target macromolecule removed therefrom. Optionally, the method further comprises (f) collecting the eluent, i.e., the sample that has the target macromolecule removed therefrom.

The affinity ligand may be irreversibly immobilised and adhered to a surface in such a way that it can interact with and bind a target macromolecule. The target macromolecule may be a nucleic acid, or fragment thereof. The nucleic acid may be double stranded DNA, single stranded DNA, double stranded RNA, single stranded RNA, double stranded messenger RNA, single stranded messenger RNA, locked nucleic acid (LNA), peptide nucleic acid (PNA), virus, protein containing an oligonucleotide or oligonucleoside, lipid containing an oligonucleotide or oligonucleoside, other oligonucleotide or oligonucleoside, any fragment thereof or any combination thereof. The target macromolecule may be double stranded DNA, single stranded DNA, double stranded RNA, single stranded RNA, double stranded messenger RNA, single stranded messenger RNA, any fragment thereof, or any combination thereof.

The affinity ligand may be a minor groove binder, a major groove binder or intercalating ligand. The affinity ligand used in each filtration and/or purification process is individually selected to reduce or eliminate cross-reactivity (unwanted binding) with molecules other than the target macromolecule. The affinity ligand may be any molecule known to be a minor groove binder, a major groove binder or intercalating ligand, and further any molecule known to be a minor groove binder, a major groove binder or intercalating ligand that also is observed to have further selectivity toward a target macromolecule.

In an embodiment, an affinity ligand may be selected that binds large strands of DNA and has minimal to no noticeable interaction with proteins. An affinity ligand may be selected that binds double stranded DNA, single stranded DNA, double stranded RNA, single stranded RNA, double stranded messenger RNA, single stranded messenger RNA, any fragment thereof, or any combination thereof, and has minimal to no noticeable interaction with the other oligonucleotides.

The surface may be a solid surface that optionally has been functionalized to include, for example, an ionic exchange group, or hydrophobic interaction group. The surface may have a functionalized group, such as a spacer ending in an epoxy, carboxy, aldehyde, halide or amino group. Spacer refers to a chain of atoms, preferably one to thirty, or one to twenty atoms, attached to the solid surface. The spacer may contain an ester, a carboxyl group, or a carbon chain (e.g., alkyl). The spacer may contain a polyethyleneglycol moiety, such as $(CH_2CH_2O)_nCH_2CH_2$—, where n=1-10. The spacer may be a $C_{1-20}$ alkylamino, $C_{1-12}$ alkylamino, or $C_{2-12}$ alkylamino. After reaction, the spacer will be between and connecting the solid surface and the affinity ligand.

The solid surface may be a bead, membrane, particle, mesh, polymer, glass, metal, ceramic, silica, polysaccharide, monolith, or any other material used as a resin in chromatography that optionally has been functionalized as above. The bead may be an agarose bead or an amino-agarose bead. The membrane may be an aldehyde membrane, such as one made from the Sartobind® Aldehyde A4 Sheet. The monolith may be epoxy or ethylenediamine (EDA)—AEX/Activated.

The surface may be a membrane when the method employed is batch chromatography. The surface may be a bead when the method employed is axial or radial flow chromatography.

The affinity ligand is bound to the surface and captures the target macromolecule when a sample or feed stream containing the target macromolecule comes in contact with the affinity ligand. The affinity ligand may be bound to the surface by any means known in the art. Examples include, but are not limited to, bond formation via amide bond formation using N-hydroxysuccinimide activated carboxylic acids, reaction with aldehyde/Schiff's base, reaction with epoxy groups, click chemistry, and Michael additions.

The bound affinity ligand can be re-used or disposed of after a single use, i.e., a single-use product. For regulatory purposes, a disposable, single-use product may be preferable, such that there is no question as to whether any residual contaminant remains after cleaning after each use. In addition, cleaning would be very costly and may be technically difficult.

As such, the affinity ligand selectively binds the target macromolecule thereby providing an eluent that is substantially free of the target macromolecule. The target macromolecule is isolated from the remainder of the sample, optionally, for recovery and further experimentation and/or treatment, if warranted. The affinity ligand may selectively bind the target macromolecule while not binding to proteins. For example, the immobilization and isolation of DNA may occur by using a coupled surface-affinity ligand as the intercalating molecule, e.g., an amino-agarose bead coupled with modified methylene blue, or a modified Hoechst dye. After incubation, the DNA is bound to the affinity ligand and may be separated from the sample.

Recovery of DNA from the affinity ligand may be based on ionic interactions between a solid phase such as silica or glass. A binding buffer, usually of high ionic strength and at a pKa at or below the pKa of surface silanol group, allows both binding of DNA with concomitant washing of impurities. The DNA is then typically eluted using a low ionic strength buffer. Disadvantages are the high pH of cleavage buffers used to remove DNA from the solid phase of synthesis columns; high pH may dissolve silica which ends up as an impurity in the DNA.

After depletion or removal of some or all of the target macromolecule from the feed stream, the eluent may contain less than about 5% by weight of the target macromolecule, less than about 2% by weight of the target macromolecule, less than about 1% by weight of the target macromolecule, less than about 0.5% by weight of the target macromolecule, less than about 0.2% by weight of the target macromolecule, less than about 0.1% by weight of the target macromolecule, less than about 0.05% by weight of the target macromolecule, less than about 0.01% by weight of the target macromolecule, less than about 0.005% by weight of the target macromolecule, or less than about 0.001% by weight of the target macromolecule.

Explained in another way, the affinity ligand may bind at least about 50% by wt., at least about 60% by wt., at least about 70% by wt., at least about 80% by wt., or at least about 85% by wt. of the target macromolecule in a sample. The affinity ligand may bind about 50% to about 99% by wt. of the target macromolecule in a sample, about 60% to about 98% by wt. of the target macromolecule in a sample, or about 70% to about 98% by wt. of the target macromolecule in a sample, The affinity ligand may exhibit minor groove binding, or major groove binding with the target macromolecule. Minor groove binding is characterized by selective binding to the narrow minor groove of AT-rich sequences by van der Waals interaction, hydrogen bonds, and electrostatic interaction. Reddy, et al., "Recent developments in sequence selective minor groove DNA effectors," Curr. Med. Chem., 8 (2001), pp. 475-508. Major groove binding is characterized by electrostatic interactions of helical ligands with the backbone as well as with hydrogen bonds. Eckel, R., et al, "Identification of Binding Mechanisms in Single Molecule-DNA Complexes," Biophys. J., 2003 September, 85(3): 1968-1973.

The affinity ligand may exhibit intercalation with the target macromolecule. Intercalation is a reversible insertion of a molecule (or ion) into a material. In an embodiment, when the target macromolecule is DNA, the affinity ligand interacts with DNA by intercalating, such that the ligands of an appropriate size and chemical nature fit themselves in between base pairs of DNA. These affinity ligands are mostly polycyclic, aromatic, and planar. The affinity ligand may be a dye. The affinity ligand is selected based on the target macromolecule and the selected solid surface. The affinity ligand is not sequence specific. In certain embodiments, the affinity ligand is not charged, and optionally, does not bind to any protein in the feed stream. If it were charged, the ligand may bind indiscriminately to proteins or other substances. In an embodiment, when the target macromolecule is DNA, the affinity ligand may be a modified methylene blue, a modified Hoechst dye, a modified thiazole orange, or a modified oxazole yellow that selectively binds DNA, and optionally does not bind proteins.

The affinity ligand can be modified to be capable of binding to any solid surface (i.e., bead, membrane, particle, mesh, net, polymer, glass, metal, ceramic, silica, polysaccharide, monolith, or other solid phases) and can bind to one of more of the target macromolecules, in order to isolate, segregate, remove, enrich or purify the target macromolecule from a sample, reaction, or feed stream. When the surface is a bead, any bead known for use in chromatography that also is capable of binding to the affinity ligand may be used. The bead may be functionalized glass or agarose, for example, bound to a modified methylene blue, a modified Hoechst dye, or a modified cyanine of a benzothiazole-quinoline or benzoxazole-quinoline, such as a modified thiazole orange, a modified oxazole yellow. The bead may be glass or agarose having an aldehyde, carboxylic acid or epoxy group, for example, bound to an alkylamino on a modified affinity ligand. When the surface is a membrane, the membrane may be bound to a modified methylene blue, a modified Hoechst dye or a modified cyanine of a benzothiazole-quinoline or benzoxazole-quinoline, such as a modified thiazole orange, a modified oxazole yellow.

To modify the affinity ligand: first analyze or identify an optimal point of attachment for the linker or spacer group (e.g., that which will not interfere with the cite where the ligand recognizes the target macromolecule); and second, develop a synthetic strategy to introduce a linker group of appropriate length utilizing standard synthetic techniques known in the art to prevent unwanted and uncontrolled groups on the ligand and ensuring one end of the linker group has an appropriate functional group to chemically bind to the solid surface.

The affinity ligand may be any intercalator, minor groove binder or major groove binder that has been modified to chemically bind to a functionalized surface. The affinity ligand may be selected from acridines, polyimidazoles, indoles, pyrroles, phenanthridines, Cyanines of Benzothiazole-Quinolines or Benzoxazole-Quinolines, phenoxazines, phenothiazines, anthraquinones, furanocoumarin, any modifications thereof, or any other ligands capable of binding to the surface and capturing the target macromolecule.

Acridine structures useful in accordance with the disclosure include, but are not limited to, GelGreen (10,10'-(6,22-dioxo-11,14,17-trioxa-7,21-diazaheptacosane-1,27-diyl)bis(3,6-bis(dimethylamino)acridin-10-ium) iodide), acridine orange (N,N,N',N'-Tetramethylacridine-3,6-diamine) and derivatives thereof, amsacrine (also known as synonyms: m-AMSA, acridinyl anisidide), and acriflavins (3,6-Diamino-10-methylacridin-10-ium chloride) and derivatives thereof, including proflavine (also called proflavin and diaminoacridine; acridine-3,6-diamine).

Poly imidazoles, Indoles, and Pyrroles useful in accordance with the disclosure include, but are not limited to, "Hoechst" dyes (i.e. Hoechst 33258, Hoechst 33342 (aka bisbenzimide), and Hoechst 34580) (https://en.wikipedia.org/wiki/Hoechst_stain), known to intercalate with DNA/RNA, DAPI (4',6-diamidino-2-phenylindole, is a fluorescent stain that binds strongly to adenine-thymine-rich regions in DNA), Lexitropsins, Netropsins (a polyamide also referred to as congocidine or sinanomycin), and Distamycin (is a polyamide-antibiotic, which acts as a minor groove binder, also known as Herperetin, Stallimycin).

Lexitropsins are members of a family of semi-synthetic DNA-binding ligands. The may bind in the minor groove of DNA. Lexitropsins form a complexes with DNA with stoichiometry 1:1 and 2:1. Lexitropsins may have but are not limited to the following structures:

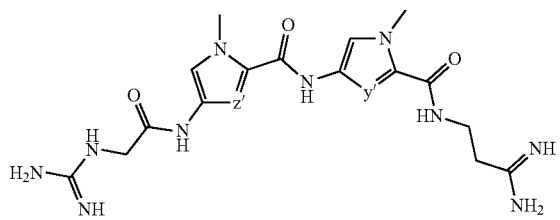

(a) y' = CH, z' = CH
(b) y' = CH, z' = N
(c) y' = N, z' = CH
(d) y' = V, z' = N

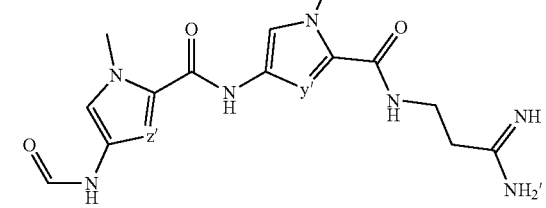

(e) y' = CH, z' = N
(f) y' = N, z' = CH
(g) y' = N, z' = N

Phenanthridine structures useful in accordance with the disclosure include, but are not limited to, Phenanthridines and derivatives thereof, such as, for example, Ethidium bromide, Propidium iodide, Propidium monoazide, and GeRed (5,5'-(6,22-dioxo-11,14,17-trioxa-7,21-diazaheptacosane-1,27-diyl)bis(3,8-diamino-6-phenylphenanthridin-5-ium) iodide).

Cyanines of Benzothiazole-Quinoline and Benzoxazole-Quinoline structures useful in accordance with the disclosure include, but are not limited to, "Sybr Green" family of dyes (including, but not limited to, Sybr Green I (N',N'-dimethyl-N-[4-[(E)-(3-methyl-1,3-benzothiazol-2-ylidene)methyl]-1-phenylquinolin-1-ium-2-yl]-N-propylpropane-1,3-diamine), Sybr Green II, Sybr Gold, and Sybr Safe ((Z)-4-((3-Methylbenzo[d]thiazol-2(3H)-ylidene)methyl)-1-propylquinolin-1-ium 4-methylbenzenesulfonate)), TOTO™ family of dyes and derivatives thereof, YOYO™ family of dyes and derivatives thereof, YO-PRO™ family of dyes and derivatives thereof, TO-PRO™ family of dyes and derivatives thereof, POPO™ family of dyes and derivatives thereof, BOBO™ family of dyes and derivatives thereof, LOLO™ family of dyes and derivatives thereof, JOJO™ family of dyes and derivatives thereof, (See ThermoFisher Scientific, *Molecular probes Handbook, A Guide to Fluorescent Probes and Labeling Technologies*, Chapter 8, *Nucleic Acid Detection and Analysis*, 11$^{th}$ Ed (2010), available at: https://www.google.com/url?sa=t&rct=j&q=&esrc=s&source=web&cd=3&ved=2ahUKEwiL5N P478fdAhVq h4sKHffbCFkQFjACegQICBAC&url=http %3A %2F %2Fwww.thermofisher.com%2Fcontent%2Fdam%2FLife Tech%2Fglobal%2Ftechnical-reference-library%2FMole cular%2520Probes%2520Handbook%2Fchapter-pdfs% 2FCh-8-Nucleic-Acid-Detection-Analysis.pdf&usg=AOv Vaw2Ufpb7SkFbbWTbbzAwdgtm), Thiazole Orange and derivatives thereof, Oxazole Yellow and derivatives thereof, Pico Green and derivatives thereof

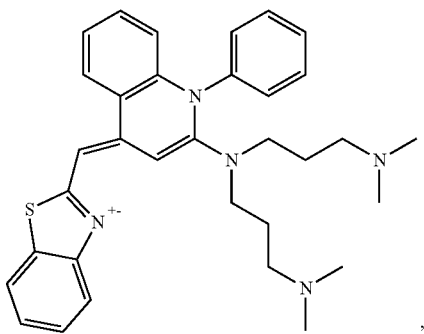 [SMILES: CN(C)CCCN(CCCN(C)C)C1=C/C(=C\c2nc3ccccc3s2)c2ccccc2N1c1ccccc1]

and LightCycler® Green and Red family of dyes.

Phenoxazines useful in accordance with the disclosure include, but are not limited to, 7-Aminoactinomycin D, actinomycin D and derivatives thereof.

Phenothiazines useful in accordance with the disclosure include, but are not limited to, Methylene Blue (also known as methylthioninium chloride) and derivatives thereof, including but not limited to, Dicarboxymethylene Blue NHS ester (DCMB-SE), and Monocarboxymethylene Blue (MCMB).

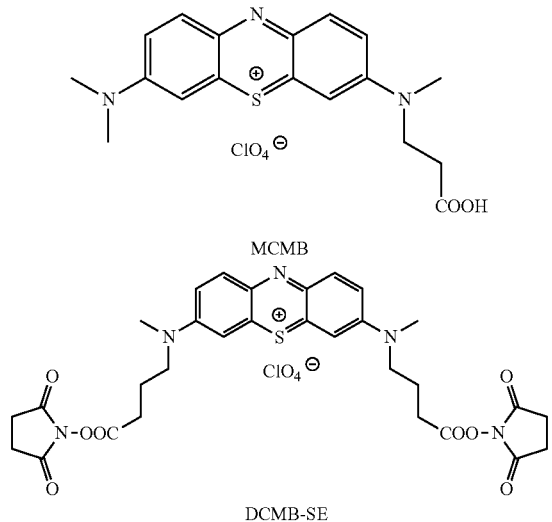

Anthraquinone structures useful in accordance with the disclosure include, but are not limited to, anthracyclines and derivatives thereof, Daunorubicin (also known as also known as also known as daunomycin), and Doxorubicin.

Mitoxantrone, Losoxantrone (an anthroquinone anthrapyrazole antineoplastic agent and analog of mitoxantrone), Pixantrone, Pirarubicin and other anthraquinone analogs thereof (e.g., anthraquinone-2-amidopentyl carboxylic acid NHS ester)

Furanocoumarin structures useful in accordance with the disclosure include, but are not limited to, psoralen, angelicin, bergamottin ((E)-4-[(3,7-Dimethyl-2,6-octadienyl)oxy]-7H-furo[3,2-g][1]benzopyran-7-one) and derivatives thereof, and amikhelline ($C_{18}H_{21}NO_5$) and derivatives thereof.

Other affinity ligands useful in accordance with the disclosure include, but are not limited to, methyl green ($C_{27}H_{35}Cl_2N_3$), though this has a largely ionic interaction with DNA, and ellipticine (5,11-dimethyl-6H-pyrido[4,3-b]carbazole).

The affinity ligand may be any of the above acridines, polyimidazoles, indoles, pyrroles, phenanthridines, Cyanines of Benzothiazole-Quinolines or Benzoxazole-Quinolines, phenoxazines, phenothiazines, anthraquinones, furanocoumarin, or other ligands capable of binding to the surface and capturing the target macromolecule. The affinity ligand may be intercalator, minor groove binder, major groove bind, or combination thereof, that has been modified by either a) attaching a linker group to a functional group already present on the compound or dye, and that linker group is then bound to the surface, or b) chemically altering the compound or dye to include a linker group, and that linker group is then bound to the surface. The linker group may be any reactive linker containing a spacer ending in an epoxy, carboxy, aldehyde, halide or amino group. Spacer refers to a chain of atoms, preferably one to thirty, or one to twenty atoms, attached to the affinity ligand. The spacer may contain an ester, a carboxyl group, or a carbon chain. The spacer may contain a polyethyleneglycol moiety, such as $(CH_2CH_2O)_nCH_2CH_2$—, where n=1-10. The spacer may be a $C_{1-20}$ alkylamino, $C_{1-12}$ alkylamino, or $C_{2-12}$ alkylamino. The halide may be any halogen, or it may be F, CL, Br or I. After reaction, the spacer will be between and connecting the surface and the affinity ligand. The linker group may be an alkylamino group, such as $C_{2-12}$ alkylamino, or $C_{2-8}$ alkylamino.

In an embodiment, the affinity ligand is methylene blue, a Hoechst dye, Thiazole Orange, Sybr Green, or Oxazole Yellow, that has been modified to include a linker group that is capable of binding (or tethering) the affinity ligand to the surface. The affinity ligand may be a Hoechst dye modified to include a linker group, such as, but not limited to, a spacer ending in an epoxy, carboxy, halide or amino group. The affinity ligand may be a Hoechst dye modified with an alkylamine, such as an as $C_{2-12}$ alkylamine, or $C_{2-8}$ alkylamine, on the left or right side of the compound. The affinity ligand may be Thiazole Orange modified to include a linker group, such as, but not limited to, a spacer ending in an epoxy, carboxy, halide or amino group. The affinity ligand may be Thiazole Orange modified with an alkylamine, such as an as $C_{2-12}$ alkylamine, or $C_{2-8}$ alkylamine. The affinity ligand may be Oxazole Yellow modified to include a linker group, such as, but not limited to, a spacer ending in an epoxy, carboxy, halide or amino group. The affinity ligand may be Oxazole Yellow modified with an alkylamine, such as an as $C_{2-12}$ alkylamine, or $C_{2-8}$ alkylamine. The affinity ligand may be modified methylene blue, such as monocarboxymethylene blue. To create monocarboxymethylene blue, a carboxy group is introduced and added to one side of the methylene blue to act as a tether to attach to the surface.

The affinity ligand may be CDPI$_3$TFP ester, as disclosed at column 12 in U.S. Pat. No. 8,980,855, the contents of which are incorporated by reference herein in entirety:

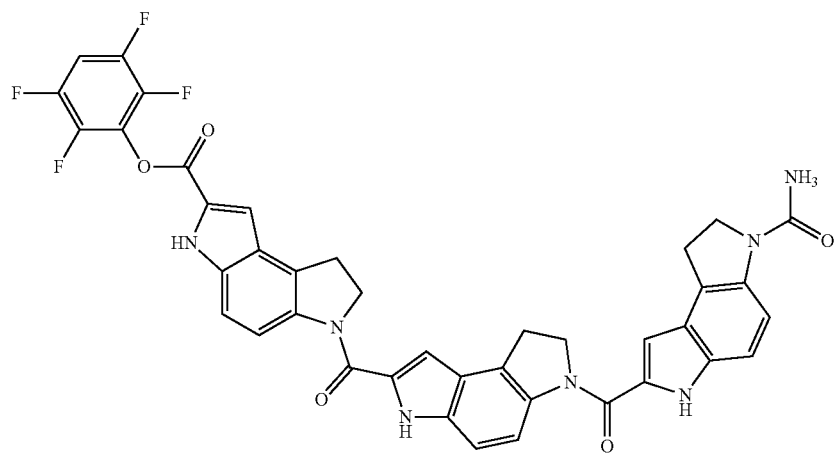 [SMILES: NC(=O)N1CCc2c1ccc1[nH]c(C(=O)N3CCc4c3ccc3[nH]c(C(=O)N5CCc6c5ccc5[nH]c(C(=O)Oc7c(F)c(F)cc(F)c7F)cc65)cc43)cc21]

In this compound, the tetrafluorobenzyl is a reactive carboxy group, which will react, for example, with an amino group on a bead to form an amide bond.

The affinity ligand may be modified Sybr Green I, such as Sybr Green I which has been modified to include an amino group. One means of synthesis for modified Sybr Green I is as follows, in part, as disclosed in U.S. Pat. No. 5,658,751 and U.S. Patent Publication No. 2010/0233710, the contents of which are incorporated by reference herein in their entirety:

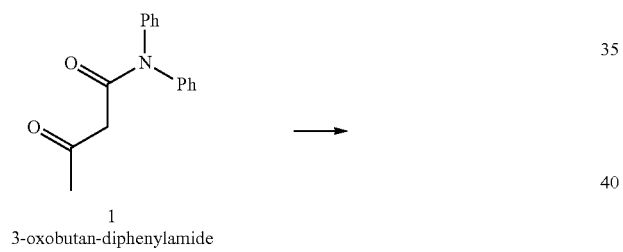

1
3-oxobutan-diphenylamide

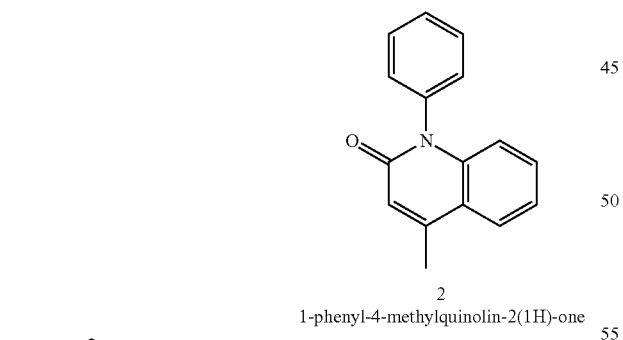

2
1-phenyl-4-methylquinolin-2(1H)-one

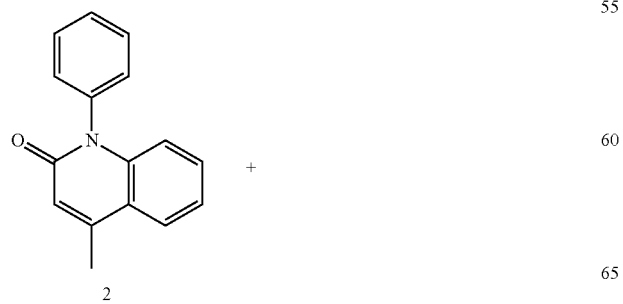

2

-continued

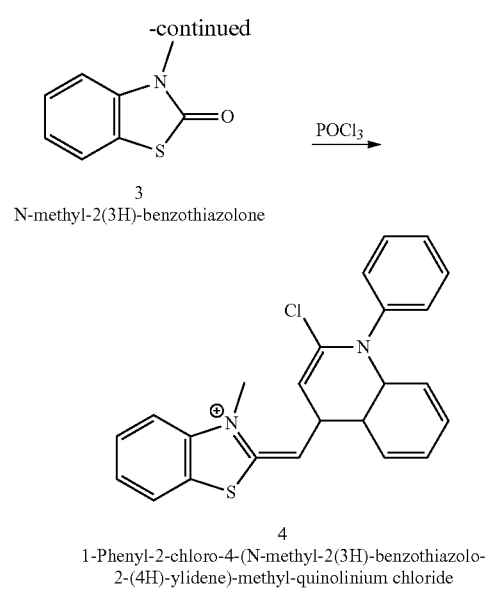

3
N-methyl-2(3H)-benzothiazolone 4
1-Phenyl-2-chloro-4-(N-methyl-2(3H)-benzothiazolo-2-(4H)-ylidene)-methyl-quinolinium chloride

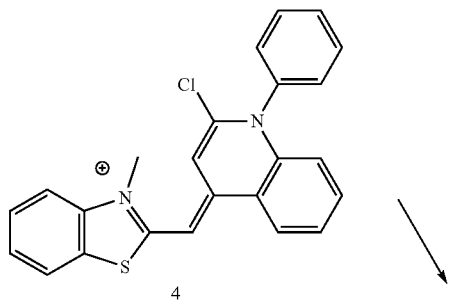

4

-continued

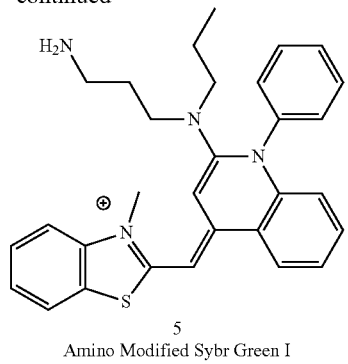

5
Amino Modified Sybr Green I

Here, Sybr Green I has been modified to include an amino group which will permanently and covalently bond to a surface. For example, the amino group will bond to a bead containing an epoxy group or a carboxy group that has been activated by use of NHS ester reagent to allow the carboxy group to react with the amino group to form an amide group.

A C3-amine modified TO (1) or YO (2) utilized in accordance with this disclosure may be made according to the following synthetic scheme:

1-(3-aminopropyl)-4-{[3-methyl-2,3-dihydro-1,3-benzoxazol-2-ylidene]methyl}quinoline-1-ium chloride (2) may also herein be referred to as YO—$C_3$. 1-(3-aminopropyl)-4-{[3-methyl-2,3-dihydro-1,3-benzothiazol-2-ylidene] methyl}quinoline-1-ium chloride (1) may also be herein referred to as TO-$C_3$.

The affinity ligand may be a modified Hoechst dye, which is a compound of the Hoechst bisbenzimide family of dyes where a linker group capable of tethering the affinity ligand (or Hoechst dye in this case) to a surface has been added. The Hoechst dye may be, but is not limited to, Hoechst 33258, Hoechst 33342, or Hoechst 34580, or a mono Hoechst dye (that is, containing one benzimidazole ring as opposed to the usual two benzimidazole ring systems). The modification may be on the right side of the molecule, the left side of the molecule or both. Hoechst 33342 may be modified on the hydroxybezaldehyde side (left side) with $C_2$-amine, $C_3$-amine or $C_4$-amine group. Hoechst 33342 may be modified on the piperazine side (right side) with $C_2$-amine, $C_3$-amine or $C_4$-amine group.

One means of synthesis for modified Hoechst 33342 is as follows, in part, as disclosed in Wiederholt, K., et al., *DNA-Tethered Hoechst Groove-Binding Agent: Duplex Stabilization and Fluorescence Characteristics*, J. Am. Chem. Soc., 1996, 118, 7055-7062:

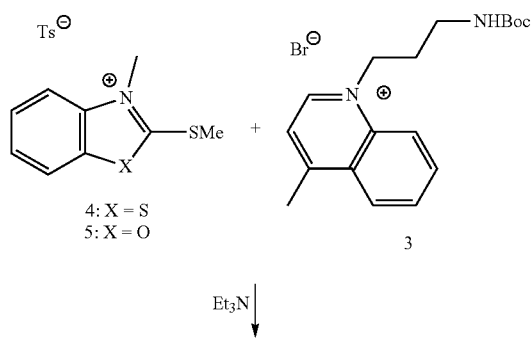

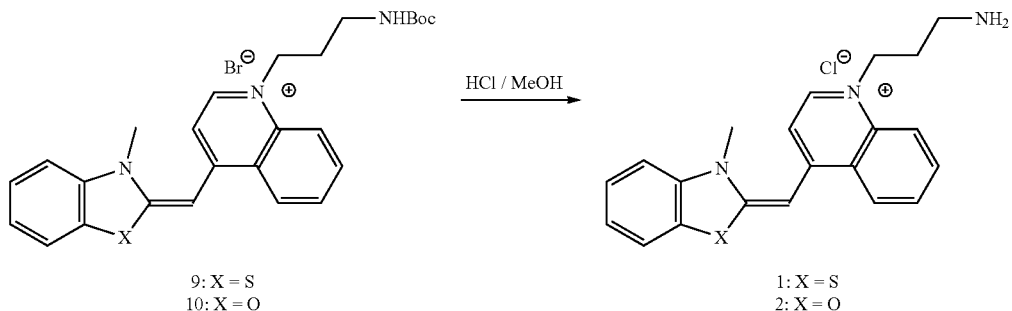

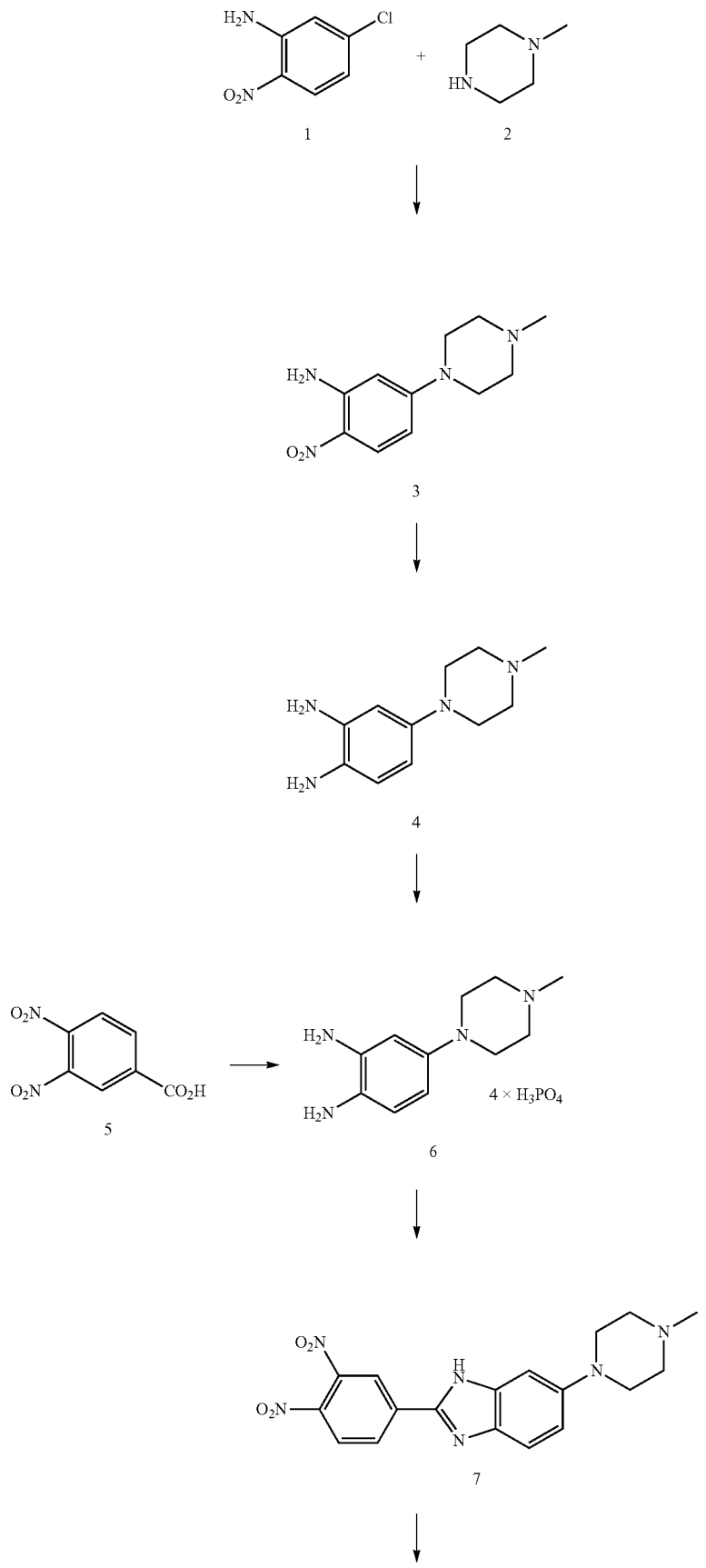

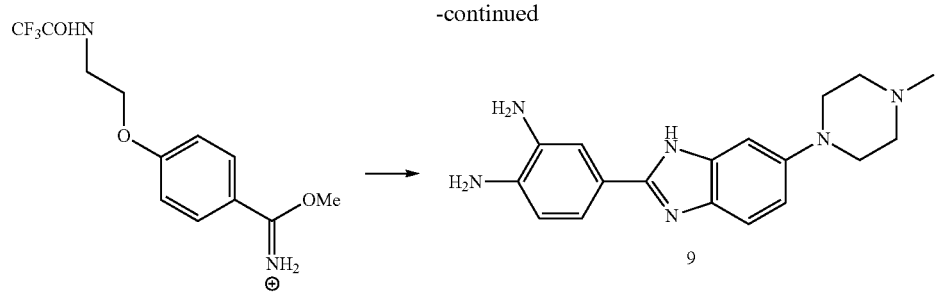

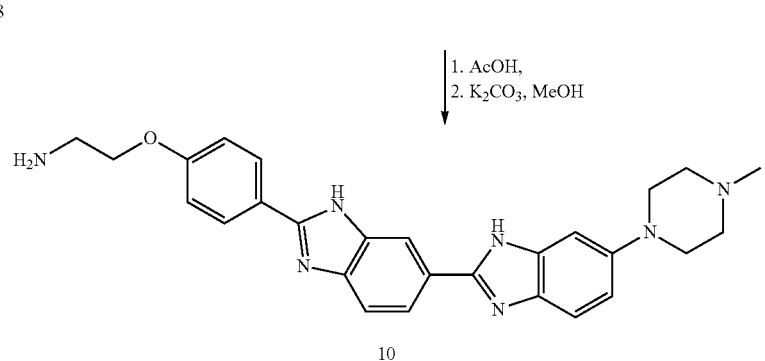

Here, Hoechst 33342 has been modified to include an amino group (on the left side of the molecule) which will permanently and covalently bond to the surface. This compound (10), 3-[4-(5-(4-methyl-1-piperazinyl)-(2,5'-bis-1H-benzimidazol-2-yl]-phenoxy-ethylamine, may also be herein referred to as L-Hoechst-C$_2$. For example, the amino group will bond to a bead containing an epoxy group or a carboxy group that has been activated by use of NHS ester reagent to allow the carboxy group to react with the amino group to form an amide group.

Another modified Hoechst 33342 utilized in accordance with this disclosure is a C$_3$ amine at the hydroxybenzaldehyde side (left side) made, e.g., by the following synthetic scheme:

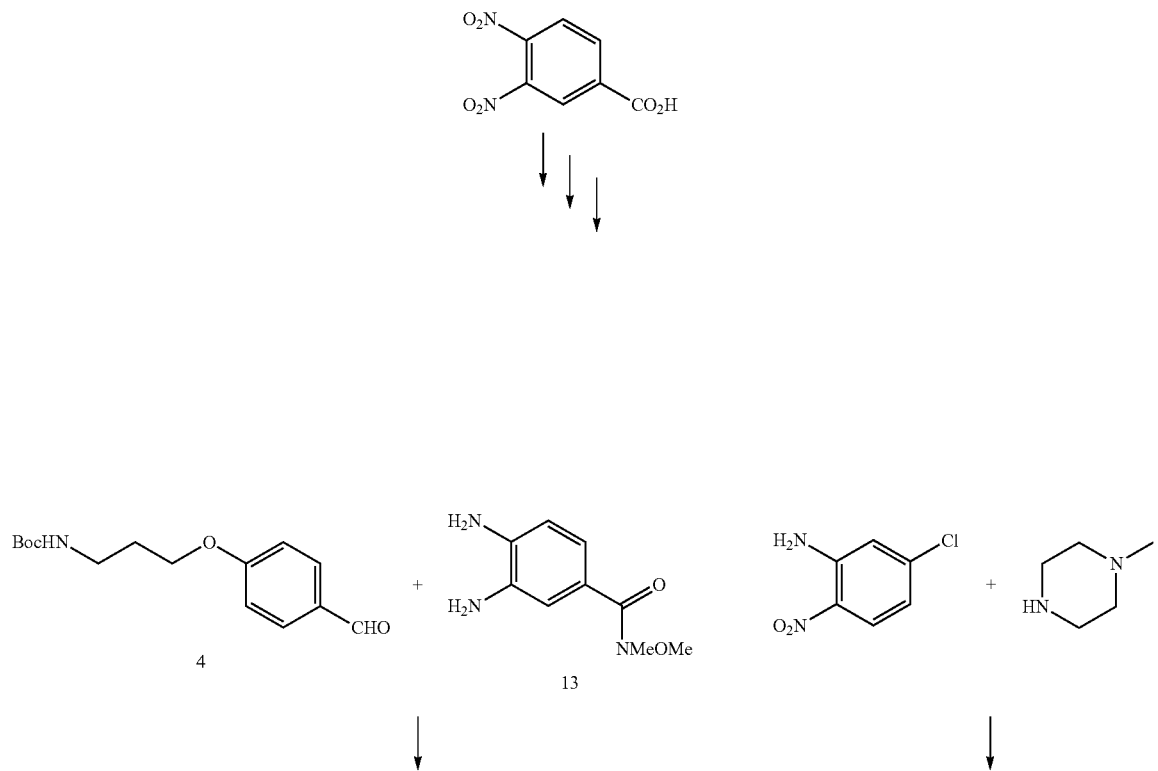

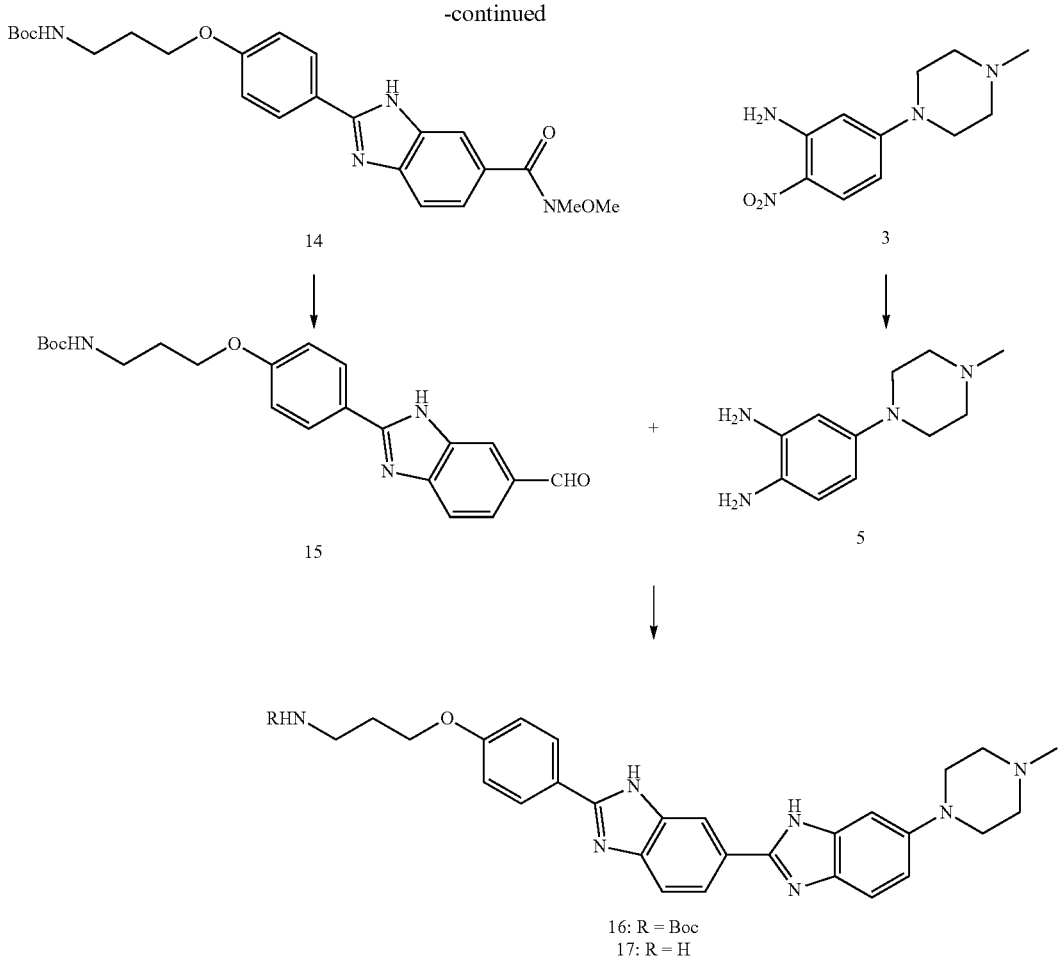
This compound (17), 3-[4-(5-(4-methyl-1-piperazinyl)-(2,5'-bis-1H-benzimidazol-2-yl]-phenoxy-propylamine, may also be herein referred to as L-Hoechst-C$_3$.
Another modified Hoechst 33342 utilized in accordance with this disclosure is a C$_2$ amine at the piperazine side (right side) made, e.g., according to the following synthetic scheme:
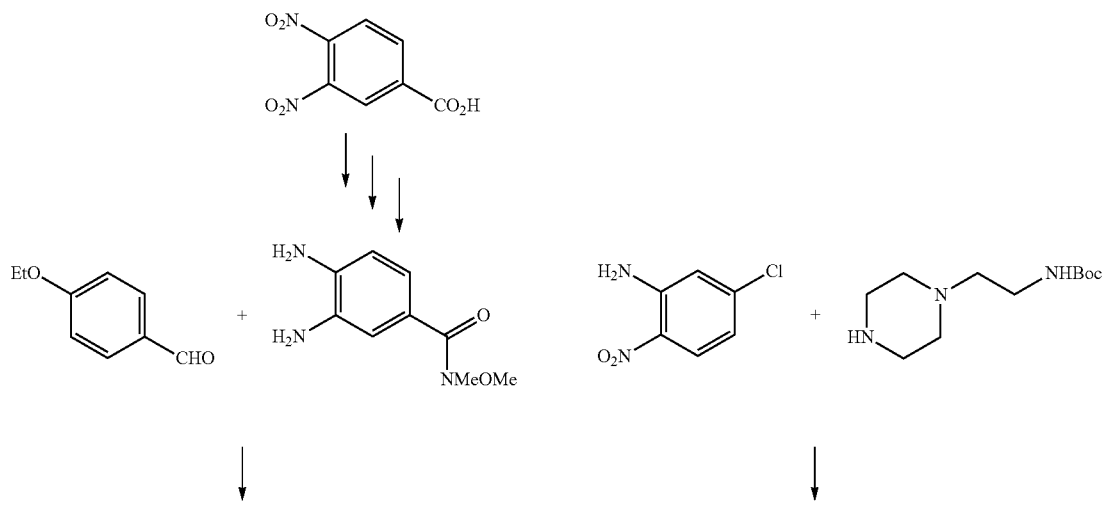

21

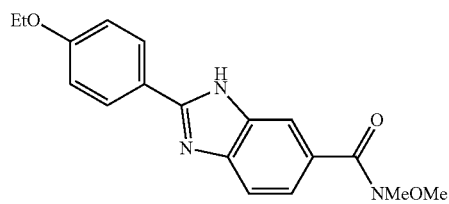

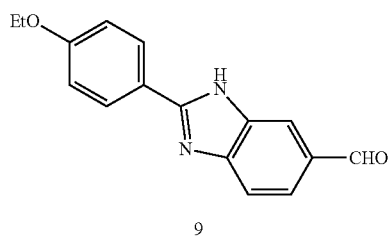

9

↓

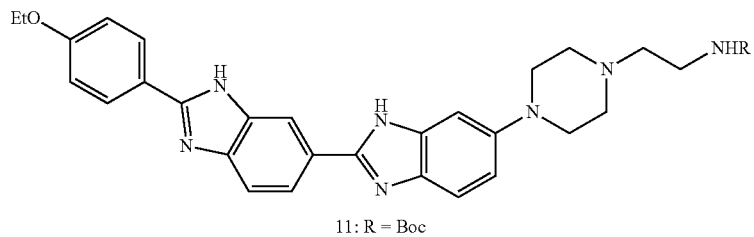

11: R = Boc
12: R = H

This compound (12), 2'-(4-Ethoxyphenyl)-6-(4-amino-ethyl-1-piperazinyl)-2,6'-bis-1H-benzimidazole, may also be herein referred to as R-Hoechst-$C_2$.

A modified mono Hoechst, or mono-imidazole Hoechst, may be modified on the hydroxybezaldehyde side (left side)

-continued

22

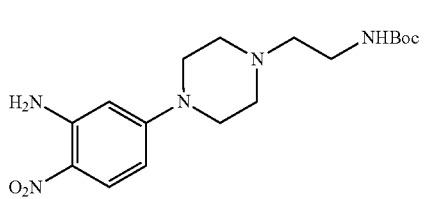

8

↓

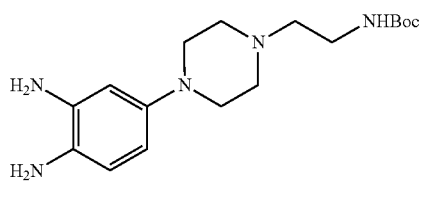

10

↓ with $C_2$-amine, $C_2$-amine or $C_4$-amine group. A modified mono Hoechst utilized in accordance with this disclosure is a $C_3$-amine at the hydroxybezaldehyde side (left side) made, e.g., according to the following synthetic scheme:

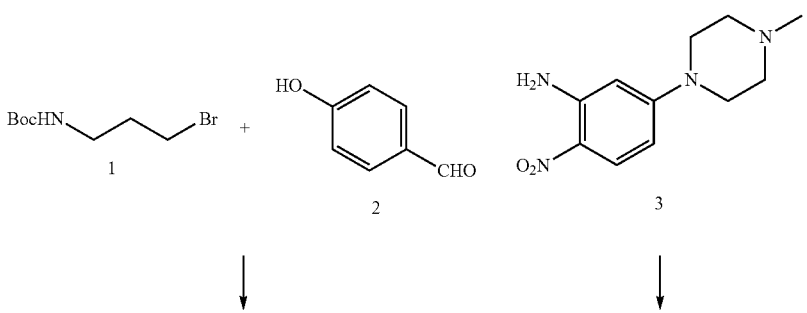

-continued

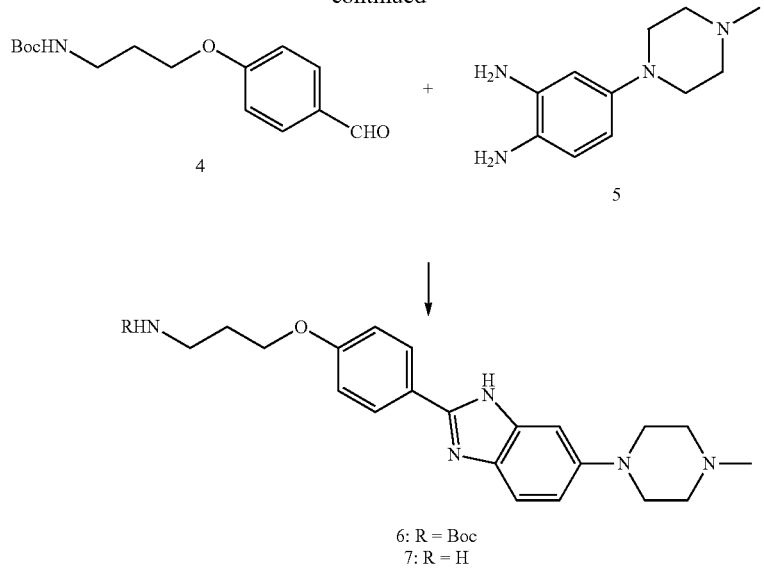

6: R = Boc
7: R = H

This compound (7), 3-[4-(6-(4-methyl-1-piperazinyl)-1H-benzimidazol-2-yl]-phenoxy-propylamine, may also be herein referred to as Mono-Hoechst-$C_3$.

When methylene blue is bound to a bead (such as, e.g., monocarboxymethylene blue bound to an amino-agarose bead), because methylene blue is positively charged, it would be expected that it would bind DNA and also proteins, such as Bovine serum albumin (BSA) (a globular protein). However, it was found that methylene blue works surprisingly well in chromatography for removal of DNA because it was found to bind to DNA but not to the protein. Thereby, the DNA can be removed and isolated from a feed stream without also removing the protein. The DNA may be eluted from the methylene blue and optionally recovered for further testing and/or processing.

When the coupled surface-affinity ligand is modified methylene blue bound to an agarose bead, at least about 60%, at least about 70%, at least about 80%, at least about 90%, or about 70% to about 95% of the target macromolecule in a sample may be bound to the affinity ligand. When the target macromolecule is DNA, modified methylene blue may bind about 70% to about 85% or about 70% to about 80% of the DNA in a sample.

When the coupled surface-affinity ligand is a modified Hoechst dye bound to an agarose bead, at least about 60%, at least about 70%, at least about 80%, at least about 90%, about 70% to about 99%, about 80% to about 99%, about 85% to about 98% of the target macromolecule in a sample may be bound to the affinity ligand. When the target macromolecule is DNA, the modified Hoechst dye may bind about 70% to about 99%, about 80% to about 99%, or about 85% to about 98% of the DNA in a sample. When the target macromolecule is DNA, Mono-Hoechst-$C_{2-6}$, L-Hoechst-$C_{2-6}$ or R-Hoechst-$C_{2-6}$ coupled with a bead or membrane may bind about 70% to about 99%, about 80% to about 99%, or about 85% to about 98% of the DNA in a sample. When the target macromolecule is DNA, Mono-Hoechst-$C_3$, L-Hoechst-$C_3$ or R-Hoechst-$C_3$ coupled with a bead may bind about 70% to about 99%, about 80% to about 99%, or about 85% to about 98% of the DNA in a sample.

When the coupled surface-affinity ligand is a modified Thiazole Orange bound to an agarose bead, at least about 60%, at least about 70%, at least about 80%, at least about 90%, about 60% to about 99%, about 70% to about 99%, about 70% to about 95% of the target macromolecule in a sample may be bound to the affinity ligand. When the target macromolecule is DNA, the modified Thiazole Orange may bind about 60% to about 95%, about 70% to about 90%, or about 75% to about 85% of the DNA in a sample. When the target macromolecule is DNA, TO-$C_2$-8 coupled to a bead or membrane may bind about 60% to about 95%, about 70% to about 90%, or about 75% to about 85% of the DNA in a sample. When the target macromolecule is DNA, TO-$C_3$-6 coupled to a bead may bind about 60% to about 95%, about 70% to about 90%, or about 75% to about 85% of the DNA in a sample.

When the coupled surface-affinity ligand is a modified Oxazole Yellow bound to an agarose bead, at least about 60%, at least about 70%, at least about 80%, at least about 90%, about 60% to about 99%, about 70% to about 99%, about 70% to about 95% of the target macromolecule in a sample may be bound to the affinity ligand. When the target macromolecule is DNA, the modified Oxazole Yellow may bind about 60% to about 98%, about 70% to about 95%, or about 80% to about 95% of the DNA in a sample. When the target macromolecule is DNA, YO—$C_{2-8}$ coupled to a bead or membrane may bind about 60% to about 98%, about 70% to about 95%, or about 80% to about 95% of the DNA in a sample. When the target macromolecule is DNA, YO—$C_3$ coupled to a bead may bind about 60% to about 98%, about 70% to about 95%, about 80% to about 95%, or about 85% to about 95% of the DNA in a sample.

When the affinity ligand couples with the surface, a density, which is the number of affinity ligands per volume of the solid surface (μg/mL), may be calculated. The higher the density, the more affinity ligands are available for binding the target macromolecule. The dye ligand density may range from about 5 μg/mL to about 50 μg/mL, or about 6 μg/mL to about 45 μg/mL.

After making the coupled surface-affinity ligand, it is placed into a container for use in the selected separation process. Any container, such as a column, vessel, vat, bowl, cylinder, conical shaped container, made of any material known for use in the art, such as glass, plastic, or metal, may be used in accordance with the disclosure. The container need only to be selected to work with the process of separation science being implemented.

After the coupled surface-affinity ligand is placed in a container, the method of the disclosure includes introducing a sample, wherein the sample contains the target macromolecule and any other combination of one or more nucleic acids and other contaminants, into the container such that the sample and the coupled surface-affinity ligand come in contact (for example are mixed or combined) causing the coupled surface-affinity ligand to incubate with the sample for a residence time, wherein the target macromolecule binds to the affinity ligand. The affinity ligand is bound to the surface and captures the target macromolecule when a sample or feed stream containing the target macromolecule incubates with the affinity ligand. The sample and affinity ligand must incubate, i.e., remain in contact, for a residence time, which is the amount of time required for the target macromolecule to find and then bind to the affinity ligand. The residence time is greater when the binding reaction is slow, and lower when the binding reaction between the target macromolecule and the affinity ligand is fast. The time needed for the binding to occur is based on the binding kinetics of the coupling and may be different for each coupling, as readily understood in the art. The residence time may be about 0.1 minutes to about 180 minutes, about 0.1 minutes to about 120 minutes, or about 0.1 minutes to about 90 minutes.

After the residence time, the coupled surface-affinity ligand bound to the target macromolecule may be separated from the sample that has the target macromolecule removed therefrom by any means known in the art. For example, when using chromatography, the liquid sample, or eluent, may be drained from the column leaving the solids therein. When using batch chromatography, the sample may be drained or the solid may be removed from the container.

After this separation, the target macromolecule may be eluted from the coupled surface-affinity ligand and recovered for further study and/or processing by any means known in the art. This may be referred to as affinity ligand purification of oligonucleotides (as opposed to removal of contaminants).

After isolation and recovery of the target macromolecule, quantification (i.e., determination of the amount of target macromolecule in the sample) may be performed by any method known in the art.

Another embodiment is a method of isolating and recovering a target macromolecule from a sample containing the target macromolecule and other contaminants, nucleic acids, oligonucleosides, or a combination thereof. The method comprises the steps of: (a) selecting an affinity ligand that will bind to the target macromolecule; (b) binding the affinity ligand to a surface to create a coupled surface-affinity ligand; (c) placing the coupled surface-affinity ligand into a container; (d) introducing the sample containing the target macromolecule to the coupled surface-affinity ligand and causing the coupled surface-affinity ligand to incubate with the sample for a residence time, wherein the target macromolecule binds to the affinity ligand in the container; and (e) separating the remaining sample from the coupled surface-affinity ligand coupled to the target macromolecule (i.e., the solids).

After this separation, the target macromolecule may be eluted from the coupled surface-affinity ligand and recovered for further study and/or processing by any means known in the art. This may be referred to as affinity ligand purification of oligonucleotides (as opposed to removal of contaminants).

Also disclosed is a method for isolating and removing DNA from a sample containing DNA and other nucleic acids or oligonucleotides, comprising the steps of: (a) selecting an affinity ligand that will bind DNA; (b) binding the affinity ligand to a surface to create a coupled surface-affinity ligand; (c) placing the coupled surface-affinity ligand into a container; (d) introducing the sample to the coupled surface-affinity ligand and causing the coupled surface-affinity ligand to incubate with the sample for a residence time, wherein the DNA binds to the affinity ligand; and (e) separating the coupled surface-affinity ligand bound to the DNA from the sample that has the DNA removed therefrom. The DNA may be single-stranded or double-stranded DNA. The method for isolating and removing DNA from a sample may further comprise the step of: eluting and recovering the DNA from the coupled surface-affinity ligand.

Also disclosed is a method for isolating and removing RNA from a sample containing RNA and other nucleic acids or oligonucleotides, comprising the steps of: (a) selecting an affinity ligand that will bind RNA; (b) binding the affinity ligand to a surface to create a coupled surface-affinity ligand; (c) placing the coupled surface-affinity ligand into a container; (d) introducing the sample to the coupled surface-affinity ligand and causing the coupled surface-affinity ligand to incubate with the sample for a residence time, wherein the RNA binds to the affinity ligand; and (e) separating the coupled surface-affinity ligand bound to the RNA from the sample that has the RNA removed therefrom. The RNA may be messenger RNA. It may be single-stranded or double-stranded RNA or messenger RNA. The method for isolating and removing RNA from a sample may further comprise the step of: eluting and recovering the RNA from the coupled surface-affinity ligand.

Another embodiment is a method of isolating and removing double-stranded DNA from a sample containing double-stranded DNA and other nucleic acids, for example, a sample containing both single-stranded and double-stranded DNA by selecting an affinity ligand that preferentially binds double-stranded DNA. The method comprises the steps of: (a) selecting an affinity ligand that will bind to the double-stranded DNA; (b) binding the affinity ligand to a surface to create a coupled surface-affinity ligand; (c) placing the coupled surface-affinity ligand into a container; (d) introducing the sample containing the double-stranded DNA to the coupled surface-affinity ligand and causing the coupled surface-affinity ligand to incubate with the sample for a residence time, wherein the double-stranded DNA binds to the affinity ligand in the container; and (e) separating the remaining sample from the coupled surface-affinity ligand coupled to the double-stranded DNA by any means known in the art.

Another embodiment is a method of isolating and removing double-stranded RNA from a sample containing double-stranded RNA and other nucleic acids, for example, a sample containing both single-stranded and double-stranded RNA by selecting an affinity ligand that preferentially binds double-stranded RNA. The method comprises the steps of: (a) selecting an affinity ligand that will bind to the double-stranded RNA; (b) binding the affinity ligand to a surface to create a coupled surface-affinity ligand; (c) placing the coupled surface-affinity ligand into a container; (d) introducing the sample containing the double-stranded RNA to the coupled surface-affinity ligand and causing the coupled surface-affinity ligand to incubate with the sample for a residence time, wherein the double-stranded RNA binds to the affinity ligand in the container; and (e) separating the remaining sample from the coupled surface-affinity ligand coupled to the double-stranded RNA by any means known in the art.

Another embodiment is a method of isolating and removing single-stranded DNA from a sample containing single-stranded DNA and other nucleic acids, for example, a sample containing both single-stranded and double-stranded DNA by selecting an affinity ligand that preferentially binds single-stranded DNA but not double-stranded DNA. The method comprises the steps of: (a) selecting an affinity ligand that will bind to the single-stranded DNA; (b) binding the affinity ligand to a surface to create a coupled surface-affinity ligand; (c) placing the coupled surface-affinity ligand into a container; (d) introducing the sample containing the single-stranded DNA to the coupled surface-affinity ligand and causing the coupled surface-affinity ligand to incubate with the sample for a residence time, wherein the single-stranded DNA binds to the affinity ligand in the container; and (e) separating the remaining sample from the coupled surface-affinity ligand coupled to the single-stranded DNA by any means known in the art.

Another embodiment is a method of isolating and removing single-stranded RNA from a sample containing single-stranded RNA and other nucleic acids, for example, a sample containing both single-stranded and double-stranded RNA by selecting an affinity ligand that preferentially binds single-stranded RNA but not double-stranded RNA. The method comprises the steps of: (a) selecting an affinity ligand that will bind to the single-stranded RNA; (b) binding the affinity ligand to a surface to create a coupled surface-affinity ligand; (c) placing the coupled surface-affinity ligand into a container; (d) introducing the sample containing the single-stranded RNA to the coupled surface-affinity ligand and causing the coupled surface-affinity ligand to incubate with the sample for a residence time, wherein the single-stranded RNA binds to the affinity ligand in the container; and (e) separating the remaining sample from the coupled surface-affinity ligand coupled to the single-stranded RNA by any means known in the art.

Another embodiment is a method of isolating and removing messenger RNA (double-stranded and/or single-stranded) from a sample containing other types of RNA (double-stranded and/or single-stranded) and/or DNA (double-stranded and/or single-stranded) and/or other nucleic acids by selecting an affinity ligand that preferentially binds messenger RNA but not the other nucleic acids in the sample. The method comprises the steps of: (a) selecting an affinity ligand that will bind to the messenger RNA; (b) binding the affinity ligand to a surface to create a coupled surface-affinity ligand; (c) placing the coupled surface-affinity ligand into a container; (d) introducing the sample containing the messenger RNA to the coupled surface-affinity ligand and causing the coupled surface-affinity ligand to incubate with the sample for a residence time, wherein the messenger RNA binds to the affinity ligand in the container; and (e) separating the remaining sample from the coupled surface-affinity ligand coupled to the messenger RNA by any means known in the art.

The terms used in connection with these embodiments (methods of use) have the same meanings and definitions as discussed above.

The features and advantages of the present invention are more fully shown by the following examples which are provided for purposes of illustration, and are not to be construed as limiting the invention in any way.

EXAMPLES

Example 1

An agarose bead coupled with methylene blue was synthesized and used in radial flow chromatography. When a sample containing a mixture of DNA and proteins was placed in the chromatography column and allowed to sit for the required residence time before flowing through, the agarose beads coupled with methylene blue bound about 80% of the DNA in a sample. Binding interactions were clearly shown with both a small amount of material (100 µL), as well as a scale-up of 1 mL resin, analyzed by FPLC. At the same time, there was no unspecific binding of DNA with the negative controls. The saturation level for DNA with this new designed matrix has yet to be determined. However, a trend could be shown where the level of bound percentage of DNA decreased when DNA concentrations of >310 mg/mL were used. Very small DNA fragments also caused a decrease in the percentage bound of DNA. We attempted to exclude the smallest DNA fragments by ultrafiltration (exclusion of less than 10 kDa), whereupon an improvement was detected.

Next, the agarose beads coupled with monocarboxymethylene blue were incubated with a BSA-solution of 1 mg/mL to determine whether the intercalating dye interacted with proteins. No binding of proteins could be detected either with the methylene blue agarose or the negative controls.

In summary, an agarose-resin coupled with methylene blue was synthesized which was able to bind larger strands of DNA, but did not interact with proteins.

Figure 1B:
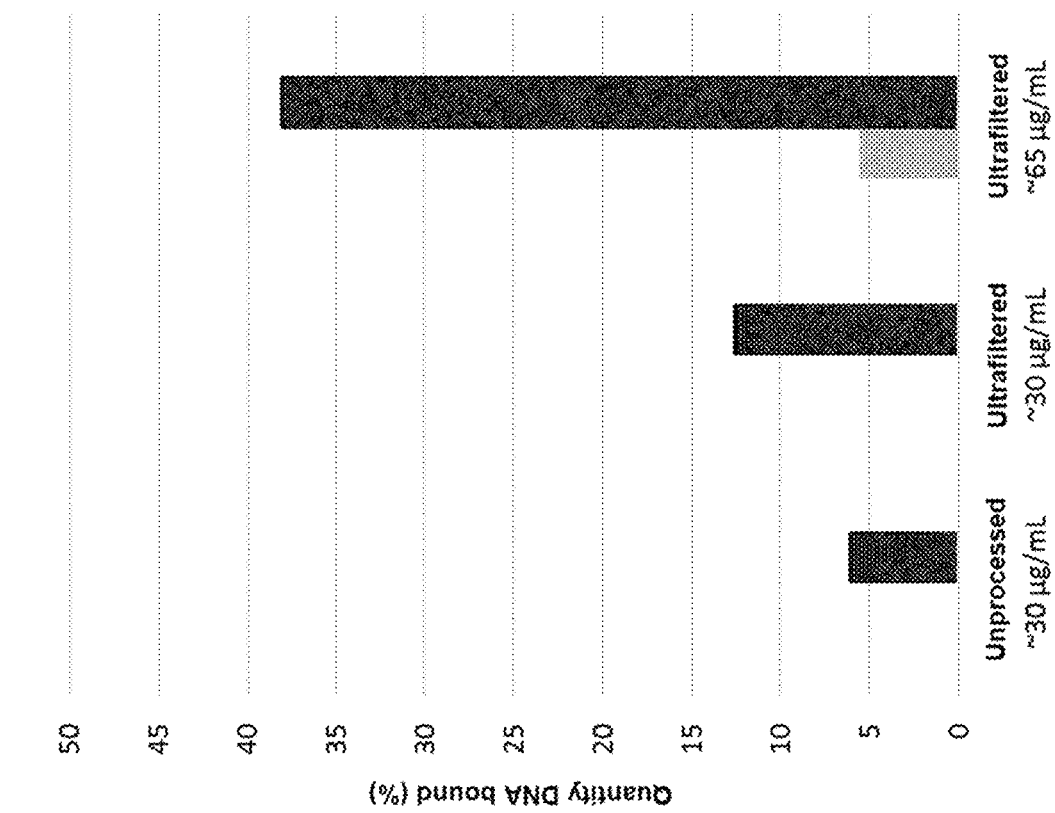

FIGS. 1A and 1B show a comparison of DNA (size <50 bp) unprocessed and "ultrafiltered" in two concentrations of MCMB-beaded agarose gel (30 µg MCMB per mL gel and 65 µg MCMB per mL gel, MCMB=monocarboxymethylene blue): FIG. 1A=% DNA bound to gel of total DNA added, FIG. 1B=Capacity (in µg DNA/mL gel) of gel to bind DNA. Black=MCMB-agarose; Grey=control (no MCMB present on gel).

Figure 2A:
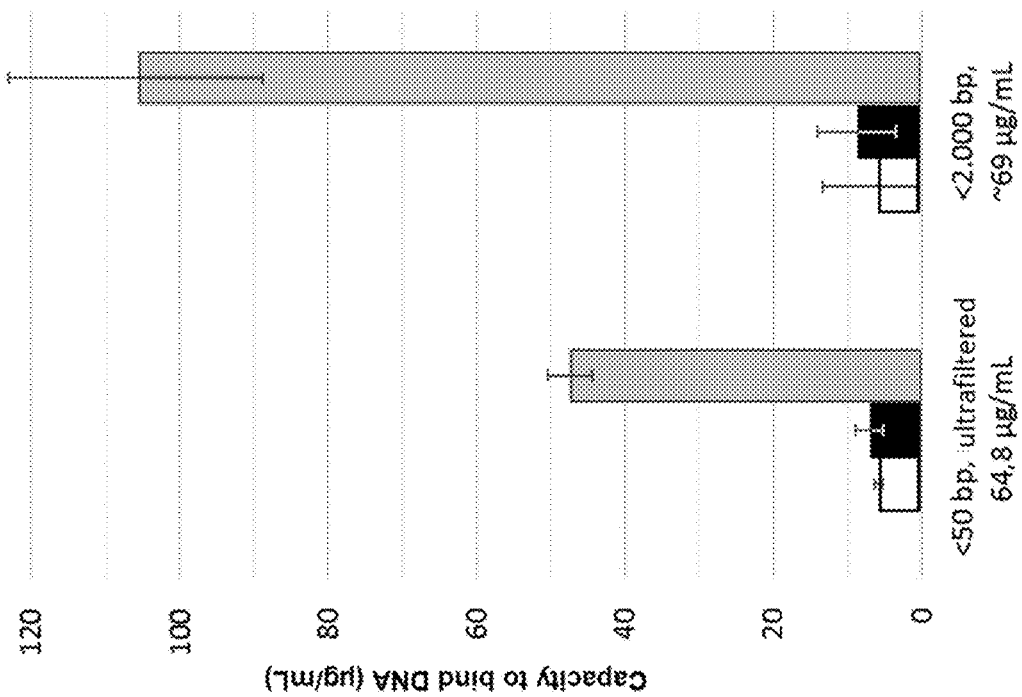
FIGS. 2A and 2B are graphs showing capacity of gel to bind DNA using DNA of different sizes.
Figure 2B:
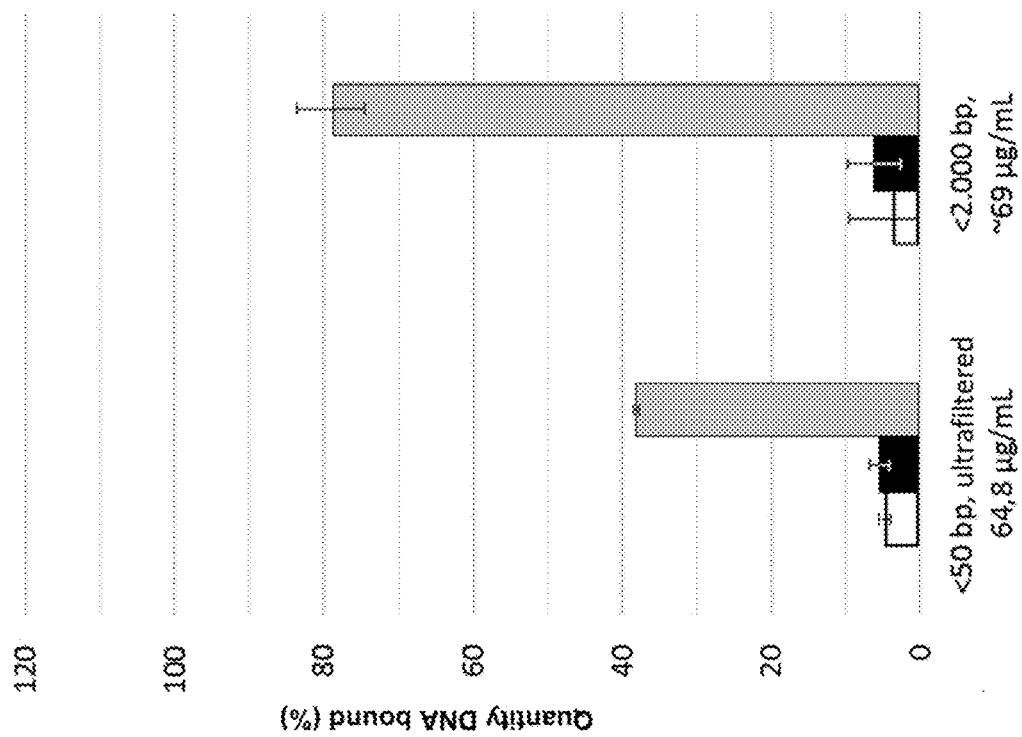
Figure 3A:
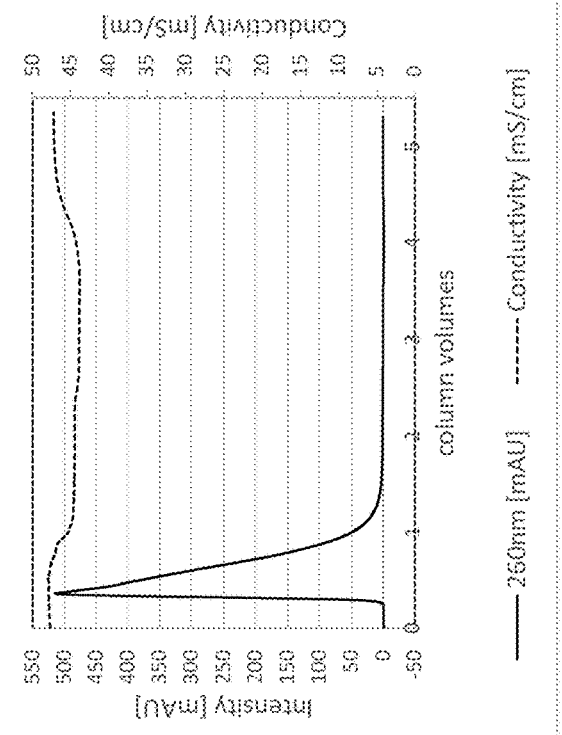
FIGS. 3A-3D are graphs showing peak intensity at 260 nm and conductivity of DNA at different concentrations (each 50 µL) passing through a 1 mL FPLC column packed with native agarose beads. The graphs show the results at four different DNA concentrations.
Figure 3B:
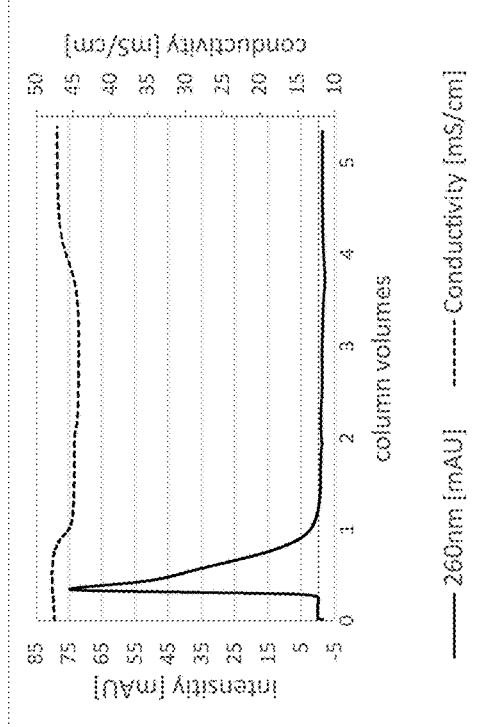
Figure 3C:
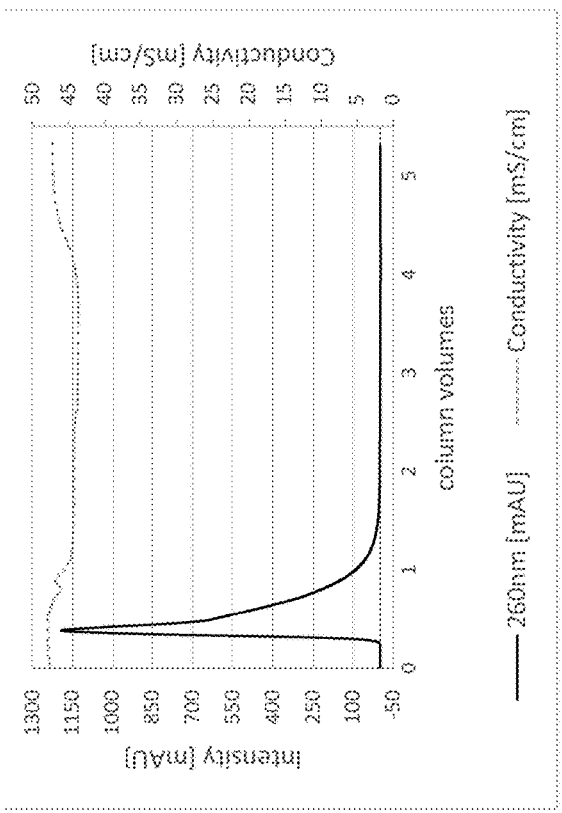
Figure 3D:
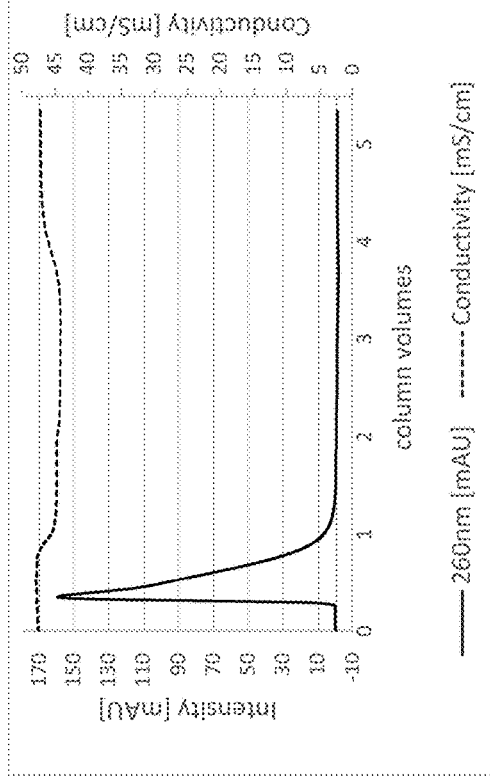

FIGS. 2A and B is a comparison of DNA binding and capacity of gel to bind DNA using DNA of different sizes: FIG. 2A=% DNA bound to gel of total DNA added, FIG. 2B=Capacity (in µg DNA/mL gel) of gel to bind DNA. White=native agarose bead w/o amino groups; Black=amino functionalized agarose beads; Grey=DNA, either at a concentration of <50 bp or <2000 bp. Concentrations given (64.8 and 69) are µg MCMB/mL gel.

FIG. 3A-3D show the results of the control: Abs. 260 nm and conductivity of DNA at different concentrations (each 50 µL) passing through a 1 mL FPLC column packed with native agarose beads. The graphs show that there was no binding for the four different DNA concentrations (3A=3.3 mg/mL, 3B=1.5 mg/mL, 3C=0.33 mg/mL, 3D=0.15 mg/mL) and no linearity with respect to concentration (see peak heights on left hand scale).

Figure 4:
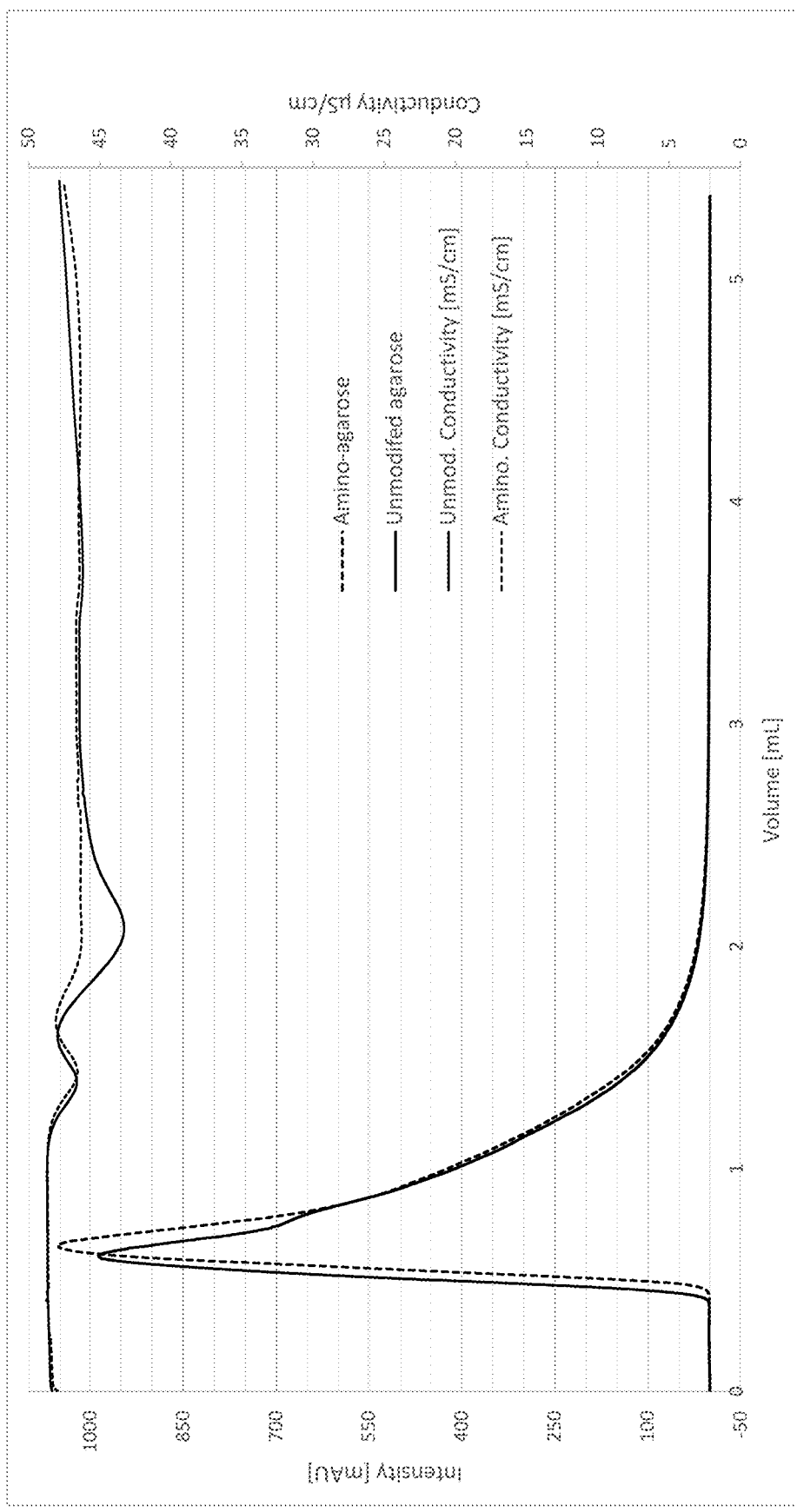
FIG. 4 is a graph showing the results (intensity and conductivity) of loading of DNA (2.5 mg/mL in TRIS, each 50 µL) onto 1 mL FPLC column packed with amino-agarose beads or native unmodified agarose beads.

FIG. 4 is a graph of loading of DNA (2.5 mg/mL in TRIS, each 50 µL) onto 1 mL FPLC column packed with amino-agarose beads (light blue) or native agarose beads (light orange, both left hand scale, Gaussian curves are Abs 260 nm) Upper "straight" curves are conductivity (right hand scale).

Figure 5:
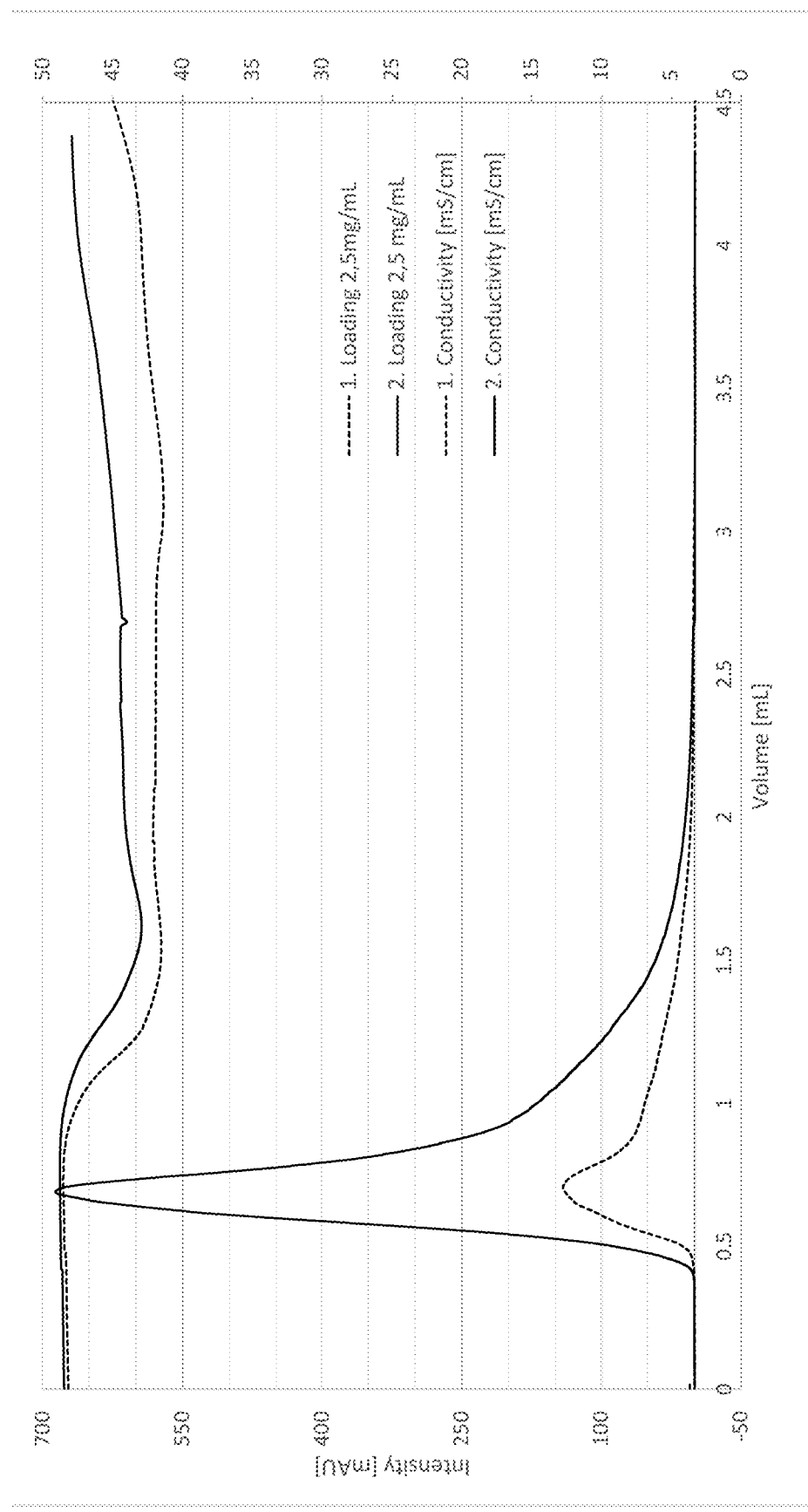
FIG. 5 is a graph showing the results (intensity and conductivity) of loading of DNA (2.5 mg/mL in TRIS, each 50 µL) onto 1 mL FPLC column packed with MCMB agarose beads.

FIG. 5 shows the results of loading of DNA (2.5 mg/mL in TRIS, each 50 µL) onto 1 mL FPLC columns with MCMB agarose beads. First load (solid black) shows markedly reduced DNA passing through column, second load (dashed black) higher due to column being saturated.

Table 1 shows the amount of DNA bound to agarose beads coupled with methylene blue. NK1=amino agarose beads, with 30% DNA binding (presumably ionic interaction), NK2=native agarose beads, essentially no DNA binding. MCMB Agarose beads, upon first loading 88% of DNA in the sample was bound, upon the $2^{nd}$ loading, 50% bound (presumably due to saturation).

TABLE 1

| Column Loading | Peak Area | Percent Bound % |
| --- | --- | --- |
| NK1 First Loading | 417.931 | 30.1 |
| NK1 Second Loading | 376.515 | 37.1 |
| NK2 First Loading | 595.633 | 0.45 |
| NK2 Second Loading | 600.972 | −0.45 |
| MCMB-Agarose First Loading | 73.543 | 87.7 |
| MCMB-Agarose First Loading | 294.937 | 50.7 |

Table 2 shows BSA protein binding to the agarose beads coupled with methylene blue. NK1 Amino-Agarose 3.9% bound, NK2 Native-Agarose 5.5% bound, MCMB-Agarose essentially zero BSA bound, MCMB-Agarose with 42 microgram DNA previously bound 11% BSA bound. There appears to be no interaction of BSA protein with ligand and some ionic binding either with cationic amino groups or anionic DNA. The native agarose binding of 5.5% BSA is thought to be due to a small amount of non-specific interactions with the resin.

TABLE 2

| Resin | BSA mass in sample [µg] | mass bound [µg] | Percent bound | Degree of binding [µg/mL] |
| --- | --- | --- | --- | --- |
| NK1 | 0.208 | 0.008 | 3.9 | 0.07 |
| NK2 (agarose unmodified) | 0.208 | 0.011 | 5.5 | 0.11 |
| MCMB-Agarose | 0.208 | −0.001 | −0.4 | −0.09 |
| MCMB-Agarose loaded with 42 µg DNA | 0.208 | 0.022 | 10.6 | 0.22 |

Example 2: Synthesis of TO-I

Thiazolorange-propyliodide (TO-I) was synthesized as follows:

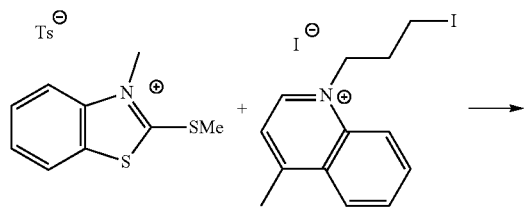

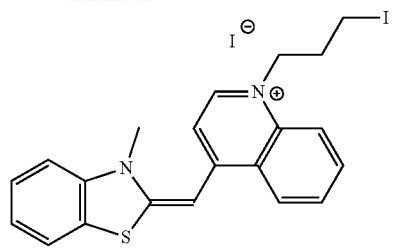

1.84 S-methyl-Benzthioxazole-tosylate (5.0 mmol), was mixed with 2.20 mg Lepidine-iodide (5.0 mmol) and then the mixture was dissolved in 10 ml EtOH. 0.5 ml $Et_3N$ was added and the mixture became immediately red in color becoming dark brownish red. The solution was stirred at 60° C. for 60 min and then left for 12 h at room temp. The resulting fine precipitate was vacuum filtered and dried under vacuum. Total of 1.95 g pure product obtained→67% yield UV (MeOH): $\lambda_{max}$ 506 nm HPLC: Nucleosil 100, C18, 5 µm, MeCN/$H_2O$ (98:2), $R_t$ 18.8 min MALDI: m/z: 459.8 ($C_{21}H_{20}IN_2S^+$)

$^1$H-NMR (DMSO-$d_6$): 2.35 (m, 2H), 3.33 (s, 3H), 3.95 (m, 2H), 4.55 (m, 2H), 6.79 (s, 1H), 7.20 (d, 1H), 7.34 (tr, 1H), 7.53 (tr, 1H), 7.67 (2d, 2H), 7.92 (tr, 1H), 7.96 (d, 1H), 7.90 (tr, 1H), 8.02 (d, 1H), 8.53 (d, 1H), 8.71 (d, 1H).

$^{13}$C-NMR (DMSO-$d_6$): 2.3, 32.5, 33.9, 54.4, 88.2, 107.7, 112.9, 117.6, 122.7, 123.8, 124.0, 124.4, 125.8, 126.6, 128.0, 133.1, 136.8, 140.2, 144.1, 148.2, 159.9.

TO-I was bound to an agarose bead and then used to bind DNA.

Example 3: Synthesis of TO-$C_3$ and YO—$C_3$

Thiazole Orange was modified by introducing a reactive linker, e.g., a linker containing an amino group. After failed attempts of synthesizing TO-$C_3$ through a process that was previously thought to be correct, TO-$C_3$ was synthesized as follows:

TO- and YO—$C_3$-Amines (1) and (2)

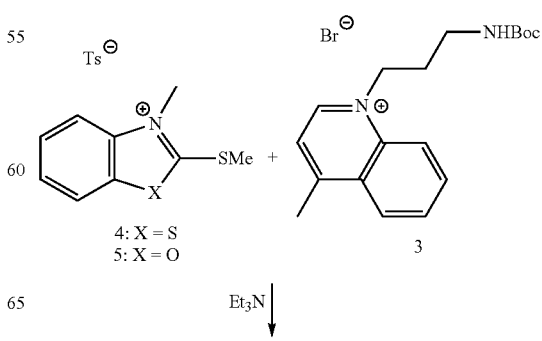

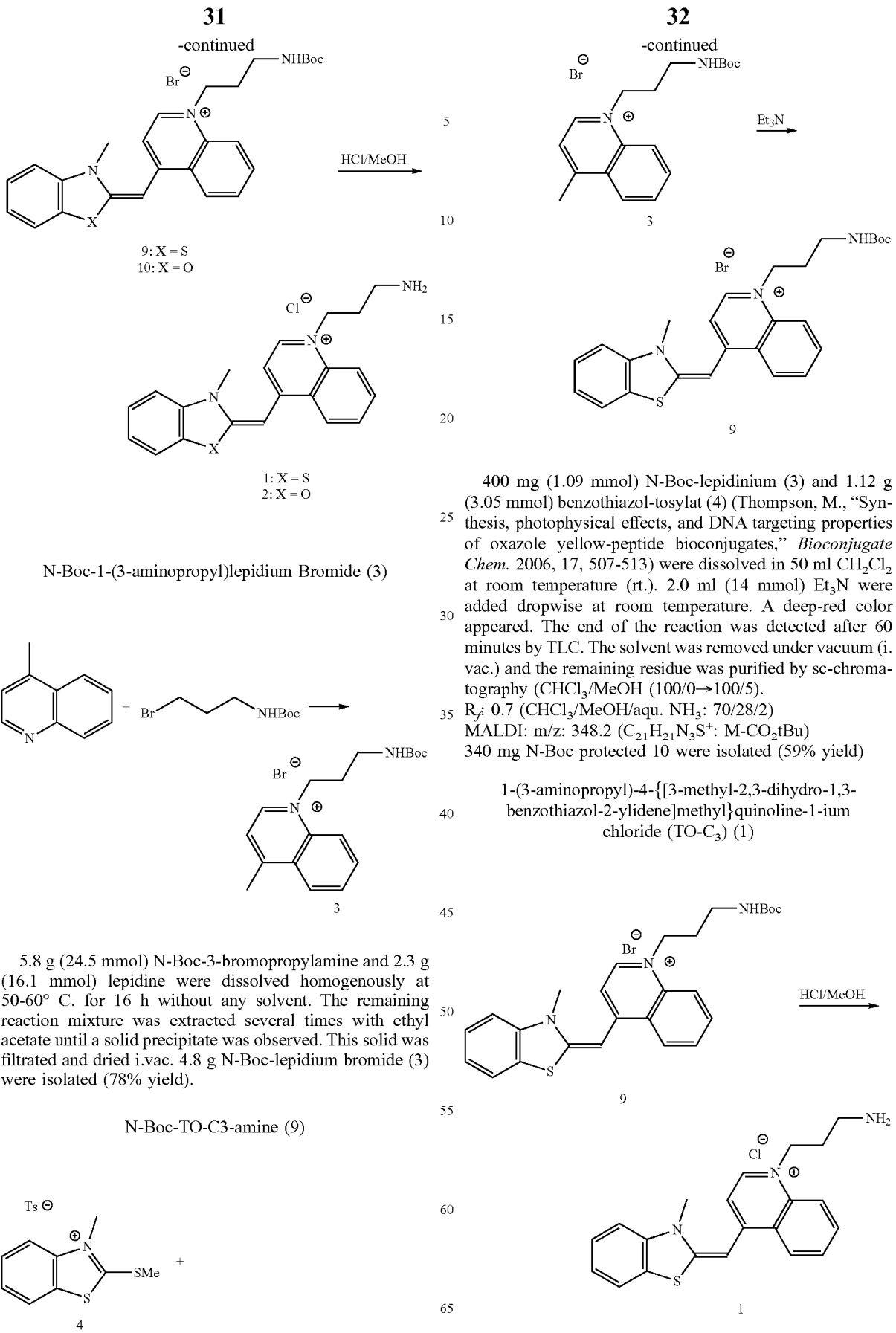

N-Boc-1-(3-aminopropyl)lepidium Bromide (3)

5.8 g (24.5 mmol) N-Boc-3-bromopropylamine and 2.3 g (16.1 mmol) lepidine were dissolved homogenously at 50–60° C. for 16 h without any solvent. The remaining reaction mixture was extracted several times with ethyl acetate until a solid precipitate was observed. This solid was filtrated and dried i.vac. 4.8 g N-Boc-lepidium bromide (3) were isolated (78% yield).

N-Boc-TO-C3-amine (9)

400 mg (1.09 mmol) N-Boc-lepidinium (3) and 1.12 g (3.05 mmol) benzothiazol-tosylat (4) (Thompson, M., "Synthesis, photophysical effects, and DNA targeting properties of oxazole yellow-peptide bioconjugates," *Bioconjugate Chem.* 2006, 17, 507-513) were dissolved in 50 ml $CH_2Cl_2$ at room temperature (rt.). 2.0 ml (14 mmol) $Et_3N$ were added dropwise at room temperature. A deep-red color appeared. The end of the reaction was detected after 60 minutes by TLC. The solvent was removed under vacuum (i. vac.) and the remaining residue was purified by sc-chromatography ($CHCl_3$/MeOH (100/0→100/5).

$R_f$: 0.7 ($CHCl_3$/MeOH/aqu. $NH_3$: 70/28/2)

MALDI: m/z: 348.2 ($C_{21}H_{21}N_3S^+$: M-$CO_2$tBu)

340 mg N-Boc protected 10 were isolated (59% yield)

1-(3-aminopropyl)-4-{[3-methyl-2,3-dihydro-1,3-benzothiazol-2-ylidene]methyl}quinoline-1-ium chloride (TO-C₃) (1)

400 mg (0.76 mmol) N-Boc protected 9 were dissolved in 20 ml abs. MeOH. The clear solution was acidified by HCl/MeOH and allowed to stir for 16 h at rt. The solvent was removed i. vac. The remaining residue was extracted several times with ethyl acetate, filtrated and dried i.vac. 250 mg TO-$C_3$ (1) were isolated (86% yield).

$R_f$: 0.45 (CHCl$_3$/MeOH/aqu. NH$_3$: 70/28/2)

UV (MeOH): $\lambda_{max}$ 506 nm

HPLC: Nucleosil 100, C18, 5 μm, MeCN/H$_2$O (98:2), $R_t$ 11.4 min

MALDI: m/z: 348.2 ($C_2H_{22}N_3S^+$)

$^1$H-NMR (dmso-d$_6$): 2.14 (quint, J=7.2 Hz, 2H), 2.87 (tr, J=7.1 Hz, 2H), 4.03 (s, 3H), 4.73 (tr, J=7.3 Hz, 2H), 6.95 (s, 1H), 7.39 (d, J=7.2 Hz, 1H), 7.43 (tr, J=7.3 Hz, 1H), 7.62 (tr, J=7.1 Hz, 1H), 7.75 (tr, J=7.6 Hz, 1H), 7.81 (d, J=8.3 Hz, 1H), 7.99 (tr, J=8.2 Hz, 1H), 8.06 (d, J=7.2 Hz, 1H), 8.21 (d, J=8.7 Hz, 1H), 8.74 (d, J=6.8 Hz, 1H), 8.81 (d, J=8.1 Hz, 1H).

$^{13}$C-NMR (dmso-d$_6$): 27.0, 33.9, 36.0, 51.2, 88.3, 107.9, 113.1, 118.1, 122.9, 123.9, 124.3, 124.6, 125.9, 126.8, 128.2, 133.3, 137.0, 140.5, 144.2, 148.6, 160.4.

1-(3-aminopropyl)-4-{[3-methyl-2,3-dihydro-1,3-benzoxazol-2-ylidene]methyl}quinoline-1-ium chloride (YO—$C_3$) (2)

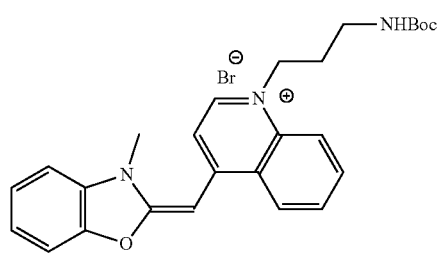

10

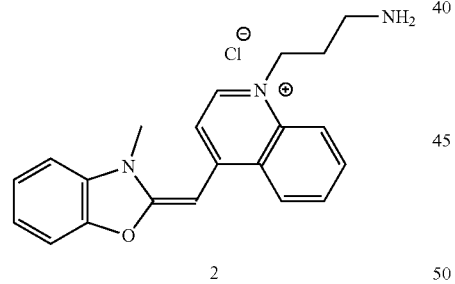

2

400 mg (0.76 mmol) N-Boc protected 10 were dissolved in 20 ml abs. MeOH. The clear solution was acidified by HCl/MeOH and allowed to stir for 16 h at rt. The solvent was removed i. vac. The remaining residue was extracted several times with ethyl acetate, filtrated and dried i.vac. 250 mg TO-$C_3$ (2) were isolated (86% yield).

$R_f$: 0.45 (CHCl$_3$/MeOH/aqu. NH$_3$: 70/28/2)

UV (MeOH): $\lambda_{max}$ 580 nm

HPLC: Nucleosil 100, C18, 5 μm, MeCN/H$_2$O (98:2), $R_t$ 10.7 min

MALDI: m/z: 332.5 ($C_{21}H_{22}N_3O^+$)

$^1$H-NMR (dmso-d$_6$): 2.18 (quint, J=7.3 Hz, 2H), 2.91 (sext, J=6.0 Hz, 2H), 3.87 (s, 3H), 4.74 (tr, J=7.3 Hz, 2H), 6.30 (s, 1H), 7.39 (tr, J=7.8 Hz, 1H), 7.48 (tr, J=7.6 Hz, 1H), 7.64 (d, J=7.9 Hz, 1H), 7.72 (tr, J=7.6 Hz, 1H), 7.81 (d, J=8.0 Hz, 1H), 7.93 (d, J=7.2 Hz, 1H), 7.97 (tr, J=7.2 Hz, 1H), 8.18 (d, J=8.7 Hz, 1H), 8.62 (d, J=7.2 Hz, 1H), 8.78 (d, J=8.4 Hz, 1H).

$^{13}$C-NMR (dmso-d$_6$): 26.8, 30.5, 35.9, 50.9, 74.2, 109.1, 110.7, 110.9, 117.9, 123.4, 124.3, 125.9, 126.2, 126.5, 131.3, 133.3, 137.1, 143.4, 146.1, 150.0, 161.5.

Example 4: Comparative Synthetic Scheme from Prior Art

In the prior art, the authors taught that TO-$C_3$ and YO—$C_3$ could be made according to the synthetic schemes set forth below. With respect to thiazole orange amine 1 (TO-amine 1), one report collected the chemical shifts of the signals of the $^1$H- and $^{13}$C-NMR spectra without giving an assignment (Pham, H. H., et al., "Bichromophoric dyes for wavelength shifting of dye-protein fluoromodules," *Org. Biomol. Chem.* 2015, 13, 3699-3710), while other reports published wrong data for this compound (Brenner, S., et al., "Fluorescent molecular motors," *PCT Int. Appl.* 2014, WO 2014051521, Al 20140403; Fei, X., et al., "Thiazole orange derivatives: synthesis, fluorescence properties, and labeling cancer cells," *Bioorg. Med. Chem.* 009, 17, 585-591; Fei, X., et al., "Solid-phase synthesis and modification of thiazole orange and its derivatives and their spectral properties," *J. Comb. Chem.* 2007, 9, 943-950). Upon performing the experiments, amidine compounds 7 and 8 were made rather than the desired TO-$C_3$ and YO—$C_3$. In this experiment, S-methyl-benzothiazol tosylat (4) is in excess and reacted on the right and left side of the lepidinium bromide.

1-(3{[-3-methyl-2,3-dihydro-1,3-benzothiazol-2-ylidene]amino}propyl)-4-{[3-methyl-2,3-dihydro-1,3-benzothiazol-2-ylidene]methyl}quinoline-1-ium bromide (TO-C3-amidine) (7)

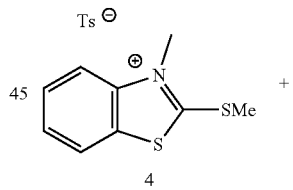

4

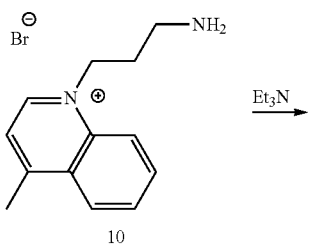

10

-continued

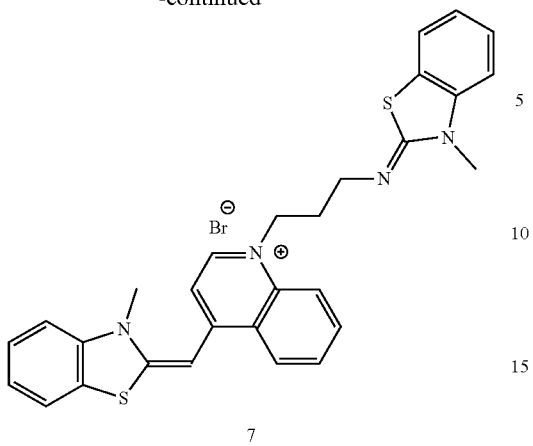

7

1.26 g (3.6 mmol) S-methyl-benzothiazol tosylat (4) (Zhang, T. H.; He, H. X; Du, J. L.; He, Z. J. Yao, S. *Molecules*, 2018, 23, 2011-2024) and 980 mg (3.5 mmol) lepidinium bromide (10) (Gromov, S, P. et al., "Synthesis, Structure, and Properties of Supramolecular Photoswitches Based on Ammonioalkyl Derivatives of Crown Ether Styryl Dyes," *J. Org. Chem.* 2014, 79, 11416-11430) were suspended in 20 ml $CH_2Cl_2$. 2.0 ml (14 mmol) $Et_3N$ were added dropwise. The deep-red reaction mixture was stirred for further 60 minutes. The end of the reaction was detected by TLC. The reaction mixture was extracted with aq. saturated $NH_4Cl$ and $Na_2CO_3$-solution. The organic phase were separated, dried ($Na_2SO_4$), filtrated and the solvent was evaporated i. vac. The remaining residue was purified by crystallization (ethanol). 750 mg TO-$C_3$-amidine 7 were isolated (43% yield).

$R_f$: ($CHCl_3$/MeOH$_{NH3}$: 85/15)
UV (MeOH): $\lambda_{max}$ 506 nm
HPLC: Nucleosil 100, C18, 5 µm, MeCN/$H_2O$ (98:2), $R_t$ 13.8 min
MALDI: m/z: 495.4 ($C_{29}H_{27}N_4S_2^+$)
$^1$H-NMR (DMSO-$d_6$): 2.24 (quint, J=5.9 Hz, 2H), 3.16 (s, 3H), 3.17 (m, 2H), 4.00 (s, 3H), 4.76 (tr, J=6.7 Hz, 2H), 6.86 (tr, J=7.5 Hz, 1H), 6.87 (s, 1H), 6.99 (d, J=7.9 Hz, 1H), 7.10 (dtr, J=1.0, 7.3 Hz, 1H), 7.23 (d, J=7.1 Hz, 1H), 7.41 (tr, J=7.5 Hz), 7.46 (d, J=6.9 Hz, 1H), 7.61 (dtr, J=7.3 Hz, 1H), 7.74 (tr, J=7.5 Hz, 1H), 7.77 (d, J=8.3 Hz, 1H), 7.96 (d, J=8.0 Hz, 1H), 7.99 (tr, J=8.1 Hz, 1H), 8.22 (d, J=8.7 Hz, 1H), 8.31 (s, 1H), 8.59 (d, J=7.2 Hz, 1H), 8.77 (d, J=8.9 Hz, 1H).
$^{13}$C-NMR (DMSO-$d_6$): 29.6, 33.7, 50.7, 53.1, 79.2, 88.0, 107.7, 109.0, 112.9, 118.3, 120.6, 121.2, 122.3, 122.8, 123.9, 124.3, 124.4, 125.7, 126.3, 126.7, 128.1, 133.1, 137.2, 140.4, 140.6, 144.6, 148.5, 154.7, 159.9.

1-(3{[-3-methyl-2,3-dihydro-1,3-benzoxazol-2-ylidene]amino}propyl)-4-{[3-methyl-2,3-dihydro-1,3-benzoxazol-2-ylidene]methyl}quinoline-1-ium Bromide (YO—C3-amidine) (8)

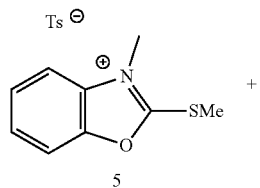

5

+

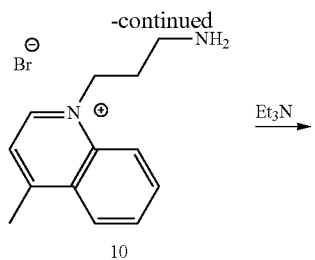

10

$\xrightarrow{Et_3N}$

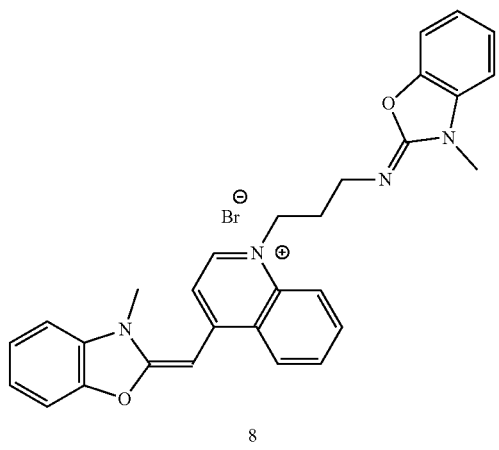

8

1.35 g (3.8 mmol) S-methyl-benzoxazol tosylat (5) (Gromov, S, P. et al., "Synthesis, Structure, and Properties of Supramolecular Photoswitches Based on Ammonioalkyl Derivatives of Crown Ether Styryl Dyes," J. Org. Chem. 2014, 79, pp. 11416-11430) and 980 mg (3.5 mmol) lepidinium bromide (10) were suspended in 20 ml $CH_2Cl_2$. 2.0 ml (14 mmol) $Et_3N$ were added dropwise. The deep-red reaction mixture was stirred for further 60 minutes. The end of the reaction was detected by TLC. The reaction mixture was extracted with aq. saturated $NH_4Cl$ and $Na_2CO_3$-solution. The organic phase were separated, dried ($Na_2SO_4$), filtrated and the solvent was evaporated under vacuum. 750 mg were isolated (36% yield)

$R_f$: ($CHCl_3$/MeOH$_{NH3}$: 85/15)
UV (MeOH): $\lambda_{max}$ 580 nm
HPLC: Nucleosil 100, C18, 5 µm, MeCN/$H_2O$ (98:2), $R_t$ 10.7 min
MALDI: m/z: 331.2 ($C_{21}H_{21}N_3O^+$: M-(N-Me-benzoxazole))
$^1$H-NMR (dmso-$d_6$): 2.13 (quint, J=6.0 Hz, 2H), 3.13 (s, 3H), 3.41 (tr, J=6.0 Hz, 2H) 3.82 (s, 3H), 4.70 (tr, J=6.0 Hz, 2H), 6.82 (m, J=6.0 Hz, 1H), 6.96 (m, J=6.0 Hz, 1H), 7.00 (p, J=6.0 Hz, 1H), 7.17 (p, J=6.0 Hz, 1H), 7.33 (tr, J=6.0 Hz, 1H), 7.43 (tr, J=6.0 Hz, 1H), 7.57 (d, J=7.9 Hz, 1H), 7.67 (tr, J=6.0 Hz, 1H), 7.67 (d, J=6.0 Hz, 1H), 7.73 (d, J=7.2 Hz, 1H), 7.92 (tr, J=6.0 Hz, 1H), 8.14 (d, J=8.7 Hz, 1H), 8.33 (s, 1H), 8.50 (d, J=7.2 Hz, 1H), 8.71 (d, J=8.7 Hz, 1H).
$^{13}$C-NMR (DMSO-$d_6$): 28.3, 29.6, 30.5, 42.2, 52.4, 73.6, 79.2, 107.4 (br), 108.6, 110.5, 110.7, 118.0, 120.3 (br), 123.3, 123.6 (br), 125.8, 126.3, 126.0, 126.3, 131.1, 132.0, 133.1 (br), 137.2, 143.8, 143.8, 145.9, 149.7.3, 161.2.

Example 5: Synthesis of 3-[4-(6-(4-methyl-1-piperazinyl)-1H-benzimidazol-2-yl]-phenoxy-propylamine(Mono-Hoechst-$C_3$)

$R_f$: ~0.5 ($CHCl_3$/ethyl acetate: 88/12)
$C_{15}H_{21}NO_4$ (279.3)
MS-ESI: 280 (M+1), 265 (M-$CH_3$), 223 (M-tBu),

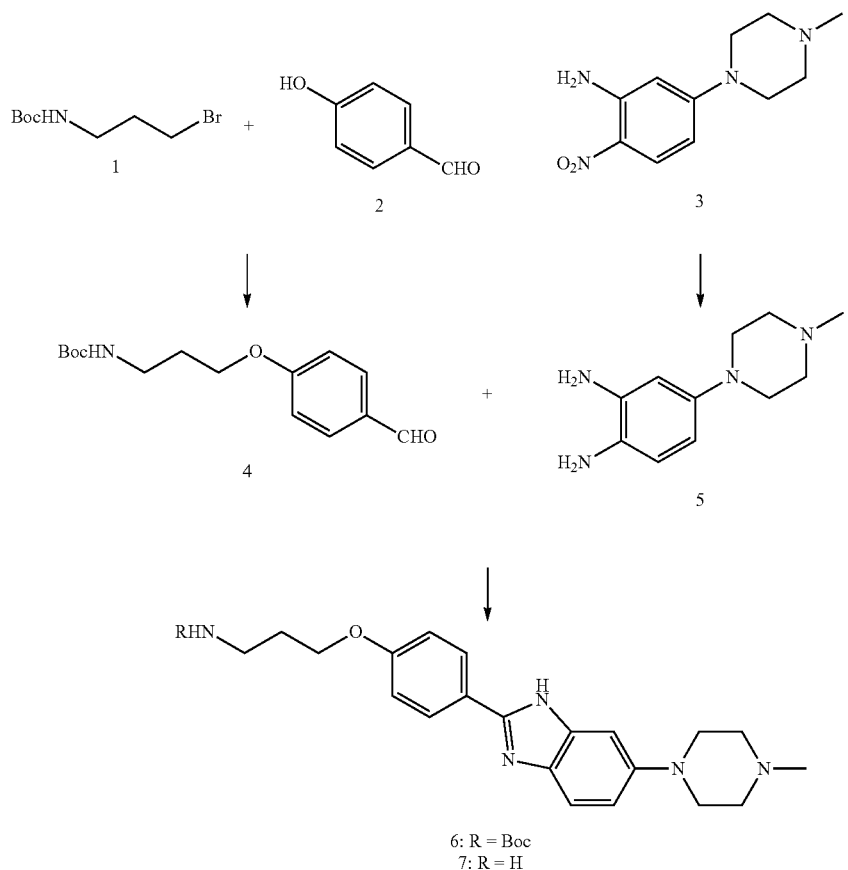

N-Boc-(4-formylphenoxy) propylamine (4)

(Liu, Y., et al., "A "Double-Locked" and enzyme-activated molecular probe for accurate bioimaging and hepatopathy differentiation," *Chemical Science* 2019, 10(47), 10931-10936.)

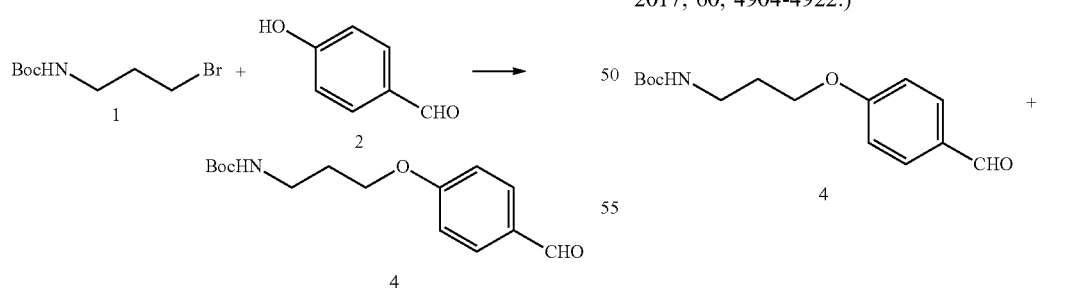

960 mg (11.7 mmol) 4-hydroxyaldehyde 2, 2.52 g (8 mmol) $K_2CO_3$ and 2.36 g (10.0 mmol) N-Boc-3-bromopropyl amine 1 were heated in 3 ml dry DMF for 16 h. The reaction mixture was diluted with 100 ml ethyl acetate and extracted 2-3 times with saturated NaCl-solution. The organic phase were separated, dried ($Na_2SO_4$), filtrated and evaporated i.vac. 2.47 g of N-Boc-protected aldehyde 4 were isolated (88% yield).

N-Boc-3-(4-(6-(4-Methylpiperazin-1-yl)-1H-benzo[d]imidazol-2-yl)-phenoxy)propyl-1-amine (6)

((Ranjan, N., et al., "Selective Inhibition of *Escherichia coli* RNA and DNA Topoisomerase I by Hoechst 33258 Derived Mono- and Bisbenzimidazoles," *J. Med. Chem.* 2017, 60, 4904-4922.)

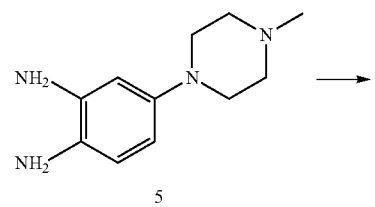

-continued

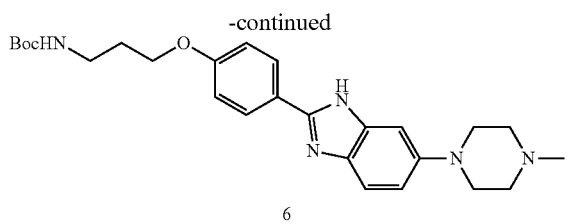

6

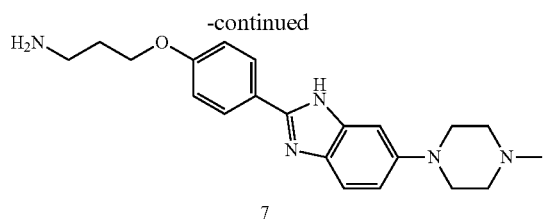

7

385 g (2.0 mmol) Na$_2$S$_2$O$_5$ were dissolved in 2 ml H$_2$O and 1.06 g (3.8 mmol) N-Boc-protected aldehyde 4 in 5 ml EtOH were added to this aqueous solution. A yellow-grey precipitate was observed. A solution of 620 mg (3 mmol) piperazinyl diamine 5 in 50 ml EtOH were added to the aldehyde suspension. The orange-brown suspension was heated at 60° C. for 1-2 h. The completion of reaction was detected by TLC.

R$_f$: ~(CHCl$_3$/MeOH/aqu. NH$_3$: 80/16/4)
UV: $\lambda_{max}$ 326 nm, $\lambda_{max}$ 272 nm.
HPLC: Luna 3μ, Phenyl-Hexyl, MeCN/H$_2$O (98:2), R$_t$ 11.8 min
C$_{26}$H$_{35}$N$_5$O$_3$ (465.6)
MS-MALDI: 466.7 (M+1), 443 (M-43 (NC$_2$H$_5$))

3-(4-(6-(4-Methylpiperazin-1-yl)-H-benzo[d]imidazol-2-yl)-phenoxy)propyl-1-amine (7)

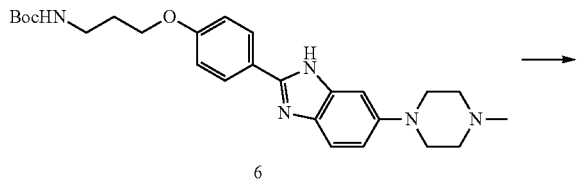

6

930 mg N-Boc-protected benzimidazole 6 (2 mmol) were dissolved in 10 ml MeOH. This solution was acidified by HCL/MeOH. After 24 hours at room temperature, a full deprotection was detected by TLC. The Mono-Hoechst-C$_3$ 7 crystallized from the reaction mixture. 400 mg were isolated by filtration (55% yield).

UV: $\lambda_{max}$ 326 nm, $\lambda_{max}$ 272 nm
HPLC: Luna 3μ, Phenyl-Hexyl, MeCN/H$_2$O (98:2), R$_t$ 3.1 min C$_{21}$H$_{27}$N$_5$O (365.5)
MS-MALDI: 366.1 (M+1), 309 (M-57(NC$_3$H$_7$))
$^1$H-NMR (dmso-d$_6$): 2.09 (quint, J=Hz, 2H), 2.30 (s, 3H), 2.60 (m, 4H), 2.95 (tr, J=Hz, 2H), 3.16 (m, 4H), 4.15 (tr, J=Hz, 2H), 6.91 (m, 2H), 7.07 (d, J=Hz, 2H), 7.42 (m, J=Hz, 1H), 8.11 (d, J=Hz, 2H).
$^{13}$C-NMR (DMSO-d$_6$):

Example 6: Synthesis 2'-(4-Ethoxyphenyl)-6-(4-aminoethyl-1-piperazinyl)-2,6'-bis-1H-benzimidazole (R-Hoechst-C$_2$)

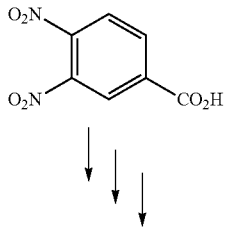

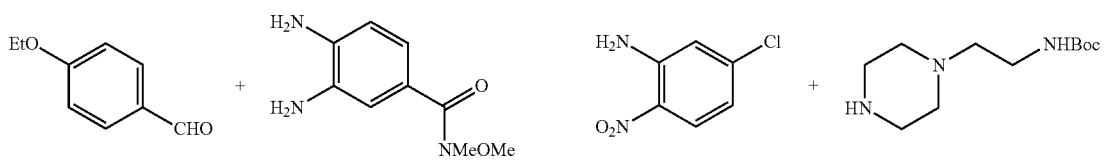

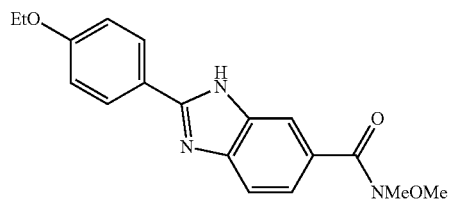

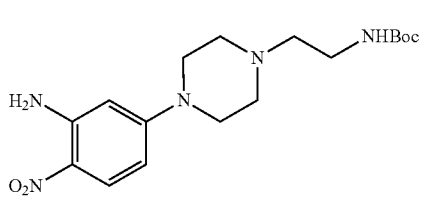

↓ ↓

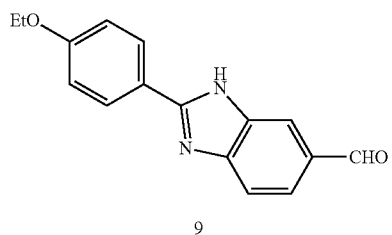  +  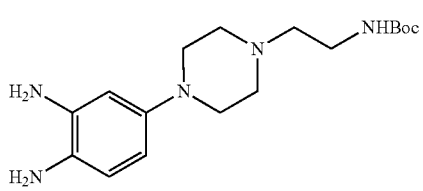

9    10

↓

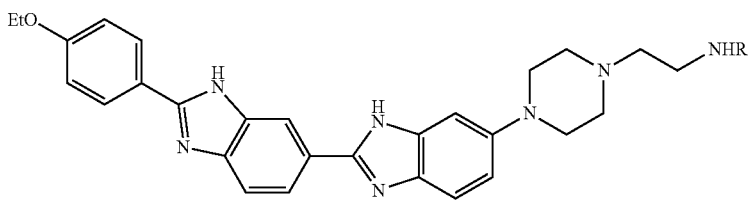

11: R = Boc
12: R = H

5-[4-(2-N-Boc-aminoethyl)piperazinyl)]-2-nitroanilin (8)

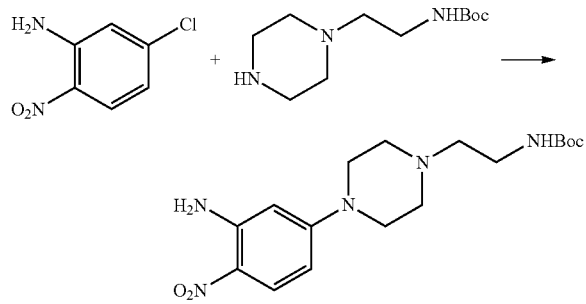

2.0 g (11.6 mmol) 5-chloro-2-nitroaniline, 2.0 g (14.4 mmol) $K_2CO_3$ and 4.0 g (17.5 mmol) 1-(2-N-Boc-aminoethyl)piperazine were suspended in 2.0 ml dry DMF. This suspension was stirred at 140-150° C. for 24 h. The cooled reaction mixture was solved in 100 ml ethyl acetate and extracted 3 times with a saturated NaCl-solution. The organic phase were separated, dried ($Na_2SO_4$), filtrated and evaporated i. vac. The remaining residue was purified by sc-chromatography (MeOH/$CHCl_3$: 1/9). 4.12 g N-Boc-protected 2-nitroaniline 8 were isolated (97% yield).

HPLC: Luna 3μ, Phenyl-Hexyl, MeCN/$H_2O$ (98:2), $R_t$ 15.3 min $C_{17}H_{27}N_5O_4$ (365.2)

MS-MALDI: 366.1 (M), 350.2 (M-Me), 310 (M-$C_4H_8$)

(N-Boc-aminoethyl)-Hoechst 33342 (11)

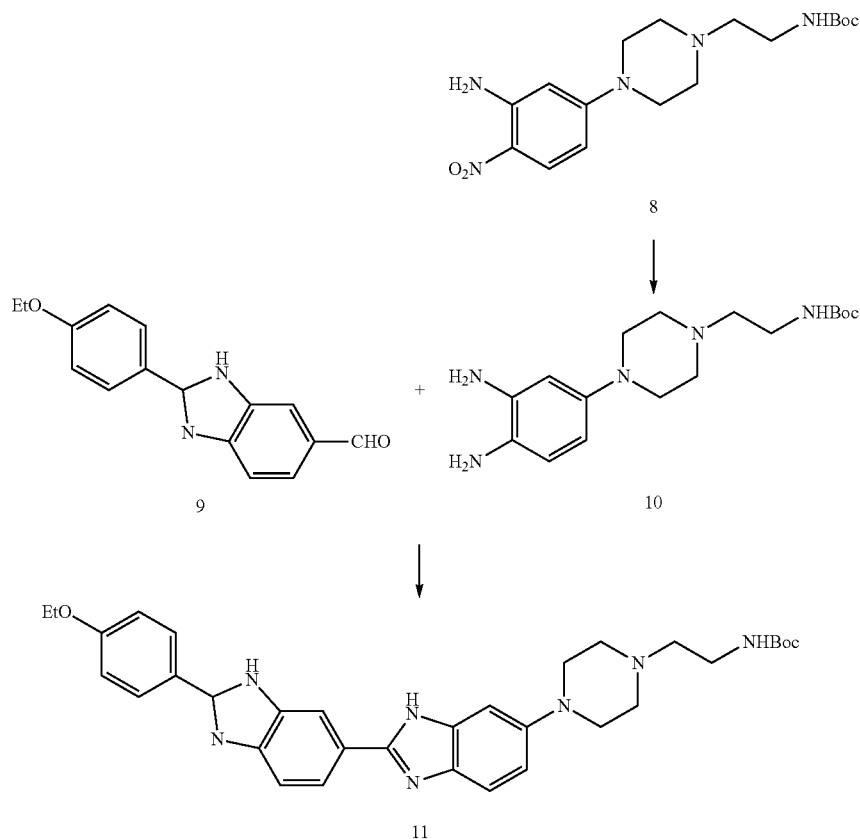

3.0 g (8.2 mmol) N-Boc-protected 2-nitroaniline 8 were dissolved in 160 ml ethanol and 0.7 g of 10% Pd/C were added. The mixture was stirred under a hydrogen atmosphere for 5-6 h. The full completion of the reduction is observed by TLC. After filtration of the catalyst (celite) the solution of the N-Boc protected diamine 10 was used immediately without any further purification.

Simultaneously a solution of 3.2 g (12 mmol) Hoechst aldehyde 9 (Nimesh, H. al., "Synthesis and Biological Evaluation of Novel Bisbenzimidazoles as *Escherichia coli* Topoisomerase IA Inhibitors and Potential Antibacterial Agents," *J. Med. Chem.* 2014, 57, 5238-5257; Chandrika, N. T. et al., "Synthesis and Investigation of Novel Benzimidazole Derivatives as Antifungal Agents," S. *Bioorg. Med. Chem.* 2016, 24, 3680-3686) in 75 ml ethanol was added to a solution of 1.23 g (6.5 mmol) $Na_2S_2O_5$ in 3.0 ml $H_2O$. A white/grey precipitate occurs.

The crude reduction mixture of diamine 10 was added to this suspension. The resulting orange-brown suspension was heated to 70° C. for 2 h. DC-control indicates complete conversion of the N-protected diamine 10. Celite was added and the solvent was evaporated under vacuum. The solid residue was purified by sc-chromatography.

Gradient ethyl acetate/MeOH (100/0-80/20). 4.76 g of N-Boc protected Hoechst 11 were isolated (100% yield) $R_f$ ~0.5 (ethyl acetate/MeOH/aqu. $NH_3$: 70/28/2)
HPLC: Luna 3μ, Phenyl-Hexyl, $MeCN/H_2O$ (98:2), $R_t$ 14.4 min $C_{33}H_{39}N_7O_3$ (581.7)
MS-MALDI: 582.1 (M), 451.7 (M-BocHN—$CH_2$)

2'-(4-Ethoxyphenyl)-6-(4-aminoethyl-1-piperazinyl)-2,6'-bis-1H-benzimidazole (12)

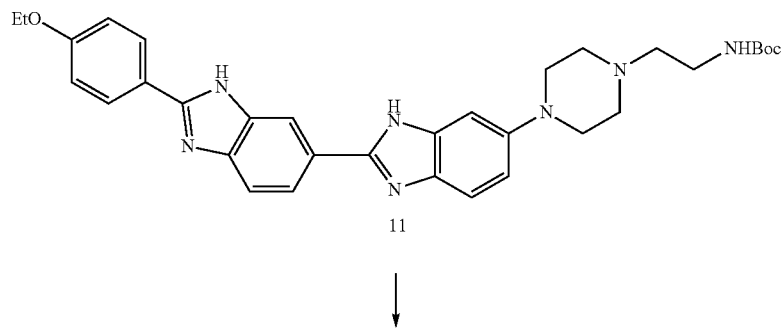

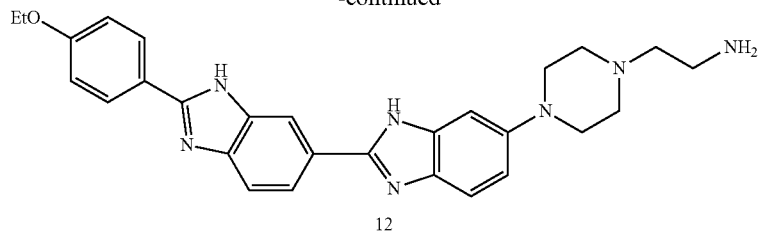

2.0 N-Boc protected Hoechst amine 11 (3.44 mmol) were dissolved in 20 ml EtOH and acidified with HCl/MeOH. After 24 hours at room temperature, the resulting precipitate was filtered and dried. 1.91 g, Hoechst amine 12-3 HCl were isolated (94%).

$R_f$:
~0.5 (ethyl acetate/MeOH/aqu. $NH_3$: 40/50/10) silica gel
~0.5 ($CHCl_3$/MeOH/aqu. $NH_3$: 70/22/8) silica gel
~0.8 ($CHCl_3$/MeOH/aqu. $NH_3$: 70/22/8) $Al_2O_3$
HPLC: Luna 3μ, Phenyl-Hexyl, MeCN/$H_2O$ (98:2), $R_t$ 11.8 min $C_{28}H_{31}N_7O$ (481.6)
MS-MALDI: 482.7 (M+1), 451.5 (M-(N—$CH_2$))

$^1$H-NMR (DMSO-$d_6$): 1.37 (tr, J=7.0 Hz, 3H), 3.26 (m, 4H), 3.38 (q, J=7.0 Hz, 1H), 3.42 (q, J=7.0 Hz, 1H), 3.48 (tr, J=7.0 Hz, 1H), 3.66 (d, J=7.0 Hz, 1H), 3.90 (d, J=7.0 Hz, 1H), 3.92 (m, 1H), 4.17 (q, J=7.0 Hz, 1H), 7.21 (d, J=8.8 Hz, 2H), 7.22 (m, 1H), 7.36 (ddd, J=2.1, 5.8, 8.4 Hz, 1H), 7.72 (dd, 3.5, 5.5 Hz, 1H), 7.97 (d, J=8.5 Hz, 1H), 8.37 (m, 1H), 8.38 (d, J=8.7 Hz, 2H), 8.76 (s, 1H).
$^{13}$C-NMR (DMSO-$d_6$): 15.0, 33.9, 46.5, 51.3, 51.7, 53.3, 55.5, 64.2, 99.3, 99.5, 114.9, 115.8, 117.6, 124.1, 127.0, 130.4, 133.7, 138.2, 148.5, 149.0, 149.1, 153.2, 162.5.

Example 7: Synthesis of 3-[4-(5-(4-methyl-1-piperazinyl)-(2,5'-bis-1H-benzimidazol-2-yl]-phenoxypropylamine (L-Hoechst-$C_3$)

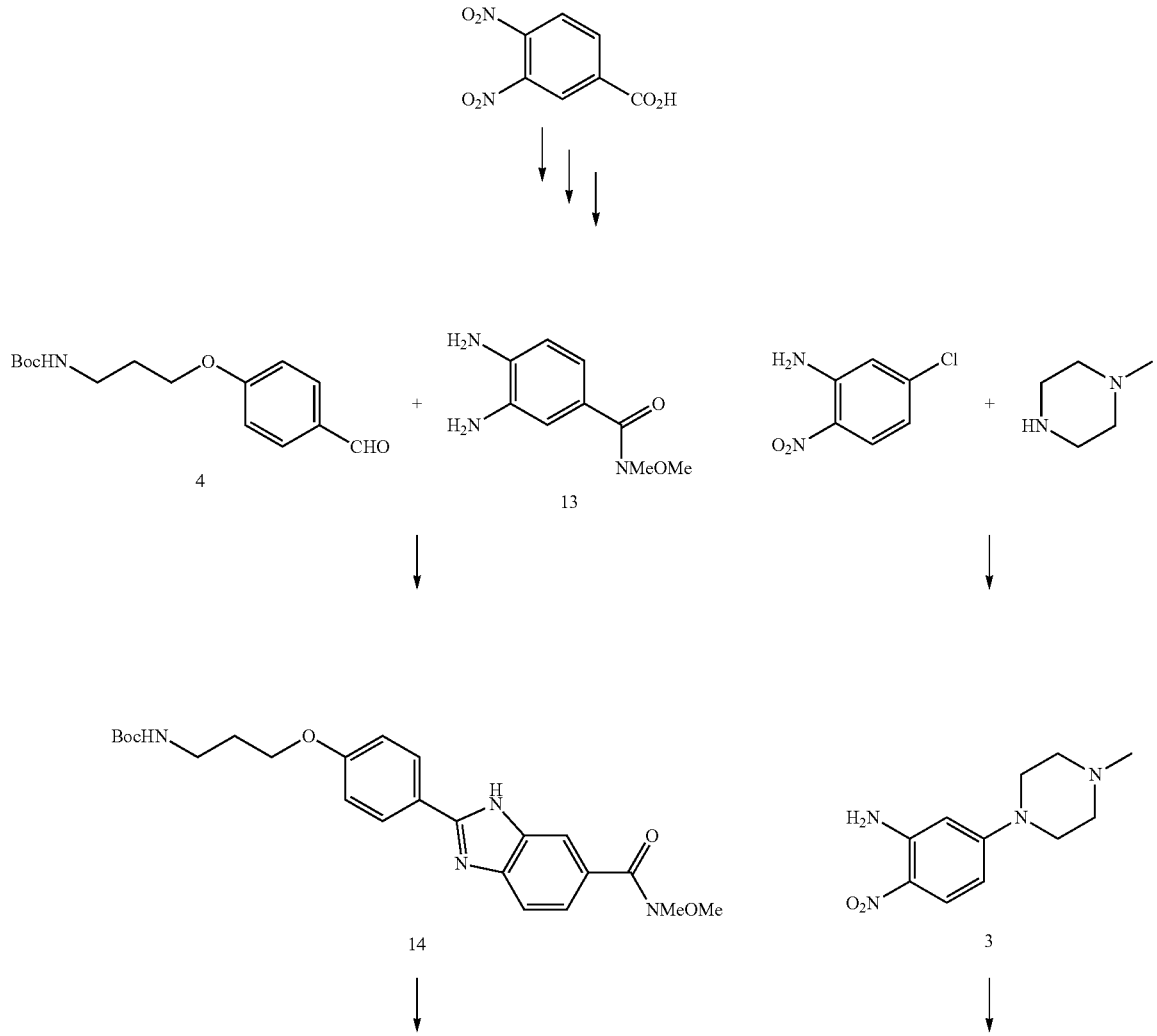

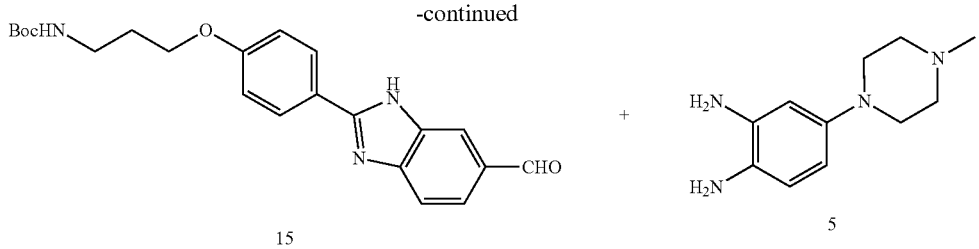

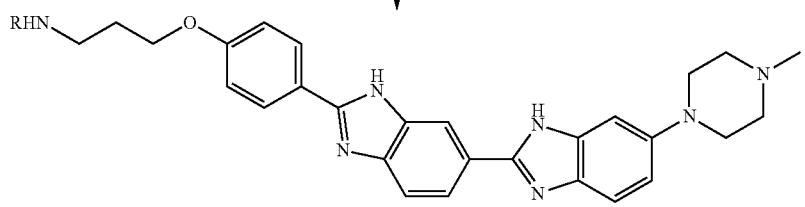

16: R = Boc
17: R = H

N-Methoxy-N-methyl-3.4.diaminobenzamide (13)

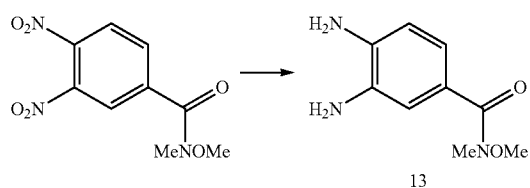

2-(4-N-Boc-phenoxy-propylamine)-benzimidazole-5-carboxylic acid methoxy-methylamide (14)

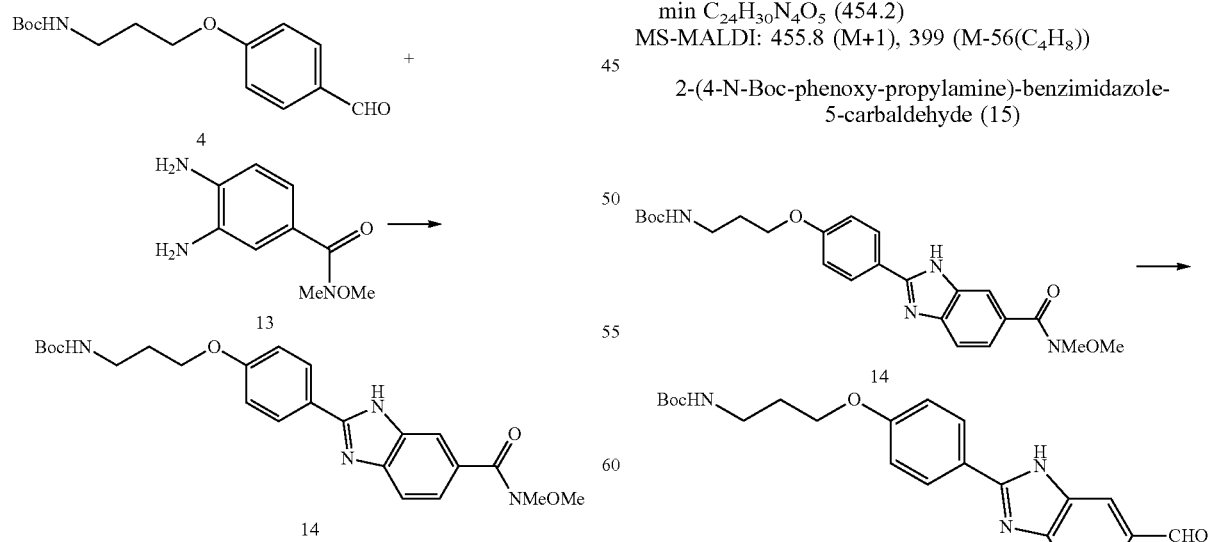

2.6 g Weinrebamide of 3.4-dinitrobenzoic acid (10.2 mmol) were reduced under a hydrogen atmosphere to give quantitively the corresponding N-methoxy-N-methyl-3.4.diaminobenzamide 13 (10.2 mmol). This reduction solution was used without any further purification in the reaction with N-Boc-protected aldehyde 4.

A solution of 4.2 g N-Boc-protected aldehyde 4 (15 mmol) in 100 ml EtOH was added to a solution of 1.54 g (8.1 mmol) $Na_2S_2O_5$ in 3 ml $H_2O$. A yellow-grey precipitate was observed. The resulting suspension was allowed to stir for further 15 min at room temperature. The filtrated reduction solution of 10.2 mmol N-methoxy-N-methyl-3.4.diaminobenzamide 13 in EtOH was added to this suspension and the reaction mixture was heated for 30 minutes at 65° C. The completion of reaction was detected by TLC (ethyl acetate). The solvents were removed i. vac. and the remaining residue was purified by sc-chromatography by a gradient $CHCl_3$/ethyl acetate: 100/0→0/100.

4.0 g of Weinreb amide 14 were isolated (86% yield over two reaction steps)

HPLC: Luna 3μ, Phenyl-Hexyl, MeCN/$H_2O$ (98:2), $R_t$ 16.3 min $C_{24}H_{30}N_4O_5$ (454.2)

MS-MALDI: 455.8 (M+1), 399 (M-56($C_4H_8$))

2-(4-N-Boc-phenoxy-propylamine)-benzimidazole-5-carbaldehyde (15)

1.3 g N-Boc Weinreb amide 14 (2.9 mmol) were suspended in 24 ml tetrahydrofurane and 8 ml diethylether. This suspension was cooled to −80° C. and 320 mg (9 mmol) LiAlH₄ were added. The resulting suspension was heated to −30° to −15° C. The end of reduction was observed by TLC (ethyl acetate/hexane: 9/1). The reaction mixture was treated successively with ethyl acetate, MeOH and aqueous saturated NH₄Cl solution. The organic phase were separated, dried (Na₂SO₄) and the solvent were evaporated i. vac. 1.05 g of N-Boc-aldehyde 15 were isolated by sc-chromatography. (92% yield). This aldehyde 15 was used without any further purification in the following oxidative cyclization.

HPLC: Luna 3μ, Phenyl-Hexyl, MeCN/H₂O (98:2), R$_t$ 16.3 min C$_{22}$H$_{25}$N$_3$O$_4$ (395.5)

MS-MALDI: 455.8 (M+1), 399 (M-56(C$_4$H$_8$))

2-(4-N-Boc-phenoxy-propylamine)-bis(benzimidazole) 6-(4-methylpiperazin) (16)

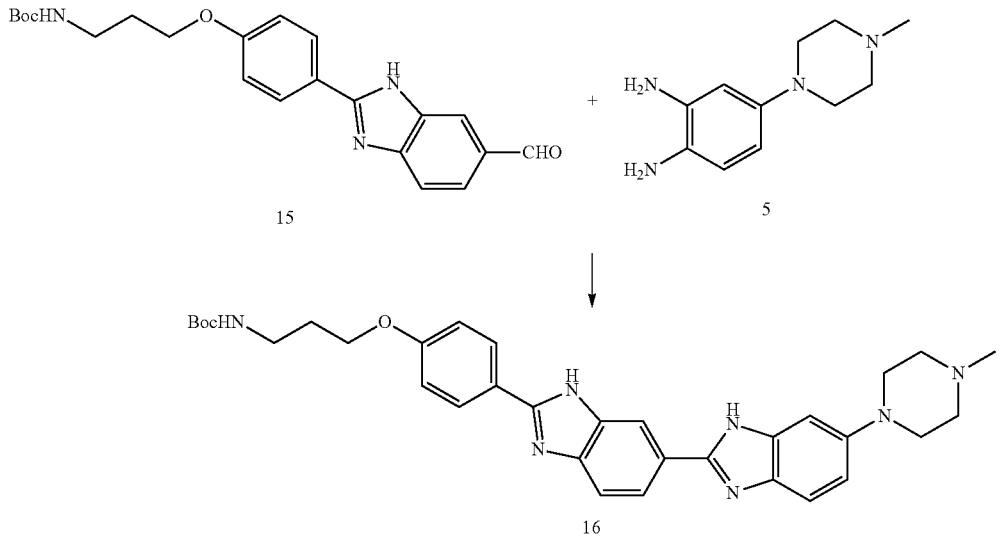

15

470 mg piperazinyl nitroaniline 3 (2.0 mmol) were reduced under a hydrogen atmosphere to give quantitively the corresponding piperazinyl diamine 5. This reduction solution was used without any further purification in the reaction with N-Boc-protected aldehyde 15.

1.07 g N-Boc-protected aldehyde 15 (2.7 mmol) in 30 ml EtOH were added to a solution of 385 mg Na₂S₂O₅ (2.0 mmol) in 2 ml H₂O. A grey precipitate occurs. The suspension was allowed to stir for 30 min at room temperature. The solution of piperazinyl diamine 5 was added to this suspension and the reaction mixture was heated of 60° C. for 2 hours. DC-control indicates complete conversion of the piperazionyl diamine 5. Celite was added and the solvent was evaporated i. vac. The solid residue was purified by sc-chromatography. gradient: CHCl₃/MeOH (100/0→95/5).

HPLC: Luna 3μ, Phenyl-Hexyl, MeCN/H₂O (98:2), R$_t$ 14.3 min C$_{33}$H$_{39}$N$_7$O$_3$ (581.3)

MS-MALDI: 582.1 (M+1)

$^1$H-NMR (DMSO-d$_6$): 1.38 (s, 9H), 1.87 (sept, J=6.6 Hz, 2H), 2.26 (s, 3H), 2.54 (m, 3H), 3.12 (tr, J=6.6 Hz, 2H), 3.13 (d, J=6.2 Hz, 2H), 3.31 (s, 3H), 4.07 (tr, J=6.2 Hz, 2H), 6.91 (m, 2H), 7.11 (d, J=7.6 Hz, 2H), 7.59 (d, J=8.3 Hz, 2H), 7.71 (d, J=8.4 Hz, 2H), 7.96 (d, J=8.1 Hz, 2H), 8.02 (d, J=8.1 Hz, 2H), 8.13 (dd, J=3.4, 8.3 Hz, 2H) 8.21 (m), 8.33 (m, 1H).

$^{13}$C-NMR (DMSO-d$_6$): 28.2, 29.1, 36.9, 45.6, 49.9, 54.8, 65.5, 77.5, 108.8, 111.3, 114.8, 116.1, 118.6, 120.3, 121.0, 122.3, 124.3, 128.2, 135.3, 136.0, 144.2, 145.0, 147.6, 152.7, 155.6, 160.2.

3-[4-(5-(4-methyl-1-piperazinyl)-(2,5'-bis-1H-benzimidazol-2-yl]-phenoxy-propylamine 17)

(Frau, S., et al., *New J. Chem.* 1995, 19, 873-6)

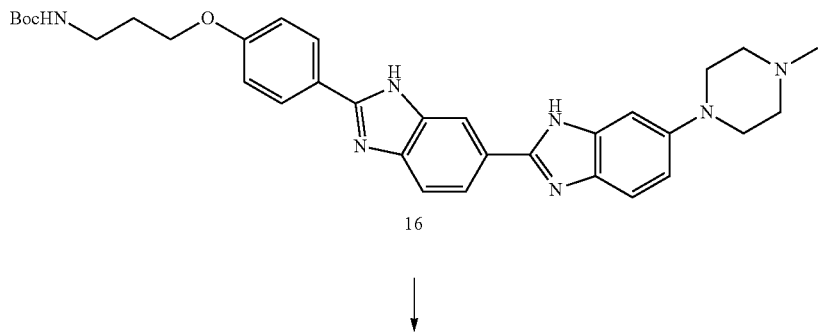

16

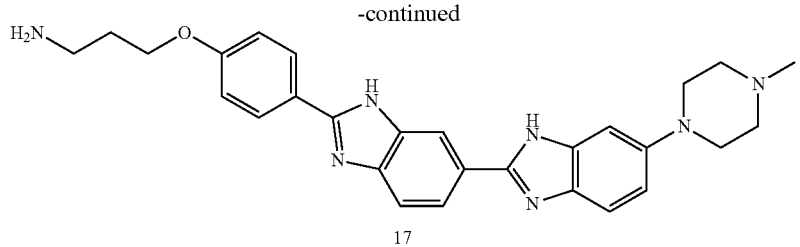

17

3 mg N-Boc-protected Hoechst 16 (1.4 mmol) were dissolved in 5 ml MeOH. This solution was acidified by HCl/MeOH. After 24 h at room temperature a full deprotection was detected by TLC. The product crystallized in the reaction mixture. 400 mg were isolated by filtration (60% yield).
$R_f$: ~0.5 CHCl$_3$/MeOH/H$_2$O$_{NH3}$: 2/8/0.5
HPLC: Luna 3μ, Phenyl-Hexyl, MeCN/H$_2$O (98:2), $R_t$: 14.3 min C$_{28}$H$_{31}$N$_7$O (481.6)
MS-MALDI: 481.7
$^1$H-NMR (DMSO-d$_6$): 2.09 (quint, J=6.4 Hz, 2H), 2.83 (d, J=3.6 Hz, 3H), 3.00 (sext, J=5.7 Hz, 2H), 3.22 (m, 4H), 3.53 (m, J=8.4 Hz, 2H), 3.89 (m, J=9.4 Hz, 2H), 4.23 (tr, J=6.1 Hz, 2H), 7.21 (d, J=2.0 Hz, 1H), 7.24 (d, J=9.1 Hz, 2H), 7.35 (dd, J=2.1, 9.0 Hz, 1H), 7.72 (d, J=9.0 Hz, 1H), 7.98 (d, J=8.5 Hz, 1H), 8.38 (d, J=8.6 Hz, 1H), 8.42 (d, J=8.7 Hz, 2H), 8.77 (s, 1H),
$^{13}$C-NMR (DMSO-d$_6$): 26.9, 36.1, 41.9, 46.2, 52.0, 65.2, 98.9, 113.8, 114.2, 114.4, 115.2, 115.3, 117.2, 117.9, 118.7, 123.7, 126.2, 129.9, 133.2, 147.9, 148.7, 152.7, 161.7.

Example 8: Binding Double Stranded DNA to Coupled Agarose Beads with Affinity Ligands YO—C$_3$, TO-C$_3$, TO-C$_6$, MCMB, Mono-Hoechst-C$_3$, L-Hoechst-C$_3$ and R-Hoechst-C$_2$ were synthesized as set forth above and coupled to an agarose bead. The coupling of the functionalized agarose bead to the affinity ligand was achieved through the synthetic routes shown in Table 3.

TABLE 3

| Resin | Affinity Ligand | Dye Ligand Density [μmol/mL resin] | Synthetic Route |
| --- | --- | --- | --- |
| YO-C$_3$ | (benzoxazole-quinolinium structure with propyl-NH$_2$, Cl$^-$, N-CH$_3$) | 13, 14, 19, 29 | Formation of Schiff's Base with aldehyde-activated agarose. Reductive Amination with NaCNBH$_3$. |
| TO-C$_3$ | (benzothiazole-quinolinium structure with propyl-NH$_2$, Cl$^-$, N-CH$_3$) | 7, 13, 19 | Formation of Schiff's Base with aldehyde-activated agarose. Reductive Amination with NaCNBH$_3$. |

TABLE 3-continued

| Resin | Affinity Ligand | Dye Ligand Density [μmol/mL resin] | Synthetic Route |
|---|---|---|---|
| TO-C$_6$ | (structure) | 12, 19, 28 | Formation of Schiff's Base with aldehyde-activated agarose. Reductive Amination with NaCNBH$_3$. |
| MCMB | (structure) | 6 | Chemical conjugation of an NHS ester with a primary amine to form an amide bond. Reaction with Amino-activated agarose. |
| Mono-Hoechst-C$_3$ | (structure) | 12, 19, 26 | Formation of Schiff's Base with aldehyde-activated agarose. Reductive Amination with NaCNBH$_3$. |
| L-Hoechst-C$_3$ | (structure) | 12, 18, 41 | Formation of Schiff's Base with aldehyde-activated agarose. Reductive Amination with NaCNBH$_3$. |
| R-Hoechst-C$_3$ | (structure) | 9 | Formation of Schiff's Base with aldehyde-activated agarose. Reductive Amination with NaCNBH$_3$. |

Each of coupled agarose-affinity ligands, referred to as resin was then tested for binding ds (double-stranded) DNA according to the following procedure. 100 μL resin was placed in a mini spin column and equilibrated in buffer (0.05 M TRIS, 0.5 M NaCl, pH 7.1). 200 μL of the ds DNA solution (Invitrogen, cat. No. 15634-017, LOT 1885913) was added at room temperature (RT) to create a suspension. The suspension was incubated for 90 min at RT and mixed every 30 min on the vortexer. After 90 min the supernatant was centrifuged off, the liquid collected and measured with the UV photometer at 260 nm to detect the amount of DNA present in the liquid that did not bind to the resin. The resin was washed once with buffer. The washing solution was also measured. In most cases only a small amount of DNA was detected.

Figure 6:
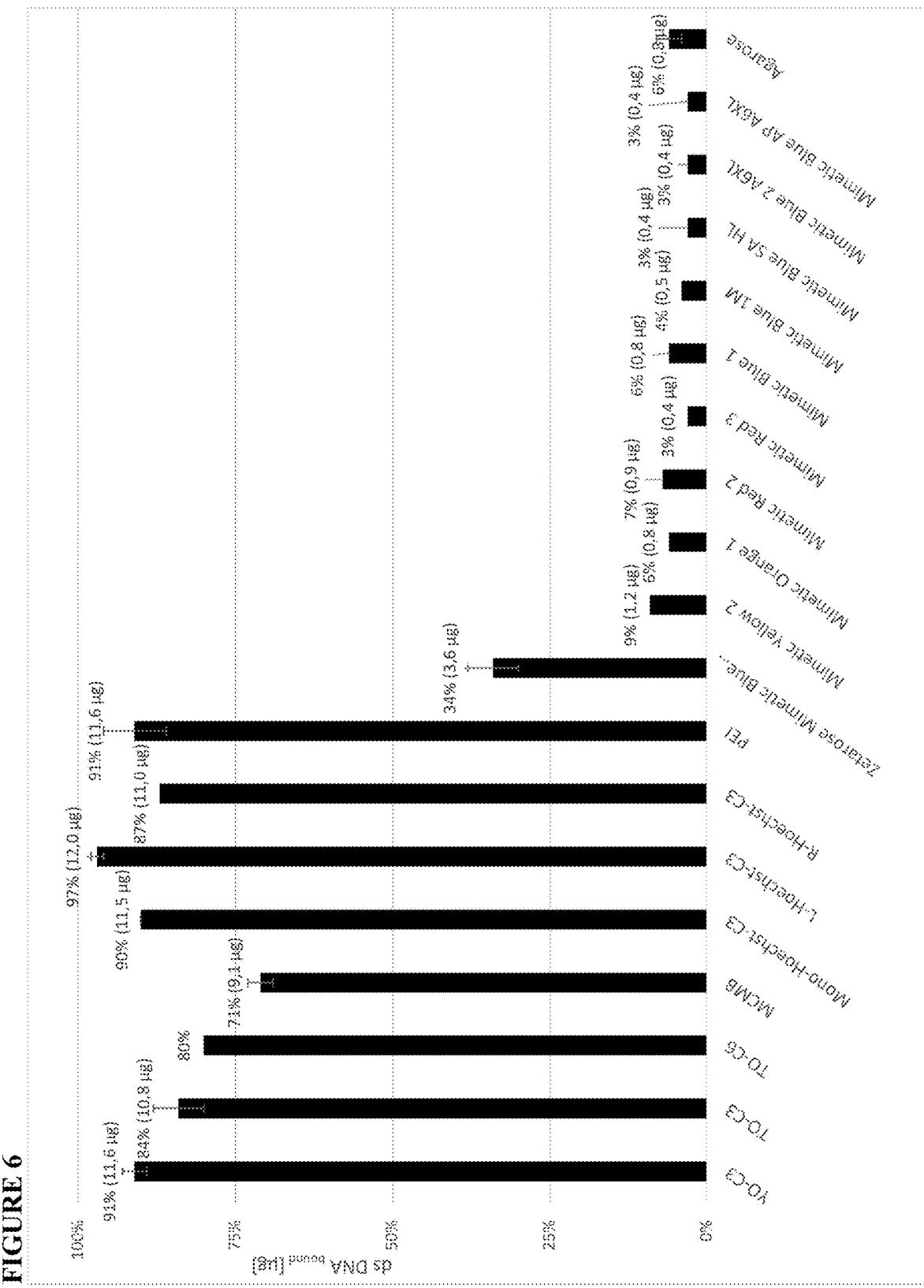
FIG. 6 is a bar graph showing binding of ds DNA to the coupled agarose-affinity ligand resin with a loading solution with ~11-13 µg ds DNA on 100 µl gel in a spin column.

If 100% of the DNA bound to the resin, then the absorption at 260 nm would be 0. Conversely, if no DNA bound to the resin, the absorption would be 100%. Thus, one can measure the amount of DNA bound to the resin based on the UV absorption of the liquid. The results are shown in Table 4 and in FIG. 6. FIG. 6 is a bar graph showing the resulting binding of dsDNA to the tested resins with a loading solution with ~11-13 µg ds DNA on 100 µl gel in a spin column.

TABLE 4

| Resin | % DNA bound | Margin of error | DNA bound [µg] | Loading density of the intercalator [µmol dye/mL gel] |
|---|---|---|---|---|
| YO-$C_3$ | 91% | 2% | 11.6 | 13.6 |
| TO-$C_3$ | 84% | 4% | 10.8 | 13.2 |
| TO-$C_6$ | 80% |  | 10.2 | 13.4 |
| MCMB | 71% | 2% | 9.1 | 6.2 |
| Mono-Hoechst-$C_3$ | 90% | 0% | 11.5 | 12.0 |
| L-Hoechst-$C_3$ | 97% | 1% | 12.0 | 12,.0 |
| R-Hoechst-$C_3$ | 87% |  | 11.0 | 9.0 |
| PEI | 91% | 5% | 11.6 |  |
| Zetarose Mimetic Blue Dye 1FF | 34% | 4% | 4.4 | 4.8 |
| Mimetic Yellow 2 | 9% |  | 1.2 | n/a |
| Mimetic Orange 1 | 6% |  | 0.8 | n/a |
| Mimetic Red 2 | 7% |  | 0.9 | n/a |
| Mimetic Red 3 | 3% |  | 0.4 | n/a |
| Mimetic Blue 1 | 6% |  | 0.8 | n/a |
| Mimetic Blue 1M | 4% |  | 0.5 | n/a |
| Mimetic Blue SA HL | 3% |  | 0.4 | n/a |
| Mimetic Blue 2 A6XL | 3% |  | 0.4 | n/a |
| Mimetic Blue AP A6XL | 3% |  | 0.4 | n/a |
| Agarose | 6% | 2% | 0.8 |  |

Table 5 provides more information on the compounds and sources for the products used in this experiment.

TABLE 5

| Resin | LOT | ds DNA-Amount |
|---|---|---|
| YO-$C_3$ | YO3-FF4-200421 | Amount ds DNA: 12.8 µg |
| TO-$C_3$ | TO3- FF4-200421 | Amount ds DNA: 12.8 µg |
| TO-$C_6$ | #045-TO-HA-01 | Amount ds DNA: 12.7 µg |
| MCMB | # FF4-MCMB-190118 | Amount ds DNA: 12.8 µg |
| Mono-Hoechst-$C_3$ | #025-MHoechst-PA-01 | Amount ds DNA: 12.8 µg |
| L-Hoechst-$C_3$ | AN1 LH + ALD20 | Amount ds DNA 12.2 und 12.6 µg |
| R-Hoechst-$C_3$ | LJ-P1605-037, RH-EA + CHO-Agarose20 | Amount ds DNA: 12.6 µg |
| PEI | evtl: Appli Chrom, Kat. Nr.: AC-BPEIMA20E6-208-100, LOT 180307 | Amount ds DNA 12.6 µg und 12.7 µg |
| Zetarose Mimetic Blue Dye 1FF | CX068A01 (Astrea Bioseparations: Mimetic Blue SA P6XL) | Amount ds DNA: 12.2 und 13.8 µg |
| Mimetic Yellow 2 | Astrea Bioseparations, FA0785 | Amount ds DNA: 13.1 µg |
| Mimetic Orange 1 | Astrea Bioseparations, FA0960 | Amount ds DNA: 13.1 µg |

TABLE 5-continued

| Resin | LOT | ds DNA-Amount |
|---|---|---|
| Mimetic Red 2 | Astrea Bioseparations, FA0577 | Amount ds DNA: 13.1 µg |
| Mimetic Red 3 | Astrea Bioseparations, FA1595 | Amount ds DNA: 13.1 µg |
| Mimetic Blue 1 | Astrea Bioseparations, FA1735 | Amount ds DNA: 13.1 µg |
| Mimetic Blue 1M | Astrea Bioseparations, FA1696 | Amount ds DNA: 13.1 µg |
| Mimetic Blue SA HL | Astrea Bioseparations, FA1410 | Amount ds DNA: 13.1 µg |
| Mimetic Blue 2 A6XL | Astrea Bioseparations, FA1271 | Amount ds DNA: 13.1 µg |
| Mimetic Blue AP A6XL | Astrea Bioseparations, FA1070 | Amount ds DNA: 13.1 µg |
| Agarose | Zetarose FF4-Agarose, emp LOT: #11-058175-4RR01 | Amount ds DNA: 12.8 µg |

Figure 7:
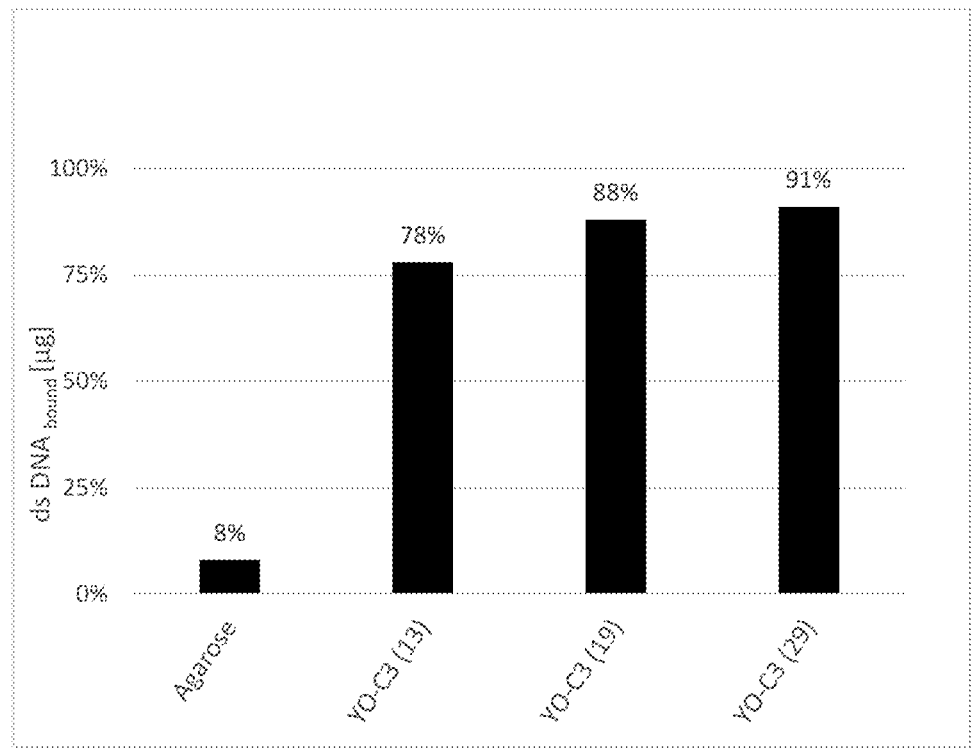
FIG. 7 is a bar graph showing binding of ds DNA to the coupled agarose-YO—$C_3$ resin with a loading solution with ~12 µg ds DNA on 100 µl gel in a spin column.
Figure 8:
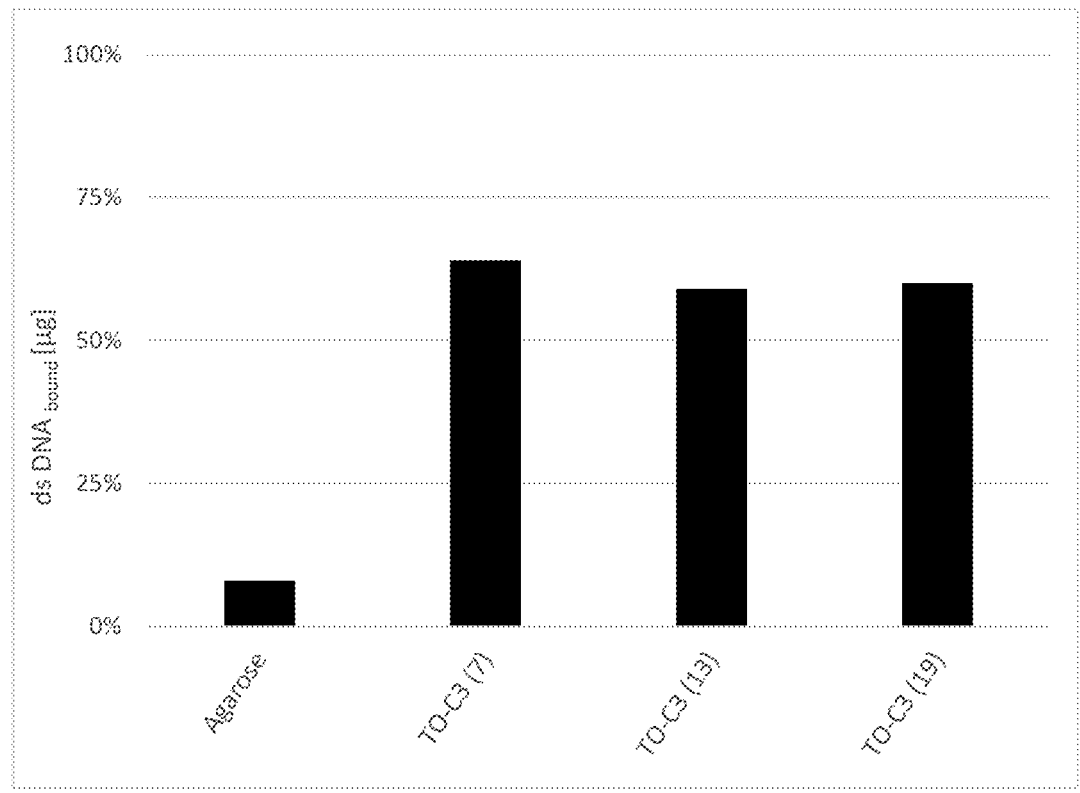
FIG. 8 is a bar graph showing binding of ds DNA to the coupled agarose-TO-$C_3$ resin with a loading solution with ~12 µg ds DNA on 100 µl gel in a spin column.
Figure 9:
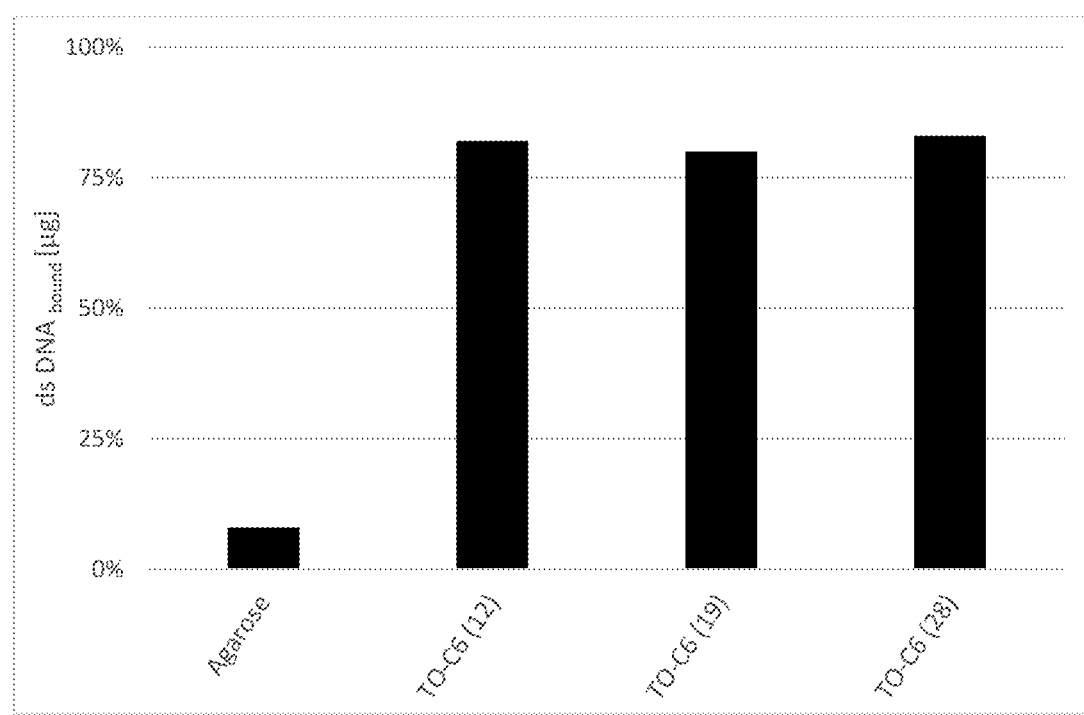
FIG. 9 is a bar graph showing binding of ds DNA to the coupled agarose-TO-$C_6$ resin with a loading solution with ~12 µg ds DNA on 100 µl gel in a spin column.

As shown in FIG. 7, YO—$C_3$, TO-$C_3$, TO-$C_6$, MCMB, Mono-Hoechst-$C_3$, L-Hoechst-$C_3$ and R-Hoechst-$C_3$ successfully separated and bound ds DNA out of the sample. PEI was included as the positive control. It is an imine polymer of positively charged amino groups, which has a natural ionic interaction with DNA. Mimetic Yellow 2, Mimetic Orange 1, Mimetic Red 2, Mimetic Red 3, Mimetic Blue 1, Mimetic Blue 1M, Mimetic Blue SA HL, Mimetic Blue SA HL, Mimetic Blue 2 A6XL, and Mimetic Blue AP A6XL are dyes that are not intercalators with DNA. They were included as negative control dyes. Zetarose Mimetic Blue Dye 1FF was also included as a negative control that coincidentally had more affinity to DNA than the other nonintercalating dyes. 6% of ds DNA bound to the unaltered agarose bead. This is the effects of non-specific binding. Accordingly, this data shows that intercalating small molecules successfully and selectively bound DNA.

Example 9: Effects of Different Dye Ligand Density on Binding DNA

Figure 10:
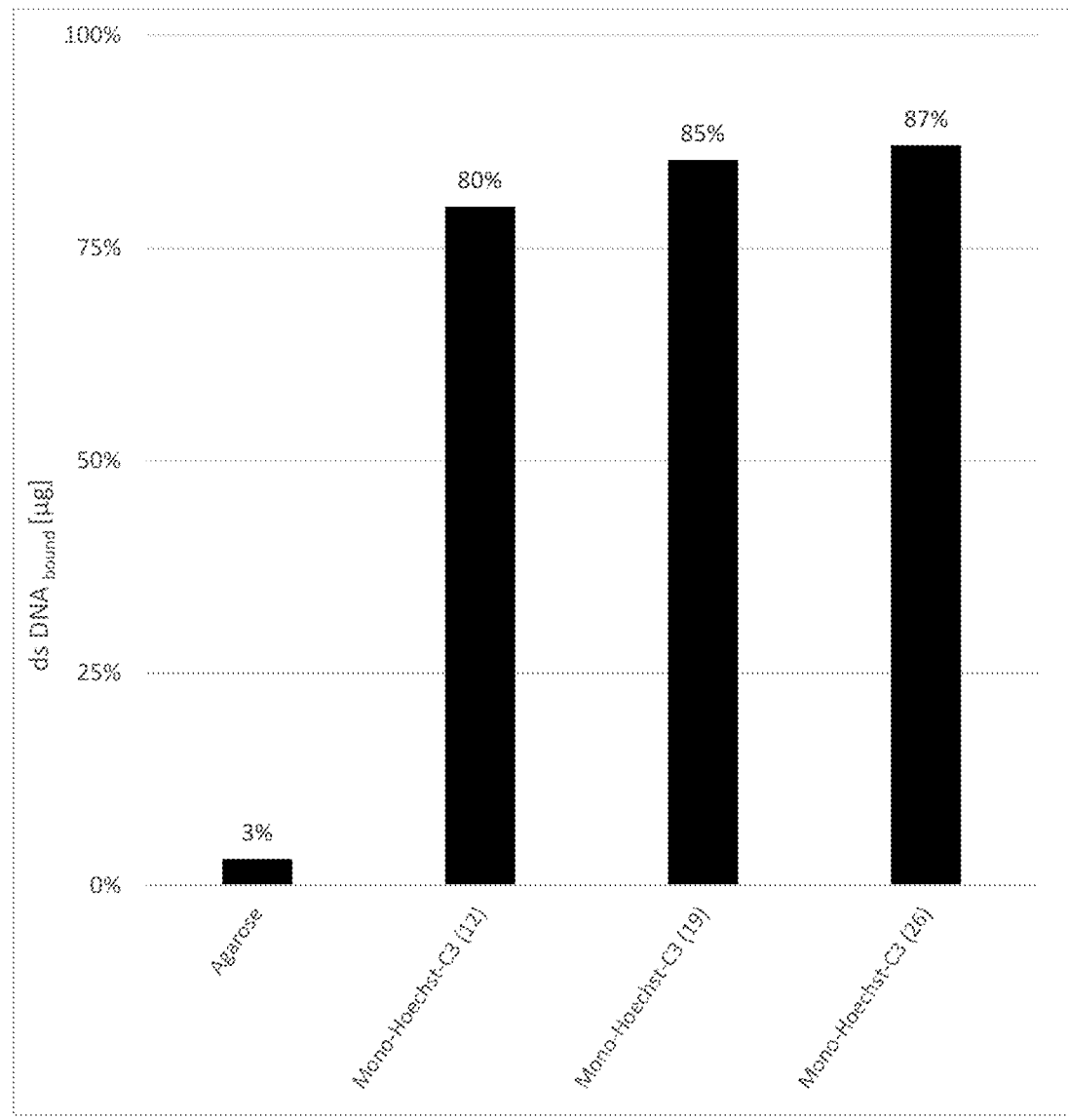
FIG. 10 is a bar graph showing binding of ds DNA to the coupled agarose-Mono-Hoechst-$C_3$ resin with a loading solution with ~18 µg ds DNA on 100 µl gel in a spin column.
Figure 11:
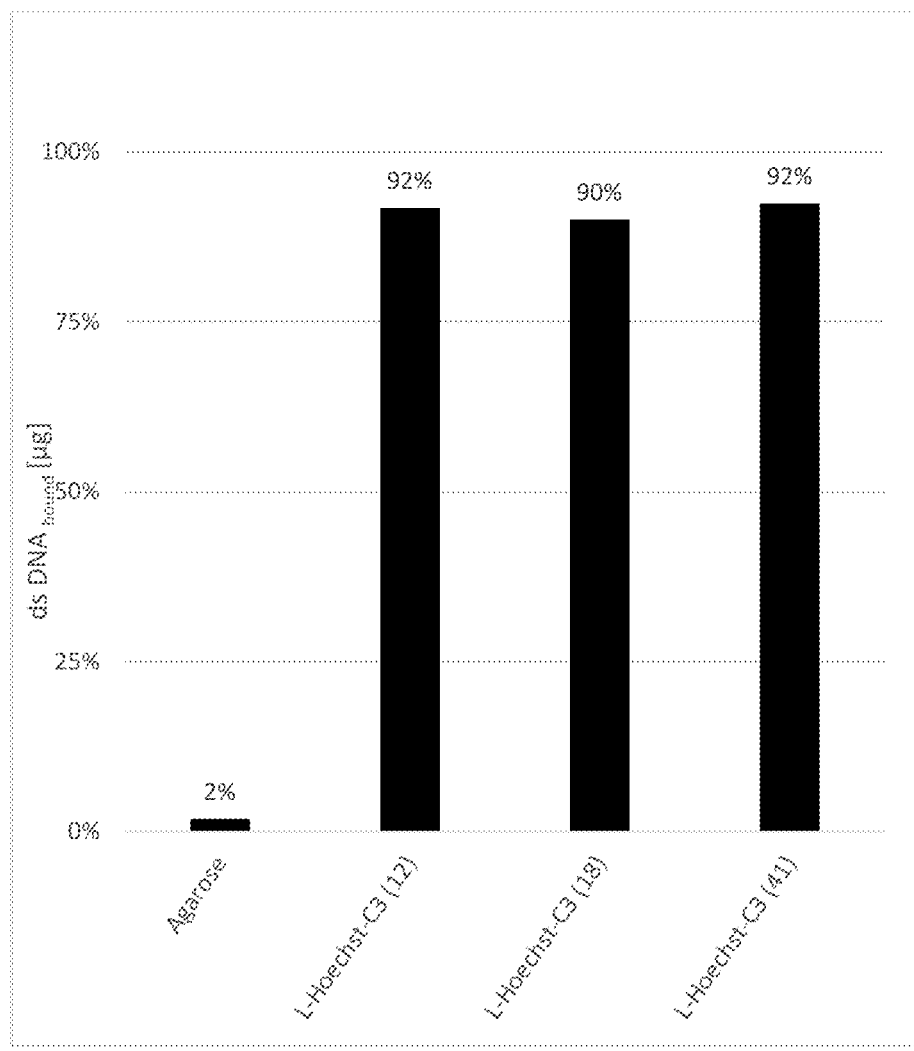
FIG. 11 is a bar graph showing binding of ds DNA to the coupled agarose-L-Hoechst-$C_3$ resin with a loading solution with ~12 µg ds DNA on 100 µl gel in a spin column.

The dye ligand density represents the number or amount of per volume of solid bead. It was anticipated that the higher the density, the more DNA that could be bound to the coupled surface-affinity ligand. This theory was tested by performing the procedures as explained in Example 8 with the resins of different densities shown in Table 3. The results are shown in Tables 6-10 and graphed in FIGS. 7-11. FIGS. 7, 8, 9, 11 show binding of ds DNA to the tested resins with a loading solution with ~12 µg ds DNA on 100 µl gel in a spin column. FIG. 10 shows binding of ds DNA to the coupled agarose to Mono-Hoechst-$C_3$ resin with a loading solution with ~18 µg ds DNA on 100 µl gel in a spin column. In all of these figures, the amount of ds DNA binding to the resin is compared to the amount bound to the control agarose bead.

TABLE 6

| Resin | % $DNA_{bound}$ | m $DNA_{bound}$ [µg] |
|---|---|---|
| Agarose | 8% | 0.8 |
| YO-$C_3$ (13) | 78% | 9.2 |
| YO-$C_3$ (19) | 88% | 10.4 |
| YO-$C_3$ (29) | 91% | 10.8 |

LJ-P1605-014, 017, 12.0 µg dsDNA

TABLE 7

| Resin | % DNA$_{bound}$ | m DNA$_{bound}$ [μg] |
|---|---|---|
| Agarose | 8% | 0.8 |
| TO-C$_3$ (7) | 64% | 7.5 |
| TO-C$_3$ (13) | 59% | 7.0 |
| TO-C$_3$ (19) | 60% | 7.1 |

LJ-P1605-014, 017, 12.0 μg dsDNA

TABLE 8

| Resin | % DNA$_{bound}$ | m DNA$_{bound}$ [μg] |
|---|---|---|
| Agarose | 8% | 0.8 |
| TO-C$_6$ (12) | 82% | 9.0 |
| TO-C$_6$ (19) | 80% | 8.7 |
| TO-C$_6$ (28) | 83% | 9.1 |

LJ-P1605-017, 12.0 μg dsDNA

TABLE 9

| Resin | % DNA$_{bound}$ | m DNA$_{bound}$ [μg] |
|---|---|---|
| Agarose | 3% | 0.6 |
| Mono-Hoechst-C$_3$ (12) | 80% | 14.4 |
| Mono-Hoechst-C$_3$ (19) | 85% | 15.4 |
| Mono-Hoechst-C$_3$ (26) | 87% | 15.7 |

LJ-P1605-027, 18.1 μg dsDNA

TABLE 10

| Resin | % DNA$_{bound}$ | m DNA$_{bound}$ [μg] |
|---|---|---|
| Agarose | 2% | 0.2 |
| L-Hoechst-C$_3$ (12) | 92% | 11.0 |
| L-Hoechst-C$_3$ (18) | 90% | 10.8 |
| L-Hoechst-C$_3$ (41) | 92% | 11.1 |

LJ-P1605-035, 12.0 μg dsDNA

Example 10: DNA Recovery

Recovery of ds DNA from the coupled surface-affinity ligands prepared and shown in Tables 3 and 4 was attempted using a variety of different solvents, including: 1) 4 M NaCl, 2) 4 M NaCl and 95° C., 3) pH 2 (0.1 M Glycine, pH 2.0), and 4) pH 10 (0.2 M Na$_2$CO$_3$, pH 10).

Tables 11-15 display the amount (%) ds DNA separated and recovered from each resin using the different recovery methods and solvents.

TABLE 11

Recovery with 4 NaCl

| Resin | DNA$_{bound}$ [μg] | DNA$_{Elution\ total}$ [μg] | DNA$_{Elution\ total\ total}$ [%] |
|---|---|---|---|
| YO-C$_3$ | 11.6 | 2.3 | 20% |
| TO-C$_3$ | 10.8 | 1.7 | 16% |
| TO-C$_6$ | 9.9 | 4.6 | 46% |
| MCMB | 9.1 | 4.4 | 48% |
| Mono-Hoechst-C$_3$ | 11.5 | 2.6 | 22% |
| L- Hoechst-C$_3$ | 11.0 | 0.8 | 7% |

TABLE 12

Recovery with 4 NaCl, 95° C.

| Resin | DNA$_{bound}$ [μg] | DNA$_{Elution\ total}$ [μg] | DNA$_{Elution\ total\ total}$ [%] |
|---|---|---|---|
| YO-C$_3$ | 11.6 | 3.8 | 33% |
| TO-C$_3$ | 10.8 | 1.8 | 17% |
| TO-C$_6$ | 9.9 | 3.1 | 31% |
| MCMB | 9.1 | 2.5 | 27% |
| Mono-Hoechst-C$_3$ | 11.5 | 2.4 | 21% |

TABLE 13

Recovery with pH 2.0

| Resin | DNA$_{bound}$ [μg] | DNA$_{Elution\ total}$ [μg] | DNA$_{Elution\ total\ total}$ [%] |
|---|---|---|---|
| YO-C$_3$ | 11.8 | 0.9 | 7% |
| TO-C$_3$ | 10.5 | 1.6 | 15% |
| TO-C$_6$ | 9.0 | 1.2 | 13% |
| MCMB | 8.0 | 0.9 | 11% |
| Mono-Hoechst-C$_3$ | 11.9 | 0.9 | 7% |
| L- Hoechst-C3 | 10.8 | 0.3 | 3% |
| PEI | 114.0 | 0.6 | 1% |

TABLE 14

Recovery with pH 10.0

| Resin | DNA$_{bound}$ [μg] | DNA$_{Elution\ total}$ [μg] | DNA$_{Elution\ total\ total}$ [%] |
|---|---|---|---|
| YO-C$_3$ | 10.9 | 0.2 | 2% |
| TO-C$_3$ | 8.9 | 0.8 | 9% |
| TO-C$_6$ | 7.8 | 0.5 | 6% |
| MCMB | 7.1 | 2.1 | 30% |
| Mono-Hoechst-C$_3$ | 11.0 | 2.7 | 25% |
| L- Hoechst-C3 | 10.5 | 0.9 | 9% |
| PEI | 113.4 | 21.7 | 19% |

Example 11: Binding of Double-Stranded (ds) and Single-Stranded (ss) DNA

Figure 12:
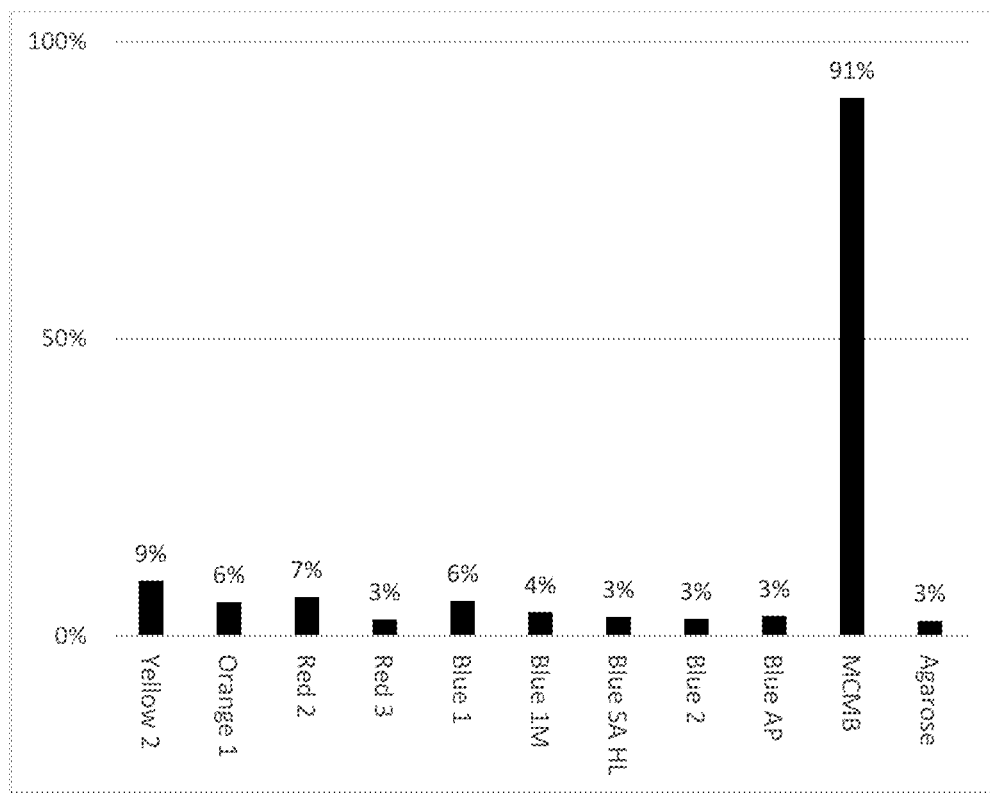
FIG. 12 is a bar graph showing binding of ds DNA per batch of loading buffer with 13.6 µg ds DNA on 100 µL gel in a spin column.
Figure 13:
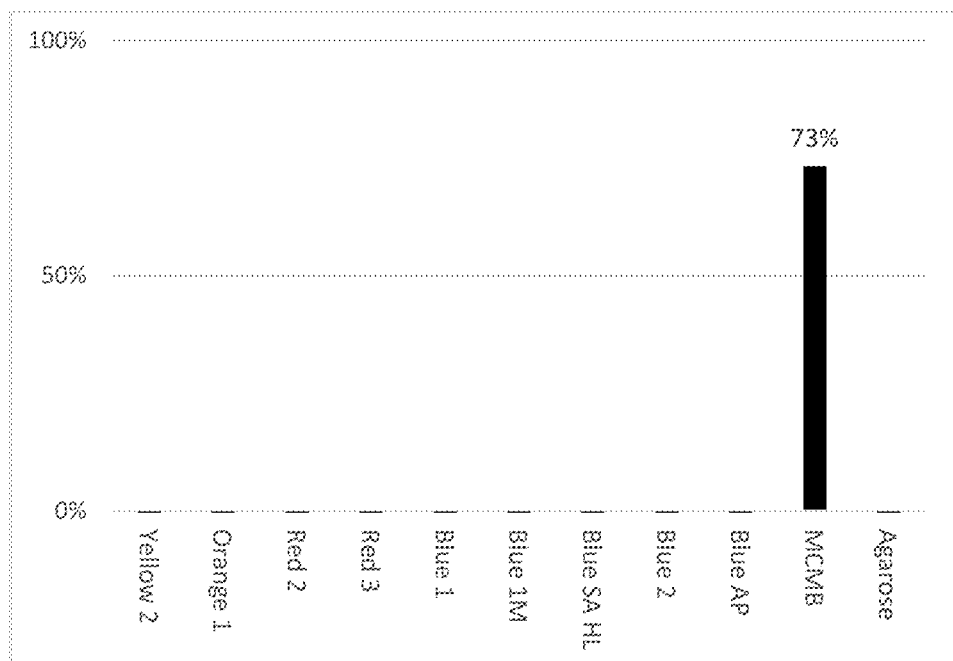
FIG. 13 is a bar graph showing binding of ss DNA per batch of loading buffer with 22.1 µg ss DNA on 100 µL gel in a spin column.

The binding assay was carried out with DNA (0.2 mL of ~67 ug/mL for ds DNA, 0.2 mL of ~166 ug/mL for ss DNA) and 100 uL resin. A number of non-intercalating dyes (Mimetic Yellow 2, Mimetic Orange 1, Mimetic Red 2, Mimetic Red 3, Mimetic Blue 1, Mimetic Blue 1M, Mimetic Blue SA HL and Mimetic Blue AP A6XL), unaltered agarose bead, and MCMB were tested for binding. The positive control was MCMB. For the ds DNA, the samples were loaded with a buffer with 13.6 μg ds DNA on 100 μL gel in a spin column. For the ss DNA, the samples were loaded with a buffer with 22.1 μg ss DNA on 100 μL gel in a spin column. The data is shown in FIGS. 12 and 13. As shown, none of the Mimetic resins from Astrea Biosciences bound ss DNA, and only a negligible amount of ds DNA, while MCMB successfully bound both ss DNA and ds DNA.

All of the non-MCMB resins had "negative" amounts of DNA binding, so there may have been an error in calibration. The negative results are reported here as "zero". The bound DNA is calculated by subtracting the measured mass of DNA of the sample to be loaded and the eluted DNA. This difference is the bound DNA. All measurements are based on the absorbance at 260 nm and calculating mass of DNA using Beer's Law.

Example 12: Selective Non-Binding of Proteins

The binding assay for DNA was carried out with the model protein Albumin to demonstrate selective non-binding for the coupled agarose-affinity ligands. As a positive control, PEI as well as Mimetic resins from Astrea Biosciences were used, because they are known to bind Albumin. The experiment was conducted using 0.2 ml, 1 mg/mL albumin, 0.1 ml resin, 90 min incubation time, Room Temp., 50 mM Tris/0.5 M NaCl buffer.

Figure 14:
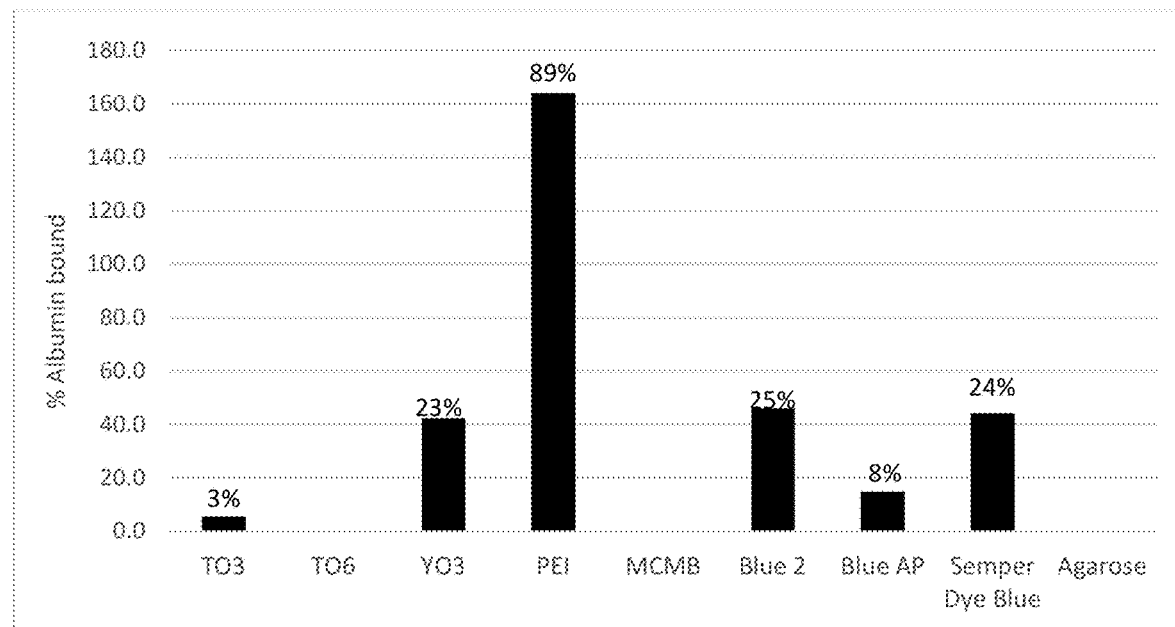
FIG. 14 is a bar graph showing binding capacity of albumin with a variety of resins.

FIG. 14 is a graph showing the results of the experiment, Binding of Albumin by Selected Resins. The coupled agarose-affinity ligands with TO-$C_3$, TO-$C_6$ and MCMB exhibited no binding of Albumin. YO—$C_3$ showed minimal binding with 0.4 mg Albumin/mL resin. The positive control, PEI, bound nearly all of the Albumin present (1.8 mg Albumin/mL resin). It is unknown why the Mimetic resins did not result in binding values similar to PEI.

This experiment demonstrates that non-binding of proteins is possible with the affinity ligands of the disclosure. However, proper selectivity will depend on the protein present in the sample, and use of the right affinity ligand.

While there have been described what are presently believed to be the certain desirable embodiments of the invention, those skilled in the art will realize that changes and modifications may be made thereto without departing from the spirit of the invention, and it is intended to include all such changes and modifications as fall within the true scope of the invention.

What is claimed:

1. A method of separating a target macromolecule from a sample, comprising the steps of:
   a. selecting an affinity ligand that will bind to the target macromolecule;
   b. binding the affinity ligand to a surface to create a coupled surface-affinity ligand;
   c. placing the coupled surface-affinity ligand into a container;
   d. introducing the sample containing the target macromolecule to the coupled surface-affinity ligand and causing the coupled surface-affinity ligand to incubate with the sample for a residence time, wherein the target macromolecule binds to the affinity ligand; and
   e. separating the coupled surface-affinity ligand bound to the target macromolecule from the sample that has the target macromolecule removed therefrom;
   wherein the target macromolecule is a double stranded DNA, wherein the affinity ligand is an intercalator and is a polyimidazole compound, wherein the compound has been modified to include a linker group capable of binding the affinity ligand to the surface, and wherein the affinity ligand is a modified Hoechst dye selected from:
      i. 3[4-(5-(4-methyl-1-piperazinyl)-(2.5'-bis-H-benzimidazol-2-yl]-phenoxy-ethylamine (L-Hoechst-$C_2$), 3-[4-(5-(4-methyl-1-piperazinyl) -(2,5'-bis-1H-benzimidazol-2-yl]-phenoxy-propylamine (L-Hoechst-$C_3$), or 3-1[4-(6-(4-methyl-1-piperazinyl)-1H-benzimidazol-2-yl]-phenoxy-propylamine (Mono-Hoechst-$C_3$); or
      ii. 2'-(4-Ethoxyphenyl)-6-(4-aminoethyl-1-piperazinyl)-2,6'-bis-1H-benzimidazole (R-Hoechst-$C_2$).

2. The method of claim 1, further comprising the step of:
   f. collecting an eluent that is substantially free of the target macromolecule.

3. The method of claim 1, further comprising the step of:
   f. eluting and recovering the target macromolecule from the coupled surface-affinity ligand.

4. The method of claim 1, wherein the affinity ligand selectively binds DNA and the affinity ligand does not bind proteins.

5. The method of claim 1, wherein the surface is a solid surface.

6. The method of claim 5, wherein the solid surface is a bead, membrane, particle, mesh, polymer, glass, metal, ceramic, silica, polysaccharide, monolith, or any other material used as a resin in chromatography.

7. The method of claim 6, wherein the solid surface includes a functionalized group.

8. The method of claim 7, wherein the functionalized group comprises an epoxy, a carboxy, an aldehyde, or an amino group.

9. The method of claim 6, wherein the solid surface is an amino-agarose bead.

10. The method of claim 6, wherein the solid surface is an aldehyde membrane.

11. The method of claim 1, wherein the method is used in chromatography.

12. The method of claim 1, wherein the container is a chromatography column, bowl, cylinder, conical-shaped vessel, or vat.

13. A method for isolating and removing DNA from a sample containing DNA and other nucleic acids, comprising the steps of:
   a. selecting an affinity ligand that will bind DNA;
   b. binding the affinity ligand to a surface to create a coupled surface-affinity ligand;
   c. placing the coupled surface-affinity ligand into a container;
   d. introducing the sample to the coupled surface-affinity ligand and causing the coupled surface-affinity ligand to incubate with the sample for a residence time, wherein the DNA binds to the affinity ligand; and
   e. separating the coupled surface-affinity ligand bound to the DNA from the sample that has the DNA removed therefrom,
   wherein the DNA is double stranded DNA, wherein the affinity ligand is an intercalator and is a polyimidazole compound, wherein the compound has been modified to include a linker group capable of binding the affinity ligand to the surface, and wherein the affinity ligand is a modified Hoechst dye selected from:
      i. 3-[4-(5-(4-methyl-1-piperazinyl)-(2.5'-bis-1H-benzimidazol-2-yl]-phenoxy-ethylamine(L-Hoechst-$C_2$), 3-[4-(5-(4-methyl-1-piperazinyl) -(2.5'-bis-1H-benzimidazol-2-yl]-phenoxy-propylamine (L-Hoechst-$C_3$), or 3-[4-(6-(4-methyl-1-piperazinyl)-1H-benzimidazol-2-yl]-phenoxy-propylamine (Mono-Hoechst-$C_3$); or
      ii. 2'-(4-Ethoxyphenyl)-6-(4-aminoethyl-1-piperazinyl)-2.6'-bis-1H-benzimidazole (R-Hoechst-$C_2$).

14. The method of claim 13, further comprising the step of:
   f. eluting and recovering the DNA from the coupled surface-affinity ligand.

15. The method of claim 13, wherein the surface is a solid surface.

16. The method of claim 15, wherein the solid surface is a bead, membrane, particle, mesh, polymer, glass, metal, ceramic, silica, polysaccharide, monolith, or any other material used as a resin in chromatography.

17. The method of claim 15, wherein the solid surface includes a functionalized group.

\* \* \* \* \*